(12) United States Patent
Hassler, Jr. et al.

(10) Patent No.: US 7,775,215 B2
(45) Date of Patent: Aug. 17, 2010

(54) SYSTEM AND METHOD FOR DETERMINING IMPLANTED DEVICE POSITIONING AND OBTAINING PRESSURE DATA

(75) Inventors: William L. Hassler, Jr., Cincinnati, OH (US); Daniel F. Dlugos, Morrow, OH (US); Lauren S. Weaner, Beavercreek, OH (US); Russell L. Holscher, West Chester, OH (US); Annie L. Ferreri, Loveland, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 1185 days.

(21) Appl. No.: 11/369,682

(22) Filed: Mar. 7, 2006

(65) Prior Publication Data

US 2006/0211914 A1 Sep. 21, 2006

Related U.S. Application Data

(63) Continuation-in-part of application No. 11/065,410, filed on Feb. 24, 2005.

(51) Int. Cl.
*A61B 19/00* (2006.01)
*A61F 2/00* (2006.01)
(52) U.S. Cl. .................... 128/899; 600/29; 600/37
(58) Field of Classification Search ............ 600/29–32, 600/37, 593; 128/DIG. 25, 899; 604/27–28, 604/909; 606/139–141, 151, 157, 191, 201–203, 606/213, 228
See application file for complete search history.

(56) References Cited

U.S. PATENT DOCUMENTS

| | | |
|---|---|---|
| RE03,036 E | 7/1868 | Shunk |
| RE03,037 E | 7/1868 | Tucker |
| RE03,115 E | 9/1868 | Lewis |
| RE03,187 E | 11/1868 | Winchester |

(Continued)

FOREIGN PATENT DOCUMENTS

AU  729 467  2/2001

(Continued)

OTHER PUBLICATIONS

European Search Report dated Jul. 23, 2007 for EP Application 07250932.

(Continued)

*Primary Examiner*—John P Lacyk
(74) *Attorney, Agent, or Firm*—Frost Brown Todd LLC

(57) ABSTRACT

A sense head comprises a plurality of coils and a needle window. The sense head is operable to receive RF signals communicated from a needle target such as an injection port located within a patient. A user interface is configured to visually display an indication to a user relating to the positioning and orientation of the sense head relative to the needle target. The positioning and orientation may be determined based on RF signals received by the coils in the sense head. With the sense head positioned based on information provided through the visual display, the user may insert a needle through the needle window to reach the needle target. The sense head may also receive communications relating to the pressure of fluid in an implanted device. The user interface may further display information relating to the fluid pressure in the implanted device.

20 Claims, 32 Drawing Sheets

U.S. PATENT DOCUMENTS

| | | | |
|---|---|---|---|
| RE03,322 E | 3/1869 | Murch | |
| 236,373 A | 1/1881 | Spilman | |
| 322,388 A | 7/1885 | Lord | |
| 400,401 A | 3/1889 | Gutzkow | |
| D23,637 S | 9/1894 | Casad et al. | |
| D24,900 S | 11/1895 | Clemecet | |
| D25,318 S | 3/1896 | Perky | |
| D57,151 S | 6/1897 | Moulten | |
| D29,715 S | 11/1898 | Wheeler | |
| D29,745 S | 11/1898 | Bunker | |
| D29,885 S | 12/1898 | Gillespie et al. | |
| D30,690 S | 5/1899 | Schwedtmann | |
| D30,966 S | 6/1899 | Howe | |
| D31,230 S | 7/1899 | Hogan | |
| 689,758 A | 12/1901 | Shaw | |
| 724,913 A | 4/1903 | Montgomery | |
| 899,477 A | 9/1908 | Williams | |
| 926,197 A | 6/1909 | Kim | |
| 953,875 A | 4/1910 | Waring | |
| 991,192 A | 5/1911 | Battenfeld | |
| 1,087,988 A | 2/1914 | Sheldon | |
| 1,210,701 A | 1/1917 | Ryden | |
| 1,219,296 A | 3/1917 | Hahn | |
| 1,224,355 A | 5/1917 | Brown | |
| 1,263,914 A | 4/1918 | Martin | |
| 1,310,290 A | 7/1919 | Piechowicz | |
| 1,384,873 A | 7/1921 | Strickland | |
| 1,421,507 A | 7/1922 | Lindberg | |
| 1,551,525 A | 8/1925 | Hamer | |
| 1,560,973 A | 11/1925 | Cheron | |
| 1,620,633 A | 3/1927 | Colvin | |
| 1,623,403 A | 4/1927 | Friel | |
| 1,689,085 A | 10/1928 | Russell et al. | |
| 1,764,071 A | 6/1930 | Foulke | |
| 1,782,704 A | 11/1930 | Woodruff et al. | |
| 1,807,107 A | 5/1931 | Sternberch | |
| 1,865,446 A | 7/1932 | Sears | |
| 1,882,338 A | 10/1932 | Reed et al. | |
| 1,924,781 A | 8/1933 | Gaiser | |
| 2,027,875 A | 1/1936 | Odend'hal | |
| 2,063,430 A | 12/1936 | Graser | |
| 2,099,160 A | 11/1937 | Charch | |
| 2,105,127 A | 1/1938 | Petrone | |
| 2,106,192 A | 1/1938 | Saville | |
| 2,143,429 A | 1/1939 | Auble | |
| 2,166,603 A | 7/1939 | Menzer | |
| 2,168,427 A | 8/1939 | McConkey | |
| 2,174,525 A | 10/1939 | Padernal | |
| 2,178,463 A | 10/1939 | Bahnson | |
| 2,180,599 A | 11/1939 | Menasco | |
| 2,177,564 A | 12/1939 | Havill | |
| 2,203,460 A | 6/1940 | Fieber | |
| 2,206,038 A | 7/1940 | Ford | |
| 2,216,374 A | 10/1940 | Martin | |
| 225,145 A | 12/1940 | Baumbach | |
| 2,223,699 A | 12/1940 | Norgren | |
| 2,225,880 A | 12/1940 | Montelius | |
| 2,261,060 A | 10/1941 | Giesler | |
| 2,261,355 A | 11/1941 | Flynn | |
| 2,295,539 A | 9/1942 | Beach | |
| 2,303,108 A | 11/1942 | Blackburn | |
| 2,303,502 A | 12/1942 | Rous | |
| 2,318,819 A | 5/1943 | Verson | |
| 2,327,407 A | 8/1943 | Edyvean | |
| 2,327,615 A | 8/1943 | Ankarlo | |
| 2,354,571 A | 7/1944 | Blain | |
| 2,396,351 A | 3/1946 | Thompson | |
| 2,426,392 A | 8/1947 | Fennema | |
| 2,426,817 A | 9/1947 | Carlton et al. | |
| 2,440,260 A | 4/1948 | Gall | |
| 2,442,573 A | 6/1948 | Stafford | |
| 2,453,217 A | 11/1948 | Gregg et al. | |
| 2,455,859 A | 12/1948 | Foley | |
| 2,477,922 A | 8/1949 | Emery et al. | |
| 2,478,876 A | 8/1949 | Nelson | |
| 2,482,392 A | 9/1949 | Whitaker | |
| 2,494,881 A | 1/1950 | Kost | |
| 2,509,210 A | 5/1950 | Clark | |
| 2,509,673 A | 5/1950 | Church | |
| 2,511,765 A | 6/1950 | Bradbury | |
| 2,520,056 A | 8/1950 | Pozun | |
| 2,521,976 A | 9/1950 | Hays | |
| 2,533,924 A | 12/1950 | Foley | |
| 2,538,259 A | 1/1951 | Merriman | |
| 2,581,479 A | 1/1952 | Grashman | |
| 2,600,324 A | 6/1952 | Rappaport | |
| 2,606,003 A | 8/1952 | McNeill | |
| 2,615,940 A | 10/1952 | Williams | |
| 2,632,447 A | 3/1953 | Dobes | |
| 2,639,342 A | 5/1953 | Cope | |
| 2,640,119 A | 5/1953 | Bradford, Jr. | |
| 2,641,742 A | 6/1953 | Wolfe | |
| 2,651,304 A | 9/1953 | Browner | |
| 2,665,577 A | 1/1954 | Sanowskis | |
| 2,673,999 A | 4/1954 | Shey | |
| 2,676,609 A | 4/1954 | Pfarrer | |
| 2,684,118 A | 7/1954 | Osmun | |
| 2,689,611 A | 9/1954 | Martinson | |
| 2,697,435 A | 12/1954 | Ray | |
| 2,723,323 A | 11/1955 | Niemi | |
| 2,734,992 A | 2/1956 | Elliot et al. | |
| 2,740,007 A | 3/1956 | Amelang | |
| 2,740,853 A | 4/1956 | Hatman, Jr. | |
| 2,742,323 A | 4/1956 | Shey | |
| 2,747,332 A | 5/1956 | Morehouse | |
| 2,753,876 A | 7/1956 | Kurt | |
| 2,756,883 A | 7/1956 | Schreck | |
| 2,756,983 A | 7/1956 | Furcini | |
| 2,761,603 A | 9/1956 | Fairchild | |
| 2,773,312 A | 12/1956 | Peck | |
| 2,783,728 A | 3/1957 | Hoffmann | |
| 2,787,875 A | 4/1957 | Johnson | |
| 2,793,379 A | 5/1957 | Moore | |
| 2,795,460 A | 6/1957 | Bletcher | |
| 2,804,514 A | 8/1957 | Peters | |
| 2,822,113 A | 2/1958 | Joiner, Jr. | |
| 2,831,478 A | 4/1958 | Uddenberg et al. | |
| 2,864,393 A | 12/1958 | Drake | |
| 2,865,541 A | 12/1958 | Hicks | |
| 2,870,024 A | 1/1959 | Martin | |
| 2,883,995 A | 4/1959 | Bialous et al. | |
| 2,886,355 A | 5/1959 | Wurzel | |
| 2,895,215 A | 7/1959 | Neher et al. | |
| 2,899,493 A | 8/1959 | Levine | |
| 2,902,861 A | 9/1959 | Frost et al. | |
| 2,923,531 A | 2/1960 | Bauer et al. | |
| 2,924,263 A | 2/1960 | Landis | |
| 2,924,432 A | 2/1960 | Arps et al. | |
| 2,930,170 A | 3/1960 | Holsman et al. | |
| 2,938,592 A | 5/1960 | Charske et al. | |
| 2,941,338 A | 6/1960 | Santschi | |
| 2,943,682 A | 7/1960 | Ingram , Jr. et al | |
| 2,958,781 A | 11/1960 | Marchal et al. | |
| 2,961,479 A | 11/1960 | Bertling | |
| 2,976,355 A | 3/1961 | Levine | |
| 2,976,686 A | 3/1961 | Stelzer | |
| 2,977,876 A | 4/1961 | Meyers | |
| 2,986,715 A | 5/1961 | Church et al. | |
| 2,989,019 A | 6/1961 | Van Sciver II | |
| 3,010,692 A | 11/1961 | Jentoft | |
| 3,013,234 A | 12/1961 | Bourns | |
| 3,018,791 A | 1/1962 | Knox | |
| 3,034,356 A | 5/1962 | Bieganski | |
| 3,040,800 A | 6/1962 | Hartley | |

| | | | | | |
|---|---|---|---|---|---|
| 3,054,618 A | 9/1962 | Abrams et al. | 3,393,612 A | 7/1968 | Gorgens et al. |
| 3,060,262 A | 10/1962 | Hoer | 3,396,561 A | 8/1968 | Day |
| 3,070,373 A | 12/1962 | Mathews et al. | 3,399,667 A | 9/1968 | Nishimoto et al. |
| 3,082,414 A | 3/1963 | Papaminas | 3,400,734 A | 9/1968 | Rosenberg |
| 3,085,577 A | 4/1963 | Berman et al. | 3,403,237 A | 9/1968 | Wysong |
| 3,096,410 A | 7/1963 | Anderson | 3,409,924 A | 11/1968 | Slama |
| 3,099,262 A | 7/1963 | Bigliano | 3,411,347 A | 11/1968 | Wirth et al. |
| 3,125,028 A | 3/1964 | Rohde | 3,417,476 A | 12/1968 | Martens |
| 3,126,029 A | 3/1964 | Englesson | 3,420,325 A | 1/1969 | McAlister et al. |
| 3,129,072 A | 4/1964 | Cook et al. | 3,422,324 A | 1/1969 | Webb |
| 3,135,914 A | 6/1964 | Callan et al. | 3,426,165 A | 2/1969 | Beaman |
| 3,144,017 A | 8/1964 | Muth | 3,438,391 A | 4/1969 | Yocum |
| 3,151,258 A | 9/1964 | Sondregger et al. | 3,443,608 A | 5/1969 | Copping et al. |
| 3,153,460 A | 10/1964 | Raskin | 3,445,335 A | 5/1969 | Gluntz |
| 3,161,051 A | 12/1964 | Perry, Jr. | 3,447,281 A | 6/1969 | Bufford et al. |
| 3,167,044 A | 1/1965 | Henrickson | 3,450,153 A | 6/1969 | Hildebrandt et al. |
| 3,171,549 A | 3/1965 | Orloff | 3,453,546 A | 7/1969 | Fryer |
| 3,172,700 A | 3/1965 | Haas | 3,453,848 A | 7/1969 | Williamson |
| 3,173,269 A | 3/1965 | Imbertson | 3,456,134 A | 7/1969 | Ko |
| 3,182,494 A | 5/1965 | Beatty et al. | 3,457,909 A | 7/1969 | Laird |
| 3,187,181 A | 6/1965 | Keller | 3,460,557 A | 8/1969 | Gallant |
| 3,187,745 A | 6/1965 | Baum et al. | 3,463,338 A | 8/1969 | Schneider |
| 3,190,388 A | 6/1965 | Moser et al. | 3,469,818 A | 9/1969 | Cowan |
| 3,205,547 A | 9/1965 | Riekse | 3,470,725 A | 10/1969 | Brown et al. |
| 3,208,255 A | 9/1965 | Burk | 3,472,230 A | 10/1969 | Fogarty |
| 3,209,570 A | 10/1965 | Hills | 3,478,344 A | 11/1969 | Schwitzgebel et al. |
| 3,221,468 A | 12/1965 | Casey | 3,482,449 A | 12/1969 | Werner |
| 3,228,703 A | 1/1966 | Wilson | 3,482,816 A | 12/1969 | Arnold |
| 3,229,684 A | 1/1966 | Nagumo et al. | 3,487,959 A | 1/1970 | Pearne et al. |
| 3,236,088 A | 2/1966 | Moller | 3,491,842 A | 1/1970 | Delacour et al. |
| 3,238,624 A | 3/1966 | McCabe | 3,492,638 A | 1/1970 | Lane |
| 3,240,510 A | 3/1966 | Spouge | 3,502,829 A | 3/1970 | Reynolds |
| 3,245,642 A | 4/1966 | Dicke | 3,503,116 A | 3/1970 | Strack |
| 3,255,568 A | 6/1966 | Martin et al. | 3,504,664 A | 4/1970 | Haddad |
| 3,260,091 A | 7/1966 | Shaw, Jr. | 3,505,808 A | 4/1970 | Eschle |
| 3,265,822 A | 8/1966 | Moulten | 3,509,754 A | 5/1970 | Massingill et al. |
| 3,266,489 A | 8/1966 | Watkins et al. | 3,512,517 A | 5/1970 | Kadish et al. |
| 3,273,447 A | 9/1966 | Frank | 3,514,919 A | 6/1970 | Ashton et al. |
| 3,283,352 A | 11/1966 | Hu | 3,516,220 A | 6/1970 | Buford et al. |
| 3,290,919 A | 12/1966 | Malinak et al. | 3,517,553 A | 6/1970 | Williams et al. |
| 3,292,493 A | 12/1966 | Franklin | 3,527,226 A | 9/1970 | Hakin et al. |
| 3,292,888 A | 12/1966 | Fischer | 3,529,908 A | 9/1970 | Smith |
| 3,294,988 A | 12/1966 | Packard | 3,530,449 A | 9/1970 | Anderson |
| 3,299,603 A | 1/1967 | Shaw | 3,533,403 A | 10/1970 | Woodson |
| 3,299,882 A | 1/1967 | Masino | 3,534,728 A | 10/1970 | Barrows |
| 3,301,514 A | 1/1967 | Sugaya | 3,534,872 A | 10/1970 | Roth et al. |
| 3,302,457 A | 2/1967 | Mayes | 3,535,914 A | 10/1970 | Veith et al. |
| 3,306,384 A | 2/1967 | Ross | 3,539,009 A | 11/1970 | Kudlaty |
| 3,313,314 A | 4/1967 | Burke et al. | 3,543,744 A | 12/1970 | LePar |
| 3,316,935 A | 5/1967 | Kaiser et al. | 3,545,275 A | 12/1970 | Harrison et al. |
| 3,320,750 A | 5/1967 | Haise et al. | 3,550,583 A | 12/1970 | Chiku |
| 3,321,035 A | 5/1967 | Tarpley | 3,550,847 A | 12/1970 | Scott |
| 3,332,788 A | 7/1967 | Barnby | 3,563,094 A | 2/1971 | Rieschel |
| 3,334,510 A | 8/1967 | Hallesy | 3,563,245 A | 2/1971 | McLean et al. |
| 3,339,401 A | 9/1967 | Peters | 3,566,083 A | 2/1971 | McMillin |
| 3,340,868 A | 9/1967 | Darling | 3,566,875 A | 3/1971 | Stoehr |
| 3,347,162 A | 10/1967 | Braznell | 3,568,367 A | 3/1971 | Myers |
| 3,350,944 A | 11/1967 | De Michele | 3,568,636 A | 3/1971 | Lockwood |
| 3,353,364 A | 11/1967 | Blanding et al. | 3,576,554 A | 4/1971 | Temps, Jr. et al |
| 3,353,481 A | 11/1967 | Antonucci | 3,580,082 A | 5/1971 | Strack |
| 3,356,334 A | 12/1967 | Scaramucci | 3,581,402 A | 6/1971 | London et al. |
| 3,356,510 A | 12/1967 | Barnby | 3,583,387 A | 6/1971 | Garner et al. |
| 3,357,218 A | 12/1967 | Mitchell | 3,587,204 A | 6/1971 | George |
| 3,357,461 A | 12/1967 | Friendship | 3,590,809 A | 7/1971 | London |
| 3,359,741 A | 12/1967 | Nelson | 3,590,818 A | 7/1971 | Lemole |
| 3,361,300 A | 1/1968 | Kaplan | 3,590,992 A | 7/1971 | Soderstrom et al. |
| 3,364,929 A | 1/1968 | Ide et al. | 3,592,183 A | 7/1971 | Watkins et al. |
| 3,365,684 A | 1/1968 | Stemke | 3,594,519 A | 7/1971 | Schmidlin |
| 3,378,456 A | 4/1968 | Roberts | 3,602,885 A | 8/1971 | Grajeda |
| 3,380,445 A | 4/1968 | Frasier | 3,610,016 A | 10/1971 | Bultman |
| 3,380,649 A | 4/1968 | Roberts | 3,610,851 A | 10/1971 | Krupski |
| 3,385,022 A | 5/1968 | Anderson | 3,611,811 A | 10/1971 | Lissau |
| 3,389,355 A | 6/1968 | Schroeder, Jr. | 3,614,926 A | 10/1971 | Brechtel |

| | | | | | | |
|---|---|---|---|---|---|---|
| 3,614,955 | A | 10/1971 | Mirowski et al. | 3,831,588 A | 8/1974 | Rindner |
| 3,619,742 | A | 11/1971 | Rud, Jr. | 3,831,942 A | 8/1974 | Del Mar |
| 3,623,371 | A | 11/1971 | Jullien-Davin | 3,833,238 A | 9/1974 | Liard et al. |
| 3,624,854 | A | 12/1971 | Strong | 3,834,167 A | 9/1974 | Tabor |
| 3,630,242 | A | 12/1971 | Schieser et al. | 3,834,739 A | 9/1974 | Abildgaard et al. |
| 3,631,847 | A | 1/1972 | Hobbs, II | 3,835,523 A | 9/1974 | Stansfield et al. |
| 3,633,881 | A | 1/1972 | Yurdin | 3,839,708 A | 10/1974 | Bredesen et al. |
| 3,635,061 | A | 1/1972 | Rydell et al. | 3,842,483 A | 10/1974 | Cramer |
| 3,635,074 | A | 1/1972 | Moos et al. | 3,842,668 A | 10/1974 | Lippke et al. |
| 3,638,496 | A | 2/1972 | King | 3,845,664 A | 11/1974 | Perry, Jr. |
| 3,644,883 | A | 2/1972 | Borman et al. | 3,845,751 A | 11/1974 | Runstetler |
| 3,648,687 | A | 3/1972 | Ramsey III | 3,845,757 A | 11/1974 | Weyer |
| 3,651,289 | A | 3/1972 | Nagashima et al. | 3,847,434 A | 11/1974 | Weman et al. |
| 3,651,405 | A | 3/1972 | Whitney et al. | 3,850,208 A | 11/1974 | Hamilton |
| 3,653,671 | A | 4/1972 | Shipes | 3,853,117 A | 12/1974 | Murr |
| 3,659,615 | A | 5/1972 | Enger | 3,854,469 A | 12/1974 | Giori et al. |
| 3,677,685 | A | 7/1972 | Aoki et al. | 3,855,902 A | 12/1974 | Kirst et al. |
| 3,686,958 | A | 8/1972 | Porter et al. | 3,857,399 A | 12/1974 | Zacouto et al. |
| 3,688,568 | A | 9/1972 | Karper et al. | 3,857,452 A | 12/1974 | Hartman |
| 3,701,392 | A | 10/1972 | Wirth et al. | 3,857,745 A | 12/1974 | Grausch et al. |
| 3,702,677 | A | 11/1972 | Heffington | 3,858,581 A | 1/1975 | Kamen |
| 3,703,099 | A | 11/1972 | Rouse et al. | 3,863,622 A | 2/1975 | Buuck |
| 3,712,138 | A | 1/1973 | Alinari et al. | 3,863,933 A | 2/1975 | Tredway |
| 3,713,124 | A | 1/1973 | Durland et al. | 3,867,950 A | 2/1975 | Fischell |
| 3,719,524 | A | 3/1973 | Ripley et al. | 3,868,008 A | 2/1975 | Brumbaugh |
| 3,721,412 | A | 3/1973 | Kindorf | 3,868,679 A | 2/1975 | Arneson |
| 3,723,247 | A | 3/1973 | Leine et al. | 3,871,599 A | 3/1975 | Takada et al. |
| 3,724,000 | A | 4/1973 | Eakman | 3,872,285 A | 3/1975 | Shum et al. |
| 3,727,463 | A | 4/1973 | Intraub | 3,874,388 A | 4/1975 | King et al. |
| 3,727,615 | A | 4/1973 | Lenzkes | 3,876,980 A | 4/1975 | Haemmig et al. |
| 3,730,174 | A | 5/1973 | Madison | 3,878,908 A | 4/1975 | Andersson et al. |
| 3,730,560 | A | 5/1973 | Abildgaard et al. | 3,881,528 A | 5/1975 | Mackenzie |
| 3,731,679 | A | 5/1973 | Wilhelmson et al. | 3,886,948 A | 6/1975 | Hakim et al. |
| 3,731,681 | A | 5/1973 | Blackshear et al. | 3,893,111 A | 7/1975 | Cotter |
| 3,732,731 | A | 5/1973 | Fussell Jr. | 3,893,451 A | 7/1975 | Durand et al. |
| 3,735,040 | A | 5/1973 | Punt et al. | 3,895,681 A | 7/1975 | Griffin et al. |
| 3,736,930 | A | 6/1973 | Georgi | 3,899,862 A | 8/1975 | Muys et al. |
| 3,738,356 | A | 6/1973 | Workman | 3,904,234 A | 9/1975 | Hill et al. |
| 3,740,921 | A | 6/1973 | Meyer et al. | 3,908,334 A | 9/1975 | Rychiger et al. |
| 3,746,111 | A | 7/1973 | Berthiaume et al. | 3,908,461 A | 9/1975 | Turpen |
| 3,748,678 | A | 7/1973 | Ballou | 3,908,721 A | 9/1975 | McGahey et al. |
| 3,749,098 | A | 7/1973 | De Bennetot et al. | 3,910,087 A | 10/1975 | Jones |
| 3,749,422 | A | 7/1973 | Abildgaard et al. | 3,912,168 A | 10/1975 | Mullins et al. |
| 3,749,423 | A | 7/1973 | Abildgaard et al. | 3,912,304 A | 10/1975 | Abildgaard et al. |
| 3,750,194 | A | 8/1973 | Summers | 3,918,286 A | 11/1975 | Whitehead |
| 3,757,770 | A | 9/1973 | Brayshaw et al. | 3,918,291 A | 11/1975 | Pauly et al. |
| 3,759,095 | A | 9/1973 | Short, Jr. et al. | 3,920,965 A | 11/1975 | Sohrwardy et al. |
| 3,760,638 | A | 9/1973 | Lawson et al. | 3,921,682 A | 11/1975 | McGahey et al. |
| 3,763,960 | A | 10/1973 | John et al. | 3,922,951 A | 12/1975 | Linsinger et al. |
| 3,765,142 | A | 10/1973 | Lindquist et al. | 3,923,060 A | 12/1975 | Ellinwood, Jr. |
| 3,765,494 | A | 10/1973 | Kielman, Jr. | 3,924,635 A | 12/1975 | Hakim et al. |
| 3,769,156 | A | 10/1973 | Brecy et al. | 3,928,980 A | 12/1975 | Ganzinotti et al. |
| 3,769,830 | A | 11/1973 | Porter et al. | 3,929,175 A | 12/1975 | Coone |
| 3,774,243 | A | 11/1973 | Ny et al. | 3,930,682 A | 1/1976 | Booth |
| 3,776,333 | A | 12/1973 | Mathauser | 3,930,852 A | 1/1976 | Tanaka et al. |
| 3,778,051 | A | 12/1973 | Allen et al. | 3,936,028 A | 2/1976 | Norton et al. |
| 3,780,578 | A | 12/1973 | Sellman et al. | 3,939,823 A | 2/1976 | Kaye et al. |
| 3,781,902 | A | 12/1973 | Shim et al. | 3,940,122 A | 2/1976 | Janzen et al. |
| 3,783,585 | A | 1/1974 | Hoyland et al. | 3,940,630 A | 2/1976 | Bergonz |
| 3,789,667 | A | 2/1974 | Porter et al. | 3,942,299 A | 3/1976 | Bory et al. |
| 3,796,095 | A | 3/1974 | Fussell, Jr. | 3,942,382 A | 3/1976 | Hok et al. |
| 3,807,219 | A | 4/1974 | Wallskog | 3,942,536 A | 3/1976 | Mirowski et al. |
| 3,811,429 | A | 5/1974 | Fletcher et al. | 3,943,915 A | 3/1976 | Severson |
| 3,815,722 | A | 6/1974 | Sessoms | 3,945,704 A | 3/1976 | Kraus et al. |
| 3,818,765 | A | 6/1974 | Eriksen et al. | 3,946,613 A | 3/1976 | Silver |
| 3,820,400 | A | 6/1974 | Russo | 3,946,615 A | 3/1976 | Hluchan |
| 3,820,795 | A | 6/1974 | Taylor | 3,946,724 A | 3/1976 | La Balme et al. |
| 3,823,610 | A | 7/1974 | Fussell, Jr. | 3,948,141 A | 4/1976 | Shinjo et al. |
| 3,825,065 | A | 7/1974 | Lloyd et al. | 3,949,388 A | 4/1976 | Fuller |
| 3,825,963 | A | 7/1974 | Abildgaard et al. | 3,953,289 A | 4/1976 | Costes et al. |
| 3,825,964 | A | 7/1974 | Groswith III et al. | 3,954,271 A | 5/1976 | Tredway, Sr. |
| 3,828,672 | A | 8/1974 | Gazzola et al. | 3,958,558 A | 5/1976 | Dunphy et al. |
| 3,828,766 | A | 8/1974 | Krasnow | 3,960,142 A | 6/1976 | Elliott et al. |

| | | | | | | |
|---|---|---|---|---|---|---|
| 3,961,425 A | 6/1976 | Swanson et al. | | 4,077,394 A | 3/1978 | McCurdy |
| 3,961,646 A | 6/1976 | Schon et al. | | 4,077,405 A | 3/1978 | Haerten et al. |
| 3,962,895 A | 6/1976 | Rydell | | 4,077,882 A | 3/1978 | Gangemi |
| 3,962,921 A | 6/1976 | Lips | | 4,078,620 A | 3/1978 | Westlake et al. |
| 3,963,019 A | 6/1976 | Quandt | | 4,080,653 A | 3/1978 | Barnes, Jr. et al. |
| 3,964,485 A | 6/1976 | Neumeier | | 4,084,752 A | 4/1978 | Hagiwara et al. |
| 3,964,770 A | 6/1976 | Abildgaard et al. | | 4,086,488 A | 4/1978 | Hill |
| 3,967,737 A | 7/1976 | Peralta et al. | | 4,087,568 A | 5/1978 | Fay et al. |
| 3,968,473 A | 7/1976 | Patton et al. | | 4,088,417 A | 5/1978 | Kosmowski |
| 3,968,594 A | 7/1976 | Kawakami | | 4,089,329 A | 5/1978 | Couvillon, Jr. et al. |
| 3,972,320 A | 8/1976 | Kalman | | 4,090,802 A | 5/1978 | Bilz et al. |
| 3,973,753 A | 8/1976 | Wheeler | | 4,092,719 A | 5/1978 | Salmon et al. |
| 3,973,858 A | 8/1976 | Poisson et al. | | 4,092,925 A | 6/1978 | Fromson |
| 3,974,655 A | 8/1976 | Halpern et al. | | 4,096,866 A | 6/1978 | Fischell |
| 3,974,865 A | 8/1976 | Fenton et al. | | 4,098,293 A | 7/1978 | Kramer et al. |
| 3,976,278 A | 8/1976 | Dye et al. | | 4,103,496 A | 8/1978 | Colamussi et al. |
| 3,977,391 A | 8/1976 | Fleischmann | | 4,106,370 A | 8/1978 | Kraus et al. |
| 3,980,871 A | 9/1976 | Lindstrom et al. | | 4,107,689 A | 8/1978 | Jellinek |
| 3,982,571 A | 9/1976 | Fenton et al. | | 4,107,995 A | 8/1978 | Ligman et al. |
| 4,114,603 A | 9/1976 | Wilkinson | | 4,108,148 A | 8/1978 | Cannon, III |
| 3,983,948 A | 10/1976 | Jeter | | 4,108,575 A | 8/1978 | Schal et al. |
| 3,985,133 A | 10/1976 | Jenkins et al. | | 4,109,148 A | 8/1978 | Jaulmes et al. |
| 3,987,860 A | 10/1976 | Jabsen | | 4,109,518 A | 8/1978 | Dooley et al. |
| 3,989,005 A | 11/1976 | Bowler, Jr. et al. | | 4,109,644 A | 8/1978 | Kojima |
| 3,991,749 A | 11/1976 | Zent | | 4,111,056 A | 9/1978 | Mastromatteo |
| 3,992,948 A | 11/1976 | D'Antonio et al. | | 4,111,629 A | 9/1978 | Nussbaumer et al. |
| 3,993,149 A | 11/1976 | Harvey | | 4,114,424 A | 9/1978 | Johnson |
| 3,996,927 A | 12/1976 | Frank | | 4,114,606 A | 9/1978 | Seylar |
| 3,996,962 A | 12/1976 | Sutherland | | 4,120,097 A | 10/1978 | Jeter |
| 4,003,141 A | 1/1977 | Le Roy | | 4,120,134 A | 10/1978 | Scholle |
| 4,005,282 A | 1/1977 | Jennings | | 4,121,635 A | 10/1978 | Hansel |
| 4,005,593 A | 2/1977 | Goldberg | | 4,123,310 A | 10/1978 | Varon et al. |
| 4,006,735 A | 2/1977 | Hittman et al. | | 4,124,023 A | 11/1978 | Fleischmann et al. |
| 4,009,591 A | 3/1977 | Hester | | 4,127,110 A | 11/1978 | Bullara |
| 4,010,449 A | 3/1977 | Faggin et al. | | 4,130,169 A | 12/1978 | Denison |
| 4,014,319 A | 3/1977 | Favre et al. | | 4,131,596 A | 12/1978 | Allen |
| 4,014,321 A | 3/1977 | March | | 4,133,355 A | 1/1979 | Mayer |
| 4,016,764 A | 4/1977 | Rice | | 4,133,367 A | 1/1979 | Abell |
| 4,017,329 A | 4/1977 | Larson | | 4,135,509 A | 1/1979 | Shannon |
| 4,018,134 A | 4/1977 | Linsinger et al. | | 4,140,131 A | 2/1979 | Dutcher et al. |
| 4,022,190 A | 5/1977 | Meyer | | 4,141,348 A | 2/1979 | Hittman |
| 4,024,864 A | 5/1977 | Davies et al. | | 4,141,349 A | 2/1979 | Ory et al. |
| 4,025,912 A | 5/1977 | Rice | | 4,143,661 A | 3/1979 | LaForge et al. |
| 4,026,276 A | 5/1977 | Chubbuck | | 4,146,029 A | 3/1979 | Ellinwood, Jr. |
| 4,027,661 A | 6/1977 | Lyon et al. | | 4,147,161 A | 4/1979 | Ikebe et al. |
| 4,031,899 A | 6/1977 | Renirie et al. | | 4,148,096 A | 4/1979 | Haas et al. |
| 4,036,775 A | 7/1977 | Trautvetter et al. | | 4,149,423 A | 4/1979 | Frosch et al. |
| 4,039,069 A | 8/1977 | Kwan et al. | | 4,151,823 A | 5/1979 | Grosse et al. |
| 4,041,954 A | 8/1977 | Ohara et al. | | 4,153,085 A | 5/1979 | Adams |
| 4,042,504 A | 8/1977 | Drori et al. | | 4,156,422 A | 5/1979 | Hildebrandt et al. |
| 4,045,345 A | 8/1977 | Drori et al. | | 4,160,448 A | 7/1979 | Jackson |
| 4,047,296 A | 9/1977 | Ishida et al. | | 4,160,971 A | 7/1979 | Jones et al. |
| 4,047,851 A | 9/1977 | Bender | | 4,166,469 A | 9/1979 | Littleford |
| 4,048,494 A | 9/1977 | Liesting et al. | | 4,167,304 A | 9/1979 | Gelbke |
| 4,048,879 A | 9/1977 | Cox | | 4,167,952 A | 9/1979 | Reinicke |
| 4,049,004 A | 9/1977 | Walters | | 4,168,567 A | 9/1979 | Leguy et al. |
| 4,051,338 A | 9/1977 | Harris, III | | 4,170,280 A | 10/1979 | Schwarz |
| 4,052,991 A | 10/1977 | Zacouto et al. | | 4,171,218 A | 10/1979 | Hoshino et al. |
| 4,055,074 A | 10/1977 | Thimons et al. | | 4,173,228 A | 11/1979 | Van Steenwyk et al. |
| 4,055,175 A | 10/1977 | Clemens et al. | | 4,183,124 A | 1/1980 | Hoffman |
| 4,056,854 A | 11/1977 | Boretos et al. | | 4,183,247 A | 1/1980 | Allen et al. |
| 4,058,007 A | 11/1977 | Exner et al. | | 4,185,641 A | 1/1980 | Minior et al. |
| 4,062,351 A | 12/1977 | Hastwell et al. | | 4,186,287 A | 1/1980 | Scott |
| 4,062,354 A | 12/1977 | Taylor et al. | | 4,186,749 A | 2/1980 | Fryer |
| 4,062,360 A | 12/1977 | Bentley | | 4,186,751 A | 2/1980 | Fleischmann |
| 4,063,439 A | 12/1977 | Besson et al. | | 4,190,057 A | 2/1980 | Hill et al. |
| 4,064,882 A | 12/1977 | Johnson et al. | | 4,191,004 A | 3/1980 | Gmuer et al. |
| 4,070,239 A | 1/1978 | Bevilacqua | | 4,191,187 A | 3/1980 | Wright et al. |
| 4,072,047 A | 2/1978 | Reismuller et al. | | 4,192,192 A | 3/1980 | Schnell |
| 4,073,292 A | 2/1978 | Edelman | | 4,193,397 A | 3/1980 | Tucker et al. |
| 4,075,099 A | 2/1978 | Pelton et al. | | 4,204,547 A | 5/1980 | Allocca |
| 4,075,602 A | 2/1978 | Clothier | | 4,206,755 A | 6/1980 | Klein et al. |
| 4,077,072 A | 3/1978 | Dezura et al. | | 4,206,761 A | 6/1980 | Cosman |

| | | | | | |
|---|---|---|---|---|---|
| 4,206,762 A | 6/1980 | Cosman | 4,378,809 A | 4/1983 | Cosman |
| 4,207,903 A | 6/1980 | O'Neill | 4,380,427 A | 4/1983 | Hehl et al. |
| 4,212,074 A | 7/1980 | Kuno et al. | 4,385,636 A | 5/1983 | Cosman |
| 4,217,221 A | 8/1980 | Masso | 4,386,422 A | 5/1983 | Mumby et al. |
| 4,217,588 A | 8/1980 | Freeny, Jr. | 4,387,715 A | 6/1983 | Hakim et al. |
| 4,220,189 A | 9/1980 | Marquez | 4,387,907 A | 6/1983 | Hiestand et al. |
| 4,221,219 A | 9/1980 | Tucker | 4,392,368 A | 7/1983 | Folkesson et al. |
| 4,221,523 A | 9/1980 | Eberle | 4,393,899 A | 7/1983 | Tsuji et al. |
| 4,223,837 A | 9/1980 | Gubbiotti et al. | 4,393,951 A | 7/1983 | Horst-Rudolf et al. |
| 4,226,124 A | 10/1980 | Kersten et al. | 4,395,232 A | 7/1983 | Koch |
| 4,226,229 A | 10/1980 | Eckhart et al. | 4,395,258 A | 7/1983 | Wang et al. |
| 4,227,533 A | 10/1980 | Godfrey | 4,395,916 A | 8/1983 | Martin |
| 4,231,376 A | 11/1980 | Lyon et al. | 4,398,983 A | 8/1983 | Suzuki et al. |
| 4,232,682 A | 11/1980 | Veth | 4,399,705 A | 8/1983 | Weiger et al. |
| 4,237,900 A | 12/1980 | Schulman et al. | 4,399,707 A | 8/1983 | Wamstad |
| 4,241,247 A | 12/1980 | Byrne et al. | 4,399,809 A | 8/1983 | Baro et al. |
| 4,241,870 A | 12/1980 | Marcus | 4,399,821 A | 8/1983 | Bowers |
| 4,245,593 A | 1/1981 | Stein | 4,403,984 A | 9/1983 | Ash et al. |
| 4,246,877 A | 1/1981 | Kennedy | 4,404,968 A | 9/1983 | Evans, Sr. |
| 4,247,850 A | 1/1981 | Marcus | 4,404,974 A | 9/1983 | Titus |
| 4,248,238 A | 2/1981 | Joseph et al. | 4,405,318 A | 9/1983 | Whitney et al. |
| 4,248,241 A | 2/1981 | Tacchi | 4,407,125 A | 10/1983 | Parsons et al. |
| 4,256,094 A | 3/1981 | Kapp et al. | 4,407,271 A | 10/1983 | Schiff |
| 4,256,118 A | 3/1981 | Nagel et al. | 4,407,296 A | 10/1983 | Anderson |
| 4,262,343 A | 4/1981 | Claycomb | 4,407,326 A | 10/1983 | Wilhelm |
| 4,262,632 A | 4/1981 | Hanton et al. | 4,408,597 A | 10/1983 | Tenney, Jr. |
| 4,265,241 A | 5/1981 | Portner et al. | 4,415,071 A | 11/1983 | Butler et al. |
| 4,265,252 A | 5/1981 | Chubbuck et al. | 4,416,282 A | 11/1983 | Saulson et al. |
| 4,271,018 A | 6/1981 | Drori et al. | 4,418,899 A | 12/1983 | Zimmermann et al. |
| 4,273,070 A | 6/1981 | Hoefelmayr et al. | 4,419,393 A | 12/1983 | Hanson et al. |
| 4,274,444 A | 6/1981 | Ruyak | 4,421,124 A | 12/1983 | Marshall |
| 4,275,600 A | 6/1981 | Turner et al. | 4,421,505 A | 12/1983 | Schwartz |
| 4,275,913 A | 6/1981 | Marcus | 4,424,720 A | 1/1984 | Bucchianeri |
| 4,278,540 A | 7/1981 | Drori et al. | 4,428,228 A | 1/1984 | Banzhaf et al. |
| 4,280,036 A | 7/1981 | Fukatsu et al. | 4,428,365 A | 1/1984 | Hakky et al. |
| 4,280,775 A | 7/1981 | Wood | 4,430,899 A | 2/1984 | Wessel et al. |
| 4,281,666 A | 8/1981 | Cosman | 4,431,009 A | 2/1984 | Marino, Jr. et al. |
| 4,281,667 A | 8/1981 | Cosman | 4,431,365 A | 2/1984 | Sturtz, Jr. |
| 4,284,073 A | 8/1981 | Krause et al. | 4,432,363 A | 2/1984 | Kakegawa et al. |
| 4,285,770 A | 8/1981 | Chi et al. | 4,435,173 A | 3/1984 | Siposs et al. |
| 4,291,699 A | 9/1981 | Geddes et al. | 4,439,186 A | 3/1984 | Kuhl et al. |
| 4,295,963 A | 10/1981 | Drori et al. | 4,441,491 A | 4/1984 | Evans, Sr. |
| 4,297,927 A | 11/1981 | Kuroda et al. | 4,441,501 A | 4/1984 | Parent |
| 4,303,075 A | 12/1981 | Heilman et al. | 4,444,194 A | 4/1984 | Burcham |
| 4,305,402 A | 12/1981 | Katims | 4,444,498 A | 4/1984 | Heinemann |
| 4,312,374 A | 1/1982 | Drori et al. | 4,445,385 A | 5/1984 | Endo |
| 4,314,480 A | 2/1982 | Becker | 4,446,711 A | 5/1984 | Valente |
| 4,316,693 A | 2/1982 | Baxter et al. | 4,447,224 A | 5/1984 | DeCant, Jr. et al. |
| 4,325,387 A | 4/1982 | Helfer | 4,449,493 A | 5/1984 | Kopec et al. |
| 4,327,804 A | 5/1982 | Reed | 4,450,811 A | 5/1984 | Ichikawa et al. |
| 4,328,654 A | 5/1982 | Van Ginkel et al. | 4,450,946 A | 5/1984 | Olding et al. |
| 4,332,254 A | 6/1982 | Lundquist | 4,451,033 A | 5/1984 | Nestegard |
| 4,332,255 A | 6/1982 | Hakim et al. | 4,453,537 A | 6/1984 | Spitzer |
| 4,339,831 A | 7/1982 | Johnson | 4,453,578 A | 6/1984 | Wilder |
| 4,342,218 A | 8/1982 | Fox | 4,460,835 A | 7/1984 | Masuoka et al. |
| 4,342,308 A | 8/1982 | Trick | 4,464,170 A | 8/1984 | Clemens et al. |
| 4,346,604 A | 8/1982 | Snook et al. | 4,465,015 A | 8/1984 | Osta et al. |
| 4,347,851 A | 9/1982 | Jundaniam | 4,465,474 A | 8/1984 | Mardorf et al. |
| 4,350,647 A | 9/1982 | de la Cruz | 4,466,290 A | 8/1984 | Frick |
| 4,350,970 A | 9/1982 | von Tomkewitsch et al. | 4,468,172 A | 8/1984 | Dixon et al. |
| 4,351,037 A | 9/1982 | Scherbatskoy | 4,468,762 A | 8/1984 | Jurgens et al. |
| 4,351,116 A | 9/1982 | Scott, Jr. | 4,469,365 A | 9/1984 | Marcus et al. |
| 4,356,486 A | 10/1982 | Mount | 4,471,182 A | 9/1984 | Wielgos et al. |
| 4,360,010 A | 11/1982 | Finney | 4,471,786 A | 9/1984 | Inagaki et al. |
| 4,360,277 A | 11/1982 | Daniel et al. | 4,473,067 A | 9/1984 | Schiff |
| 4,361,153 A | 11/1982 | Slocum et al. | 4,473,078 A | 9/1984 | Angel |
| 4,363,236 A | 12/1982 | Meyers | 4,476,721 A | 10/1984 | Hochreuther et al. |
| 4,364,276 A | 12/1982 | Schimazoe et al. | 4,478,213 A | 10/1984 | Redding |
| 4,365,425 A | 12/1982 | Gotchel | 4,478,538 A | 10/1984 | Kakino et al. |
| 4,368,937 A | 1/1983 | Palombo et al. | 4,483,196 A | 11/1984 | Kurtz et al. |
| 4,369,013 A | 1/1983 | Abildgaard et al. | 4,484,135 A | 11/1984 | Ishihara et al. |
| 4,373,527 A | 2/1983 | Fischell | 4,485,813 A | 12/1984 | Anderson et al. |
| 4,376,523 A | 3/1983 | Goyen et al. | 4,489,916 A | 12/1984 | Stevens |

| | | | | | |
|---|---|---|---|---|---|
| 4,492,632 A | 1/1985 | Mattson | 4,610,256 A | 9/1986 | Wallace |
| 4,494,411 A | 1/1985 | Koschke et al. | 4,614,137 A | 9/1986 | Jones |
| 4,494,950 A | 1/1985 | Fischell | 4,615,691 A | 10/1986 | Hakim et al. |
| 4,497,176 A | 2/1985 | Rubin et al. | 4,617,016 A | 10/1986 | Blomberg et al. |
| 4,497,201 A | 2/1985 | Allen et al. | 4,618,861 A | 10/1986 | Gettens et al. |
| 4,499,394 A | 2/1985 | Koal | 4,620,807 A | 11/1986 | Polit |
| 4,499,691 A | 2/1985 | Karazim et al. | 4,621,331 A | 11/1986 | Iwata et al. |
| 4,499,750 A | 2/1985 | Gerber et al. | 4,622,871 A | 11/1986 | Van Sickle et al. |
| 4,503,678 A | 3/1985 | Wimbush et al. | 4,626,462 A | 12/1986 | Kober et al. |
| 4,511,974 A | 4/1985 | Nakane et al. | 4,633,304 A | 12/1986 | Nagasaki et al. |
| 4,513,295 A | 4/1985 | Jones et al. | 4,633,878 A | 1/1987 | Bombardieri et al. |
| 4,515,004 A | 5/1985 | Jaenson | 4,635,182 A | 1/1987 | Hintz |
| 4,515,750 A | 5/1985 | Pardini et al. | 4,637,736 A | 1/1987 | Andeen et al. |
| 4,516,866 A | 5/1985 | Yamauchi et al. | 4,638,665 A | 1/1987 | Benson et al. |
| 4,518,637 A | 5/1985 | Takeda et al. | 4,644,246 A | 2/1987 | Knapen et al. |
| 4,519,401 A | 5/1985 | Ko et al. | 4,646,553 A | 3/1987 | Tufte et al. |
| 4,520,443 A | 5/1985 | Yuki et al. | 4,648,363 A | 3/1987 | Kronich |
| 4,522,213 A | 6/1985 | Wallroth et al. | 4,648,406 A | 3/1987 | Miller |
| 4,527,568 A | 7/1985 | Rickards et al. | 4,658,358 A | 4/1987 | Leach et al. |
| 4,529,401 A | 7/1985 | Leslie et al. | 4,658,760 A | 4/1987 | Zehuhr |
| 4,531,526 A | 7/1985 | Genest | 4,660,568 A | 4/1987 | Cosman |
| 4,531,936 A | 7/1985 | Gordon | 4,665,511 A | 5/1987 | Rodney et al. |
| 4,536,000 A | 8/1985 | Rohm et al. | 4,665,896 A | 5/1987 | LaForge et al. |
| 4,537,005 A | 8/1985 | Hoyland et al. | 4,669,484 A | 6/1987 | Masters |
| 4,537,129 A | 8/1985 | Heinemann et al. | 4,672,974 A | 6/1987 | Lee |
| 4,538,616 A | 9/1985 | Rogoff | 4,674,457 A | 6/1987 | Berger et al. |
| 4,540,404 A | 9/1985 | Wolvek | 4,674,546 A | 6/1987 | Fournier et al. |
| 4,542,461 A | 9/1985 | Eldridge et al. | 4,678,408 A | 7/1987 | Nason et al. |
| 4,544,369 A | 10/1985 | Skakoon et al. | 4,681,559 A | 7/1987 | Hooven |
| 4,545,185 A | 10/1985 | Chikatani et al. | 4,683,850 A | 8/1987 | Bauder et al. |
| 4,546,524 A | 10/1985 | Kreft | 4,685,463 A | 8/1987 | Williams |
| 4,548,209 A | 10/1985 | Wielders et al. | 4,685,469 A | 8/1987 | Keller et al. |
| 4,551,128 A | 11/1985 | Hakim et al. | 4,685,903 A | 8/1987 | Cable et al. |
| 4,552,150 A | 11/1985 | Zacouto et al. | 4,686,987 A | 8/1987 | Salo et al. |
| 4,553,226 A | 11/1985 | Scherbatskoy | 4,687,530 A | 8/1987 | Berscheid et al. |
| 4,556,063 A | 12/1985 | Thompson et al. | 4,689,979 A | 8/1987 | Salo et al. |
| 4,556,086 A | 12/1985 | Raines | 4,691,694 A | 9/1987 | Boyd et al. |
| 4,557,269 A | 12/1985 | Reynolds et al. | 4,691,710 A | 9/1987 | Dickens et al. |
| 4,557,332 A | 12/1985 | Denison et al. | 4,693,253 A | 9/1987 | Adams |
| 4,559,815 A | 12/1985 | Needham et al. | 4,695,237 A | 9/1987 | Inaba et al. |
| 4,560,979 A | 12/1985 | Rosskopf et al. | 4,696,189 A | 9/1987 | Hochreuther et al. |
| 4,561,442 A | 12/1985 | Vollmann et al. | 4,697,574 A | 10/1987 | Karcher et al. |
| 4,562,751 A | 1/1986 | Nason et al. | 4,698,038 A | 10/1987 | Key et al. |
| 4,563,175 A | 1/1986 | LaFond | 4,700,497 A | 10/1987 | Sato et al. |
| 4,565,116 A | 1/1986 | Hehl et al. | 4,700,610 A | 10/1987 | Bauer et al. |
| 4,566,456 A | 1/1986 | Koning et al. | 4,701,143 A | 10/1987 | Key et al. |
| 4,569,623 A | 2/1986 | Goldmann | 4,703,756 A | 11/1987 | Gough et al. |
| 4,570,351 A | 2/1986 | Szanto et al. | 4,705,507 A | 11/1987 | Boyles |
| 4,571,161 A | 2/1986 | Leblanc et al. | 4,706,948 A | 11/1987 | Kroecher et al. |
| 4,571,749 A | 2/1986 | Fischell | 4,711,249 A | 12/1987 | Brooks |
| 4,571,995 A | 2/1986 | Timme | 4,712,562 A | 12/1987 | Ohayon et al. |
| 4,573,835 A | 3/1986 | Eckardt et al. | 4,718,425 A | 1/1988 | Tanaka et al. |
| 4,574,792 A | 3/1986 | Trick | 4,722,348 A | 2/1988 | Ligtenberg et al. |
| 4,576,181 A | 3/1986 | Wallace et al. | 4,724,806 A | 2/1988 | Hartwig et al. |
| 4,576,183 A | 3/1986 | Plicchi et al. | 4,724,830 A | 2/1988 | Fischell |
| 4,577,512 A | 3/1986 | Lowenheck et al. | 4,725,826 A | 2/1988 | Hunter |
| 4,581,018 A | 4/1986 | Jassawalla et al. | 4,727,887 A | 3/1988 | Haber |
| 4,581,915 A | 4/1986 | Haulsee et al. | 4,728,479 A | 3/1988 | Merkovsky |
| 4,587,840 A | 5/1986 | Dobler et al. | 4,729,517 A | 3/1988 | Krokor et al. |
| 4,589,805 A | 5/1986 | Duffner et al. | 4,730,188 A | 3/1988 | Milheiser |
| 4,592,339 A | 6/1986 | Kuzmak et al. | 4,730,420 A | 3/1988 | Stratmann et al. |
| 4,592,340 A | 6/1986 | Boyles | 4,730,619 A | 3/1988 | Koning et al. |
| 4,593,703 A | 6/1986 | Cosman | 4,731,058 A | 3/1988 | Doan |
| 4,595,228 A | 6/1986 | Chu | 4,735,205 A | 4/1988 | Chachques et al. |
| 4,595,390 A | 6/1986 | Hakim et al. | 4,738,267 A | 4/1988 | Lazorthes et al. |
| 4,596,563 A | 6/1986 | Pande | 4,738,268 A | 4/1988 | Kipnis |
| 4,599,943 A | 7/1986 | Kobler et al. | 4,741,345 A | 5/1988 | Matthews et al. |
| 4,600,855 A | 7/1986 | Strachan et al. | 4,741,732 A | 5/1988 | Crankshaw et al. |
| 4,602,541 A | 7/1986 | Benzinger et al. | 4,743,129 A | 5/1988 | Keryhuel et al. |
| 4,604,089 A | 8/1986 | Santangelo et al. | 4,745,541 A | 5/1988 | Vaniglia et al. |
| 4,605,354 A | 8/1986 | Daly | 4,746,830 A | 5/1988 | Holland |
| 4,606,419 A | 8/1986 | Perini | 4,750,495 A | 6/1988 | Moore et al. |
| 4,606,478 A | 8/1986 | Hack et al. | 4,752,115 A | 6/1988 | Murray, Jr. et al. |

| | | |
|---|---|---|
| 4,752,658 A | 6/1988 | Mack |
| 4,757,463 A | 7/1988 | Ballou et al. |
| 4,759,386 A | 7/1988 | Grouw, III |
| 4,763,649 A | 8/1988 | Merrick |
| 4,765,001 A | 8/1988 | Smith |
| 4,767,406 A | 8/1988 | Wadham et al. |
| 4,769,001 A | 9/1988 | Prince |
| 4,772,257 A | 9/1988 | Hakim et al. |
| 4,772,896 A | 9/1988 | Nakatsu et al. |
| 4,773,401 A | 9/1988 | Citak et al. |
| 4,774,950 A | 10/1988 | Cohen |
| 4,774,955 A | 10/1988 | Jones |
| 4,777,953 A | 10/1988 | Ash et al. |
| 4,779,626 A | 10/1988 | Peel et al. |
| 4,781,192 A | 11/1988 | Demer |
| 4,782,826 A | 11/1988 | Fogarty |
| 4,783,106 A | 11/1988 | Nutter |
| 4,785,822 A | 11/1988 | Wallace |
| 4,788,847 A | 12/1988 | Sterghos |
| 4,791,318 A | 12/1988 | Lewis et al. |
| 4,794,803 A | 1/1989 | Osterhout et al. |
| 4,796,641 A | 1/1989 | Mills et al. |
| 4,798,211 A | 1/1989 | Goor et al. |
| 4,798,227 A | 1/1989 | Goodwin |
| 4,799,491 A | 1/1989 | Eckerle |
| 4,799,625 A | 1/1989 | Weaver, Jr. et al. |
| 4,802,488 A | 2/1989 | Eckerle |
| 4,803,987 A | 2/1989 | Calfee et al. |
| 4,804,368 A | 2/1989 | Skakoon et al. |
| 4,807,321 A | 2/1989 | Grasselli et al. |
| 4,808,167 A | 2/1989 | Mann et al. |
| 4,812,823 A | 3/1989 | Dickerson |
| 4,819,656 A | 4/1989 | Spector |
| 4,820,265 A | 4/1989 | DeSatnick et al. |
| 4,820,953 A | 4/1989 | Saubolle et al. |
| 4,821,167 A | 4/1989 | Wiebe |
| 4,821,723 A | 4/1989 | Baker, Jr. et al. |
| 4,823,779 A | 4/1989 | Daly et al. |
| 4,830,006 A | 5/1989 | Haluska et al. |
| 4,832,034 A | 5/1989 | Pizziconi et al. |
| 4,833,384 A | 5/1989 | Munro et al. |
| 4,834,731 A | 5/1989 | Nowak et al. |
| 4,838,857 A | 6/1989 | Strowe et al. |
| 4,840,068 A | 6/1989 | Mayhew, Jr. |
| 4,840,350 A | 6/1989 | Cook et al. |
| 4,844,002 A | 7/1989 | Yasui et al. |
| 4,846,153 A | 7/1989 | Berci |
| 4,846,191 A | 7/1989 | Brockway et al. |
| 4,846,664 A | 7/1989 | Hehl et al. |
| 4,854,328 A | 8/1989 | Pollack |
| 4,863,470 A | 9/1989 | Carter |
| 4,865,587 A | 9/1989 | Walling |
| 4,867,160 A | 9/1989 | Schaldach et al. |
| 4,867,498 A | 9/1989 | Delphia et al. |
| 4,867,618 A | 9/1989 | Brohammer |
| 4,869,252 A | 9/1989 | Gilli |
| 4,870,258 A | 9/1989 | Mochizuki et al. |
| 4,871,351 A | 10/1989 | Feingold et al. |
| 4,872,483 A | 10/1989 | Shah |
| 4,872,869 A | 10/1989 | Johns |
| 4,873,677 A | 10/1989 | Sakamoto et al. |
| 4,875,483 A | 10/1989 | Vollmann et al. |
| 4,880,004 A | 11/1989 | Baker, Jr. et al. |
| 4,882,678 A | 11/1989 | Hollis et al. |
| 4,886,392 A | 12/1989 | Iio et al. |
| 4,893,630 A | 1/1990 | Bray, Jr. |
| 4,895,151 A | 1/1990 | Grevis et al. |
| 4,896,594 A | 1/1990 | Baur et al. |
| 4,898,158 A | 2/1990 | Daly et al. |
| 4,898,578 A | 2/1990 | Rubalcaba, Jr. |
| 4,899,751 A | 2/1990 | Cohen |
| 4,899,752 A | 2/1990 | Cohen |
| 4,902,277 A | 2/1990 | Mathies et al. |
| 4,903,701 A | 2/1990 | Moore et al. |
| 4,905,698 A | 3/1990 | Strohl, Jr. et al. |
| 4,909,678 A | 3/1990 | Kakimoto et al. |
| 4,913,147 A | 4/1990 | Fahlstrom et al. |
| 4,919,143 A | 4/1990 | Ayers |
| 4,924,872 A | 5/1990 | Frank |
| 4,926,903 A | 5/1990 | Kawai et al. |
| 4,932,406 A | 6/1990 | Berkovits |
| 4,934,369 A | 6/1990 | Maxwell |
| 4,936,304 A | 6/1990 | Kresh et al. |
| 4,940,037 A | 7/1990 | Eckert et al. |
| 4,941,718 A | 7/1990 | Alexander, III et al. |
| 4,942,004 A | 7/1990 | Catanzaro |
| 4,944,050 A | 7/1990 | Shames et al. |
| 4,944,298 A | 7/1990 | Sholder |
| 4,944,307 A | 7/1990 | Hon et al. |
| 4,945,761 A | 8/1990 | Lessi et al. |
| 4,949,724 A | 8/1990 | Mahutte et al. |
| 4,952,205 A | 8/1990 | Mauerer et al. |
| 4,952,928 A | 8/1990 | Carroll et al. |
| 4,953,563 A | 9/1990 | Kaiser et al. |
| 4,954,677 A | 9/1990 | Alberter et al. |
| 4,958,630 A | 9/1990 | Rosenbluth et al. |
| 4,958,645 A | 9/1990 | Cadell et al. |
| 4,960,424 A | 10/1990 | Grooters |
| 4,960,966 A | 10/1990 | Evans et al. |
| 4,967,585 A | 11/1990 | Grimaldo |
| 4,967,761 A | 11/1990 | Nathanielsz |
| 4,970,823 A | 11/1990 | Chen et al. |
| 4,971,251 A | 11/1990 | Dobrick et al. |
| 4,977,896 A | 12/1990 | Robinson et al. |
| 4,978,335 A | 12/1990 | Arthur, III |
| 4,978,338 A | 12/1990 | Melsky et al. |
| 4,979,730 A | 12/1990 | Holbrook et al. |
| 4,980,671 A | 12/1990 | McCurdy |
| 4,981,141 A | 1/1991 | Segalowitz |
| 4,981,173 A | 1/1991 | Perkins et al. |
| 4,981,426 A | 1/1991 | Aoki et al. |
| 4,987,897 A | 1/1991 | Funke et al. |
| 4,988,337 A | 1/1991 | Ito et al. |
| 4,992,794 A | 2/1991 | Brouwers et al. |
| 4,997,556 A | 3/1991 | Yano et al. |
| 5,001,528 A | 3/1991 | Bahraman |
| 5,003,807 A | 4/1991 | Terrell et al. |
| 5,003,975 A | 4/1991 | Hafelfinger et al. |
| 5,003,976 A | 4/1991 | Alt et al. |
| 5,004,472 A | 4/1991 | Wallace |
| 5,004,873 A | 4/1991 | Schnut |
| 5,005,574 A | 4/1991 | Fearnot et al. |
| 5,005,586 A | 4/1991 | Lahr |
| 5,006,884 A | 4/1991 | Ohta et al. |
| 5,006,997 A | 4/1991 | Reich |
| 5,007,401 A | 4/1991 | Grohn et al. |
| 5,007,430 A | 4/1991 | Dardik |
| 5,007,919 A | 4/1991 | Silva et al. |
| 5,009,662 A | 4/1991 | Wallace et al. |
| 5,010,893 A | 4/1991 | Sholder |
| 5,012,286 A | 4/1991 | Kawano et al. |
| 5,012,810 A | 5/1991 | Strand et al. |
| 5,013,292 A | 5/1991 | Lemay et al. |
| 5,014,040 A | 5/1991 | Weaver et al. |
| 5,019,032 A | 5/1991 | Robertson |
| 5,019,041 A | 5/1991 | Robinson et al. |
| 5,020,845 A | 6/1991 | Falcoff et al. |
| 5,021,046 A | 6/1991 | Wallace |
| 5,022,395 A | 6/1991 | Russie |
| 5,024,965 A | 6/1991 | Chang et al. |
| 5,026,180 A | 6/1991 | Tajima et al. |
| 5,026,360 A | 6/1991 | Johnsen et al. |
| 5,028,918 A | 7/1991 | Giles et al. |
| 5,032,822 A | 7/1991 | Sweet |
| 5,036,869 A | 8/1991 | Inahara et al. |
| 5,038,800 A | 8/1991 | Oba et al. |

| | | | | | | |
|---|---|---|---|---|---|---|
| 5,041,086 A | 8/1991 | Koenig et al. | | 5,181,517 A | 1/1993 | Hickey |
| 5,041,826 A | 8/1991 | Milheiser | | 5,184,132 A | 2/1993 | Baird |
| 5,042,503 A | 8/1991 | Torok et al. | | 5,184,614 A | 2/1993 | Collins et al. |
| 5,044,770 A | 9/1991 | Haghkar | | 5,184,619 A | 2/1993 | Austin |
| 5,046,661 A | 9/1991 | Kimura et al. | | 5,185,535 A | 2/1993 | Farb et al. |
| 5,048,060 A | 9/1991 | Arai et al. | | 5,186,224 A | 2/1993 | Schirmacher et al. |
| 5,050,922 A | 9/1991 | Falcoff | | 5,188,106 A | 2/1993 | Nappholz et al. |
| 5,052,910 A | 10/1991 | Hehl et al. | | 5,188,604 A | 2/1993 | Orth |
| 5,053,008 A | 10/1991 | Bajaj | | 5,192,314 A | 3/1993 | Daskalakis |
| 5,057,078 A | 10/1991 | Foote et al. | | 5,195,362 A | 3/1993 | Eason |
| 5,058,583 A | 10/1991 | Geddes et al. | | 5,197,322 A | 3/1993 | Indravudh |
| 5,061,239 A | 10/1991 | Shiels | | 5,199,427 A | 4/1993 | Strickland |
| 5,062,052 A | 10/1991 | Sparer et al. | | 5,199,428 A | 4/1993 | Obel et al. |
| 5,062,053 A | 10/1991 | Shirai et al. | | 5,201,753 A | 4/1993 | Lampropoulos et al. |
| 5,064,974 A | 11/1991 | Vigneau et al. | | 5,204,670 A | 4/1993 | Stinton |
| 5,067,960 A | 11/1991 | Grandjean et al. | | 5,207,429 A | 5/1993 | Walmsley et al. |
| 5,068,779 A | 11/1991 | Sullivan et al. | | 5,209,223 A | 5/1993 | McGorry et al. |
| 5,069,680 A | 12/1991 | Grandjean et al. | | 5,209,732 A | 5/1993 | Lampropoulos et al. |
| 5,077,102 A | 12/1991 | Chong | | 5,211,129 A | 5/1993 | Taylor et al. |
| 5,077,870 A | 1/1992 | Melbye et al. | | 5,211,161 A | 5/1993 | Stef et al. |
| 5,078,139 A | 1/1992 | Strand et al. | | 5,212,476 A | 5/1993 | Maloney |
| 5,082,006 A | 1/1992 | Jonasson et al. | | 5,213,331 A | 5/1993 | Avanzini |
| 5,083,563 A | 1/1992 | Collins et al. | | 5,215,523 A | 6/1993 | Williams et al. |
| 5,084,699 A | 1/1992 | DeMichele | | 5,218,343 A | 6/1993 | Stobbe et al. |
| 5,085,224 A | 2/1992 | Galen et al. | | 5,218,957 A | 6/1993 | Strickland |
| 5,085,258 A | 2/1992 | Fink, Jr. et al. | | 5,226,429 A | 7/1993 | Kuzmak |
| 5,089,673 A | 2/1992 | Strzodka et al. | | 5,226,604 A | 7/1993 | Seiffert et al. |
| 5,089,979 A | 2/1992 | McEachern et al. | | 5,230,694 A | 7/1993 | Rosenblum |
| 5,095,309 A | 3/1992 | Troyk et al. | | 5,233,985 A | 8/1993 | Hudrik |
| 5,096,271 A | 3/1992 | Portman | | 5,235,326 A | 8/1993 | Beigel et al. |
| 5,097,831 A | 3/1992 | Lekholm | | 5,244,269 A | 9/1993 | Harriehausen et al. |
| 5,098,384 A | 3/1992 | Abrams | | 5,244,461 A | 9/1993 | Derlien et al. |
| 5,099,845 A | 3/1992 | Besz et al. | | 5,246,008 A | 9/1993 | Mueller et al. |
| 5,103,832 A | 4/1992 | Jackson | | 5,249,858 A | 10/1993 | Nusser |
| 5,105,810 A | 4/1992 | Collins et al. | | 5,250,020 A | 10/1993 | Bley |
| 5,107,850 A | 4/1992 | Olive | | 5,254,096 A | 10/1993 | Rondelet et al. |
| 5,112,344 A | 5/1992 | Petros et al. | | 5,256,157 A | 10/1993 | Samiotes et al. |
| 5,113,859 A | 5/1992 | Funke et al. | | 5,263,244 A | 11/1993 | Centa et al. |
| 5,113,869 A | 5/1992 | Nappholz et al. | | 5,263,981 A | 11/1993 | Polyak et al. |
| 5,115,676 A | 5/1992 | Lee | | 5,267,940 A | 12/1993 | Moulder |
| 5,117,825 A | 6/1992 | Grevious | | 5,267,942 A | 12/1993 | Saperston |
| 5,120,313 A | 6/1992 | Elftman | | 5,269,891 A | 12/1993 | Colin et al. |
| 5,121,777 A | 6/1992 | Leininger et al. | | 5,271,395 A | 12/1993 | Wahlstrand et al. |
| 5,127,451 A | 7/1992 | Fink, Jr. et al. | | 5,274,859 A | 1/1994 | Redman et al. |
| 5,129,394 A | 7/1992 | Mehra | | 5,280,789 A | 1/1994 | Potts |
| 5,129,806 A | 7/1992 | Hehl et al. | | 5,282,839 A | 2/1994 | Roline et al. |
| 5,131,145 A | 7/1992 | Badoureaux et al. | | 5,282,840 A | 2/1994 | Hudrlik |
| 5,131,388 A | 7/1992 | Pless et al. | | 5,291,894 A | 3/1994 | Nagy et al. |
| 5,133,358 A | 7/1992 | Gustafson et al. | | 5,292,219 A | 3/1994 | Merin et al. |
| 5,135,488 A | 8/1992 | Foote et al. | | 5,295,967 A | 3/1994 | Rondelet et al. |
| 5,139,484 A | 8/1992 | Hazon et al. | | 5,298,022 A | 3/1994 | Bernardi et al. |
| 5,144,949 A | 9/1992 | Olson | | 5,298,884 A | 3/1994 | Gilmore et al. |
| 5,148,580 A | 9/1992 | Dyckow et al. | | 5,300,093 A | 4/1994 | Koestner |
| 5,148,695 A | 9/1992 | Ellis | | 5,300,120 A | 4/1994 | Knapp et al. |
| 5,152,770 A | 10/1992 | Bangmark et al. | | 5,304,112 A | 4/1994 | Mrklas et al. |
| 5,152,776 A | 10/1992 | Pinchuk | | 5,305,923 A | 4/1994 | Kirschner et al. |
| 5,154,170 A | 10/1992 | Bennett et al. | | 5,312,443 A | 5/1994 | Adams et al. |
| 5,154,171 A | 10/1992 | Chirife et al. | | 5,312,452 A | 5/1994 | Salo |
| 5,154,693 A | 10/1992 | East et al. | | 5,312,453 A | 5/1994 | Shelton et al. |
| 5,156,972 A | 10/1992 | Issachar et al. | | 5,313,953 A | 5/1994 | Yomtov et al. |
| 5,158,078 A | 10/1992 | Bennett et al. | | 5,314,451 A | 5/1994 | Mulier |
| 5,163,429 A | 11/1992 | Cohen | | 5,314,457 A | 5/1994 | Jeutter et al. |
| 5,163,904 A | 11/1992 | Lampropoulos et al. | | 5,324,315 A | 6/1994 | Grevious |
| 5,167,615 A | 12/1992 | East et al. | | 5,325,834 A | 7/1994 | Ballheimer et al. |
| 5,168,757 A | 12/1992 | Rabenau et al. | | 5,326,249 A | 7/1994 | Weissfloch et al. |
| 5,168,982 A | 12/1992 | Hakanen et al. | | 5,328,460 A | 7/1994 | Lord et al. |
| 5,171,299 A | 12/1992 | Heitzmann et al. | | 5,330,511 A | 7/1994 | Boute et al. |
| 5,173,873 A | 12/1992 | Wu et al. | | 5,337,750 A | 8/1994 | Wallok |
| 5,174,286 A | 12/1992 | Chirige et al. | | 5,341,430 A | 8/1994 | Aulia et al. |
| 5,174,291 A | 12/1992 | Schoonen et al. | | 5,342,401 A | 8/1994 | Spano et al. |
| 5,176,502 A | 1/1993 | Sanderson et al. | | 5,342,406 A | 8/1994 | Thompson |
| 5,178,197 A | 1/1993 | Healy | | 5,344,388 A | 9/1994 | Maxwell et al. |
| 5,181,423 A | 1/1993 | Philipps et al. | | 5,347,476 A | 9/1994 | McBean, Sr. |

| | | | | | |
|---|---|---|---|---|---|
| 5,348,210 A | 9/1994 | Linzell et al. | 5,523,740 A | 6/1996 | Burgmann et al. |
| 5,348,536 A | 9/1994 | Young et al. | 5,534,018 A | 7/1996 | Wahlstrand et al. |
| 5,350,413 A | 9/1994 | Miller et al. | 5,535,752 A | 7/1996 | Halperin et al. |
| 5,352,180 A | 10/1994 | Candelon et al. | 5,538,005 A | 7/1996 | Harrison et al. |
| 5,353,622 A | 10/1994 | Theener | 5,540,731 A | 7/1996 | Testerman |
| 5,353,800 A | 10/1994 | Pohndorf et al. | 5,541,857 A | 7/1996 | Walter et al. |
| 5,354,200 A | 10/1994 | Klein et al. | 5,545,140 A | 8/1996 | Conero et al. |
| 5,354,316 A | 10/1994 | Keimel | 5,545,151 A | 8/1996 | O'Connor et al. |
| 5,354,319 A | 10/1994 | Wyborny et al. | 5,545,186 A | 8/1996 | Olson et al. |
| 5,360,407 A | 11/1994 | Leonard et al. | 5,545,214 A | 8/1996 | Stevens |
| 5,365,462 A | 11/1994 | McBean, Sr. | 5,547,470 A | 8/1996 | Johnson et al. |
| 5,365,619 A | 11/1994 | Solomon | 5,551,427 A | 9/1996 | Altman |
| 5,365,985 A | 11/1994 | Todd et al. | 5,551,439 A | 9/1996 | Hickey |
| 5,368,040 A | 11/1994 | Carney | 5,554,185 A | 9/1996 | Block et al. |
| 5,370,665 A | 12/1994 | Hudrlik | 5,558,644 A | 9/1996 | Boyd et al. |
| 5,373,852 A | 12/1994 | Harrison et al. | 5,564,434 A | 10/1996 | Halperin et al. |
| 5,375,073 A | 12/1994 | McBean | 5,575,770 A | 11/1996 | Melsky et al. |
| 5,377,128 A | 12/1994 | McBean | 5,584,803 A | 12/1996 | Stevens et al. |
| 5,378,231 A | 1/1995 | Johnson et al. | 5,586,629 A | 12/1996 | Shoberg et al. |
| 5,382,232 A | 1/1995 | Hague et al. | 5,591,171 A | 1/1997 | Brown |
| 5,383,915 A | 1/1995 | Adams | 5,592,939 A | 1/1997 | Martinelli |
| 5,388,578 A | 2/1995 | Yomtov et al. | 5,597,284 A | 1/1997 | Weltlich et al. |
| 5,388,586 A | 2/1995 | Lee et al. | 5,610,083 A | 3/1997 | Chan et al. |
| 5,388,831 A | 2/1995 | Quadri et al. | 5,611,768 A | 3/1997 | Tutrone, Jr. |
| 5,394,909 A | 3/1995 | Mitchell et al. | 5,612,497 A | 3/1997 | Walter et al. |
| 5,396,899 A | 3/1995 | Strittmatter | 5,615,671 A | 4/1997 | Schoonen et al. |
| 5,402,944 A | 4/1995 | Pape et al. | 5,619,991 A | 4/1997 | Sloane |
| 5,406,957 A | 4/1995 | Tansey | 5,622,869 A | 4/1997 | Lewis et al. |
| 5,409,009 A | 4/1995 | Olson | 5,625,946 A | 5/1997 | Wildeson et al. |
| 5,411,031 A | 5/1995 | Yomtov | 5,626,623 A | 5/1997 | Kieval et al. |
| 5,411,551 A | 5/1995 | Winston et al. | 5,626,630 A | 5/1997 | Markowitz et al. |
| 5,411,552 A | 5/1995 | Anderson et al. | 5,630,836 A | 5/1997 | Prem et al. |
| 5,416,372 A | 5/1995 | Ljungstroem et al. | 5,634,255 A | 6/1997 | Bishop et al. |
| 5,417,226 A | 5/1995 | Juma | 5,637,083 A | 6/1997 | Bertrand et al. |
| 5,417,717 A | 5/1995 | Salo et al. | 5,643,207 A | 7/1997 | Rise |
| 5,425,362 A | 6/1995 | Siker et al. | 5,645,065 A | 7/1997 | Shapiro et al. |
| 5,425,713 A | 6/1995 | Taylor et al. | 5,645,116 A | 7/1997 | McDonald |
| 5,431,171 A | 7/1995 | Harrison et al. | 5,650,766 A | 7/1997 | Burgmann et al. |
| 5,431,629 A | 7/1995 | Lampropoulos et al. | 5,673,585 A | 10/1997 | Bishop et al. |
| 5,431,694 A | 7/1995 | Snaper et al. | 5,676,690 A | 10/1997 | Noren et al. |
| 5,433,694 A | 7/1995 | Lim et al. | 5,681,285 A | 10/1997 | Ford et al. |
| 5,437,605 A | 8/1995 | Helmy et al. | 5,686,831 A | 11/1997 | Vandervalk et al. |
| 5,443,215 A | 8/1995 | Fackler | 5,687,734 A | 11/1997 | Dempsey et al. |
| 5,447,519 A | 9/1995 | Peterson | 5,693,076 A | 12/1997 | Kaemmerer |
| 5,449,345 A | 9/1995 | Taylor et al. | 5,702,368 A | 12/1997 | Stevens et al. |
| 5,449,368 A | 9/1995 | Kuzmak | 5,702,427 A | 12/1997 | Ecker et al. |
| 5,456,690 A | 10/1995 | Duong-Van | 5,702,431 A | 12/1997 | Wang et al. |
| 5,461,293 A | 10/1995 | Rozman et al. | 5,704,352 A | 1/1998 | Tremblay et al. |
| 5,461,390 A | 10/1995 | Hoshen | 5,711,302 A | 1/1998 | Lampropoulos et al. |
| 5,464,435 A | 11/1995 | Neumann | 5,716,342 A | 1/1998 | Dumbraveanu et al. |
| 5,467,627 A | 11/1995 | Smith et al. | 5,715,786 A | 2/1998 | Seiberth et al. |
| 5,474,226 A | 12/1995 | Joseph | 5,715,837 A | 2/1998 | Chen |
| 5,479,818 A | 1/1996 | Walter et al. | 5,720,436 A | 2/1998 | Buschor et al. |
| 5,482,049 A | 1/1996 | Addiss et al. | 5,721,382 A | 2/1998 | Kriesel et al. |
| 5,487,760 A | 1/1996 | Villafana | 5,730,101 A | 3/1998 | Aupperle et al. |
| 5,593,430 A | 1/1996 | Renger | 5,732,710 A | 3/1998 | Rabinovich et al. |
| 5,594,665 A | 1/1996 | Walter et al. | 5,733,313 A | 3/1998 | Barreras, Sr. et al. |
| 5,596,986 A | 1/1996 | Goldfarb | 5,738,652 A | 4/1998 | Boyd et al. |
| 5,490,514 A | 2/1996 | Rosenberg | 5,742,233 A | 4/1998 | Hoffman et al. |
| 5,493,738 A | 2/1996 | Sanderson et al. | 5,743,267 A | 4/1998 | Nikolic et al. |
| 5,494,036 A | 2/1996 | Uber, III et al. | 5,749,369 A | 5/1998 | Rabinovich et al. |
| 5,494,193 A | 2/1996 | Kirschner et al. | 5,749,909 A | 5/1998 | Schroeppel et al. |
| 5,504,474 A | 4/1996 | Libman et al. | 5,755,687 A | 5/1998 | Donion |
| 5,505,916 A | 4/1996 | Berry, Jr. | 5,755,748 A | 5/1998 | Borza et al. |
| 5,507,412 A | 4/1996 | Ebert et al. | 5,765,568 A | 6/1998 | Sweezer, Jr. et al. |
| 5,507,737 A | 4/1996 | Palmskog et al. | 5,769,812 A | 6/1998 | Stevens et al. |
| 5,507,785 A | 4/1996 | Deno | 5,771,903 A | 6/1998 | Jakobsson |
| 5,509,888 A | 4/1996 | Miller | 5,782,774 A | 7/1998 | Shmulewitz |
| 5,509,891 A | 4/1996 | DeRidder | 5,787,520 A | 8/1998 | Dunbar |
| 5,513,945 A | 5/1996 | Hartmann et al. | 5,791,344 A | 8/1998 | Schulman et al. |
| 5,514,103 A | 5/1996 | Srisathapat et al. | 5,792,094 A | 8/1998 | Stevens et al. |
| 5,518,504 A | 5/1996 | Polyak | 5,792,179 A | 8/1998 | Sideris |
| 5,520,606 A | 5/1996 | Schoolman et al. | 5,795,325 A | 8/1998 | Valley et al. |

| | | | | | | |
|---|---|---|---|---|---|---|
| 5,796,827 | A | 8/1998 | Coppersmith et al. | 6,135,945 | A | 10/2000 | Sultan |
| 5,797,403 | A | 8/1998 | DiLorenzo | 6,152,885 | A | 11/2000 | Taepke |
| 5,800,375 | A | 9/1998 | Sweezer et al. | 6,158,965 | A | 12/2000 | Butterfield et al. |
| 5,803,917 | A | 9/1998 | Butterfield et al. | 6,159,156 | A | 12/2000 | Van Bockel et al. |
| 5,807,265 | A | 9/1998 | Itoigawa et al. | 6,162,180 | A | 12/2000 | Miesel et al. |
| 5,807,336 | A | 9/1998 | Russo et al. | 6,162,245 | A | 12/2000 | Jayaraman et al. |
| 5,810,015 | A | 9/1998 | Flaherty | 6,168,614 | B1 | 1/2001 | Andersen et al. |
| 5,810,757 | A | 9/1998 | Sweezer, Jr. et al. | 6,171,252 | B1 | 1/2001 | Roberts |
| 5,810,841 | A | 9/1998 | McNeirney et al. | 6,210,347 | B1 | 4/2001 | Forsell |
| 5,814,016 | A | 9/1998 | Valley et al. | 6,216,028 | B1 | 4/2001 | Haynor et al. |
| 5,817,093 | A | 10/1998 | Williamson, IV et al. | 6,234,745 | B1 | 5/2001 | Pugh et al. |
| 5,833,603 | A | 11/1998 | Kovacs et al. | 6,240,316 | B1 | 5/2001 | Richmond et al. |
| 5,836,300 | A | 11/1998 | Mault | 6,240,318 | B1 | 5/2001 | Phillips |
| 5,836,886 | A | 11/1998 | Itoigawa et al. | 6,245,102 | B1 | 6/2001 | Jayaraman |
| 5,840,081 | A | 11/1998 | Anderson et al. | 6,248,080 | B1 | 6/2001 | Miesel et al. |
| 5,849,225 | A | 12/1998 | Ebina et al. | 6,251,093 | B1 | 6/2001 | Valley et al. |
| 5,855,597 | A | 1/1999 | Jayaraman et al. | 6,269,819 | B1 | 8/2001 | Oz et al. |
| 5,855,601 | A | 1/1999 | Bessler et al. | 6,277,078 | B1 | 8/2001 | Porat et al. |
| 5,860,938 | A | 1/1999 | LaFontaine et al. | 6,285,897 | B1 | 9/2001 | Kilcoyne et al. |
| 5,861,018 | A | 1/1999 | Feierbach | 6,292,697 | B1 | 9/2001 | Roberts |
| 5,863,366 | A | 1/1999 | Snow | 6,305,381 | B1 | 10/2001 | Weijand et al. |
| 5,868,702 | A | 2/1999 | Stevens et al. | 6,309,350 | B1 | 10/2001 | Van Tassel et al. |
| 5,873,837 | A | 2/1999 | Lieber et al. | 6,315,769 | B1 | 11/2001 | Peer et al. |
| 5,875,953 | A | 3/1999 | Shioya et al. | 6,319,208 | B1 | 11/2001 | Abita et al. |
| 5,879,499 | A | 3/1999 | Corvi | 6,328,699 | B1 | 12/2001 | Eigler et al. |
| 5,881,919 | A | 3/1999 | Womac et al. | 6,338,735 | B1 | 1/2002 | Stevens |
| 5,885,238 | A | 3/1999 | Stevens et al. | 6,357,438 | B1 | 3/2002 | Hansen |
| 5,887,475 | A | 3/1999 | Muldner | 6,360,122 | B1 | 3/2002 | Fischell et al. |
| 5,899,927 | A | 5/1999 | Ecker et al. | 6,360,822 | B1 | 3/2002 | Robertson et al. |
| 5,916,179 | A | 6/1999 | Sharrock | 6,366,799 | B1 | 4/2002 | Acker et al. |
| 5,916,237 | A | 6/1999 | Schu | 6,366,817 | B1 | 4/2002 | Kung |
| 5,928,182 | A | 7/1999 | Kraus et al. | 6,379,308 | B1 | 4/2002 | Brockway et al. |
| 5,935,078 | A | 8/1999 | Feierbach | 6,379,380 | B1 | 4/2002 | Satz |
| 5,935,083 | A | 8/1999 | Williams | 6,398,752 | B1 | 6/2002 | Sweezer, Jr. et al. |
| 5,938,669 | A | 8/1999 | Klaiber et al. | 6,409,674 | B1 | 6/2002 | Brockway et al. |
| 5,951,487 | A | 9/1999 | Brehmeier-Flick et al. | 6,416,291 | B1 | 7/2002 | Butterfield et al. |
| 5,957,861 | A | 9/1999 | Combs et al. | 6,423,031 | B1 | 7/2002 | Donlon |
| 5,967,986 | A | 10/1999 | Cimochowski et al. | 6,430,444 | B1 | 8/2002 | Borza et al. |
| 5,970,801 | A | 10/1999 | Ciobanu et al. | 6,431,175 | B1 | 8/2002 | Penner et al. |
| 5,971,934 | A | 10/1999 | Scherer et al. | 6,432,040 | B1 | 8/2002 | Meah |
| 5,974,873 | A | 11/1999 | Nelson et al. | 6,443,887 | B1 | 9/2002 | Derus et al. |
| 5,978,985 | A | 11/1999 | Thurman | 6,443,893 | B1 | 9/2002 | Schnakenberg et al. |
| 5,991,664 | A | 11/1999 | Seligman | 6,450,173 | B1 | 9/2002 | Forsell |
| 5,993,395 | A | 11/1999 | Shulze | 6,450,543 | B1 | 9/2002 | Fukano et al. |
| 5,993,398 | A | 11/1999 | Alperin | 6,450,946 | B1 | 9/2002 | Forsell |
| 5,995,874 | A | 11/1999 | Borza et al. | 6,453,907 | B1 | 9/2002 | Forsell et al. |
| 6,009,878 | A | 1/2000 | Weijand et al. | 6,454,699 | B1 | 9/2002 | Forsell |
| 6,010,482 | A | 1/2000 | Kriesel et al. | 6,454,700 | B1 | 9/2002 | Forsell |
| 6,015,386 | A | 1/2000 | Kensey et al. | 6,454,701 | B1 | 9/2002 | Forsell et al. |
| 6,015,387 | A | 1/2000 | Schwartz et al. | 6,554,698 | B2 | 9/2002 | Forsell et al. |
| 6,019,729 | A | 2/2000 | Itoigawa et al. | 6,460,543 | B1 | 10/2002 | Forsell |
| 6,024,704 | A | 2/2000 | Meador et al. | 6,461,292 | B1 | 10/2002 | Forsell et al. |
| 6,030,413 | A | 2/2000 | Lazarus | 6,461,293 | B1 | 10/2002 | Forsell |
| 6,035,461 | A | 3/2000 | Nguyen | 6,463,329 | B1 | 10/2002 | Goedeke |
| 6,053,873 | A | 4/2000 | Govari et al. | 6,463,935 | B1 | 10/2002 | Forsell |
| 6,056,723 | A | 5/2000 | Donlon | 6,464,628 | B1 | 10/2002 | Forsell |
| 6,058,330 | A | 5/2000 | Borza et al. | 6,470,212 | B1 | 10/2002 | Weijand et al. |
| 6,059,757 | A | 5/2000 | Macoviak et al. | 6,470,213 | B1 | 10/2002 | Alley |
| 6,067,474 | A | 5/2000 | Schulman et al. | 6,470,892 | B1 | 10/2002 | Forsell |
| 6,067,991 | A | 5/2000 | Forsell et al. | 6,471,635 | B1 | 10/2002 | Forsell |
| 6,071,267 | A | 6/2000 | Zamierowski | 6,475,136 | B1 | 11/2002 | Forsell |
| 6,076,016 | A | 6/2000 | Feierbach | 6,475,170 | B1 | 11/2002 | Doron et al. |
| 6,083,174 | A | 7/2000 | Brehmeier-Flick et al. | 6,481,292 | B1 | 11/2002 | Reich |
| 6,087,831 | A | 7/2000 | Bornert et al. | 6,482,145 | B1 | 11/2002 | Forsell |
| 6,090,096 | A | 7/2000 | St. Goar et al. | 6,482,171 | B1 | 11/2002 | Corvi et al. |
| 6,016,477 | A | 8/2000 | Meisel et al. | 6,482,177 | B1 | 11/2002 | Leinders et al. |
| 6,102,678 | A | 8/2000 | Peciat et al. | 6,486,588 | B2 | 11/2002 | Doron et al. |
| 6,102,856 | A | 8/2000 | Groff et al. | 6,503,189 | B1 | 1/2003 | Forsell et al. |
| 6,102,922 | A | 8/2000 | Jakobsson et al. | 6,503,208 | B1 | 1/2003 | Skovlund et al. |
| 6,106,551 | A | 8/2000 | Crossett et al. | 6,504,286 | B1 | 1/2003 | Porat et al. |
| 6,110,145 | A | 8/2000 | Macoviak | 6,505,062 | B1 | 1/2003 | Ritter et al. |
| 6,113,553 | A | 9/2000 | Chubbuck | 6,511,490 | B2 | 1/2003 | Robert |
| 6,131,664 | A | 10/2000 | Sonnier | 6,516,212 | B1 | 2/2003 | Bladen et al. |

| Patent No. | Date | Inventor |
|---|---|---|
| 6,531,739 B2 | 3/2003 | Cable et al. |
| 6,533,719 B2 | 3/2003 | Kuyava et al. |
| 6,533,733 B1 | 3/2003 | Ericson et al. |
| 6,542,350 B1 | 4/2003 | Rogers |
| 6,558,321 B1 | 5/2003 | Burd et al. |
| 6,558,994 B2 | 5/2003 | Cha et al. |
| 6,573,563 B2 | 6/2003 | Lee et al. |
| 6,582,462 B1 | 6/2003 | Andersen et al. |
| 6,587,709 B2 | 7/2003 | Solf et al. |
| 6,589,189 B2 | 7/2003 | Meyerson et al. |
| 6,599,250 B2 | 7/2003 | Webb et al. |
| 6,605,112 B1 | 8/2003 | Moll et al. |
| 6,629,534 B1 | 10/2003 | St. Goar et al. |
| 6,640,137 B2 | 10/2003 | MacDonald |
| 6,641,610 B2 | 11/2003 | Wolf et al. |
| 6,645,143 B2 | 11/2003 | Van Tassel et al. |
| 6,654,629 B2 | 11/2003 | Montegrande |
| 6,673,109 B2 | 1/2004 | Cox |
| 6,678,561 B2 | 1/2004 | Forsell et al. |
| 6,682,480 B1 | 1/2004 | Habib et al. |
| 6,682,503 B1 | 1/2004 | Fariss et al. |
| 6,682,559 B2 | 1/2004 | Myers |
| 6,689,046 B2 | 2/2004 | Sayet et al. |
| 6,690,963 B2 | 2/2004 | Ben-Haim et al. |
| 6,695,866 B1 | 2/2004 | Kuehn et al. |
| 6,709,385 B2 | 3/2004 | Forsell et al. |
| 6,718,200 B2 | 4/2004 | Marmaropoulos et al. |
| 6,719,787 B2 | 4/2004 | Cox |
| 6,719,788 B2 | 4/2004 | Cox |
| 6,719,789 B2 | 4/2004 | Cox |
| 6,731,976 B2 | 5/2004 | Penn et al. |
| 6,733,525 B2 | 5/2004 | Yang et al. |
| 6,736,846 B2 | 5/2004 | Cox |
| 6,752,813 B2 | 6/2004 | Goldfarb et al. |
| 6,757,557 B1 | 6/2004 | Bladen et al. |
| 6,779,851 B2 | 8/2004 | Bouchiere |
| 6,796,942 B1 | 9/2004 | Kreiner et al. |
| 6,822,343 B2 | 11/2004 | Estevez |
| 6,851,628 B1 | 2/2005 | Garrison et al. |
| 6,855,115 B2 | 2/2005 | Fonseca et al. |
| 6,889,772 B2 | 5/2005 | Buytaeft et al. |
| 6,890,300 B2 | 5/2005 | Lloyd et al. |
| 6,896,651 B2 | 5/2005 | Gross et al. |
| 6,898,690 B2 | 5/2005 | Lambrecht et al. |
| 6,913,600 B2 | 7/2005 | Valley et al. |
| 6,915,165 B2 | 7/2005 | Forsell et al. |
| 6,926,246 B2 | 8/2005 | Ginggen et al. |
| 6,929,653 B2 | 8/2005 | Strecter |
| 6,932,792 B1 | 8/2005 | St. Goar et al. |
| 6,951,229 B2 | 10/2005 | Garrison et al. |
| 6,951,571 B1 | 10/2005 | Srivastava |
| 6,953,429 B2 | 10/2005 | Forsell et al. |
| 6,961,619 B2 | 11/2005 | Casey |
| 6,970,742 B2 | 11/2005 | Mann et al. |
| 6,979,350 B2 | 12/2005 | Moll et al. |
| 6,985,078 B2 | 1/2006 | Suzuki et al. |
| 6,989,027 B2 | 1/2006 | Allen et al. |
| 7,011,095 B2 | 3/2006 | Wolf et al. |
| 7,011,624 B2 | 3/2006 | Forsell et al. |
| 7,017,583 B2 | 3/2006 | Forsell et al. |
| 7,018,406 B2 | 3/2006 | Seguin et al. |
| 7,021,402 B2 | 4/2006 | Beato et al. |
| 7,025,727 B2 | 4/2006 | Brockway et al. |
| 7,044,920 B2 | 5/2006 | Letort et al. |
| 7,060,080 B2 | 6/2006 | Bachmann et al. |
| 7,081,683 B2 | 7/2006 | Ariav et al. |
| 7,109,933 B2 | 9/2006 | Ito et al. |
| 7,131,447 B2 | 11/2006 | Sterman et al. |
| 7,131,945 B2 | 11/2006 | Fink et al. |
| 7,134,580 B2 | 11/2006 | Garrison et al. |
| 7,143,462 B2 | 12/2006 | Hohlbein |
| 7,144,400 B2 | 12/2006 | Byrum et al. |
| 7,147,640 B2 | 12/2006 | Huebner et al. |
| 7,153,262 B2 | 12/2006 | Stivoric et al. |
| 7,187,978 B2 | 3/2007 | Makek et al. |
| 7,225,032 B2 | 5/2007 | Schmeling et al. |
| 7,257,438 B2 | 8/2007 | Kinast |
| 7,285,090 B2 | 10/2007 | Stivoric et al. |
| 2001/0011543 A1 | 8/2001 | Forsell |
| 2001/0041823 A1 | 11/2001 | Snyder et al. |
| 2002/0049394 A1 | 4/2002 | Roy et al. |
| 2002/0120200 A1 | 8/2002 | Brockway et al. |
| 2002/0138009 A1 | 9/2002 | Brockway et al. |
| 2002/0177782 A1 | 11/2002 | Penner |
| 2003/0009201 A1 | 1/2003 | Forsell |
| 2003/0023134 A1 | 1/2003 | Tracey |
| 2003/0030893 A1 | 2/2003 | Cornelius et al. |
| 2003/0032857 A1 | 2/2003 | Forsell |
| 2003/0037591 A1 | 2/2003 | Ashton et al. |
| 2003/0045775 A1 | 3/2003 | Forsell |
| 2003/0066536 A1 | 4/2003 | Forsell |
| 2003/0088148 A1 | 5/2003 | Forsell |
| 2003/0092962 A1 | 5/2003 | Forsell |
| 2003/0093117 A1 | 5/2003 | Saadat |
| 2003/0100929 A1 | 5/2003 | Forsell |
| 2003/0105385 A1 | 6/2003 | Forsell |
| 2003/0109771 A1 | 6/2003 | Forsell |
| 2003/0114729 A1 | 6/2003 | Forsell |
| 2003/0120150 A1 | 6/2003 | Govari |
| 2003/0125605 A1 | 7/2003 | Forsell |
| 2003/0125768 A1 | 7/2003 | Peter |
| 2003/0135089 A1 | 7/2003 | Forsell |
| 2003/0135090 A1 | 7/2003 | Forsell |
| 2003/0136417 A1 | 7/2003 | Fonseca et al. |
| 2003/0144648 A1 | 7/2003 | Forsell |
| 2003/0163079 A1 | 8/2003 | Burnett |
| 2003/0216666 A1 | 11/2003 | Ericson et al. |
| 2003/0225371 A1 | 12/2003 | Hadzic et al. |
| 2004/0014456 A1 | 1/2004 | Vnnen |
| 2004/0039256 A1 | 2/2004 | Kawatahara et al. |
| 2004/0054351 A1 | 3/2004 | Deniega et al. |
| 2004/0054352 A1 | 3/2004 | Clark et al. |
| 2004/0055610 A1 | 3/2004 | Forsell |
| 2004/0064030 A1 | 4/2004 | Forsell |
| 2004/0082867 A1 | 4/2004 | Esch et al. |
| 2004/0082904 A1 | 4/2004 | Houde et al. |
| 2004/0106874 A1 | 6/2004 | Eigler et al. |
| 2004/0113790 A1 | 6/2004 | Hamel et al. |
| 2004/0133092 A1 | 7/2004 | Kain |
| 2004/0143212 A1 | 7/2004 | Trombley et al. |
| 2004/0147969 A1 | 7/2004 | Mann et al. |
| 2004/0172087 A1 | 9/2004 | Forsell |
| 2004/0186396 A1 | 9/2004 | Roy et al. |
| 2004/0193045 A1 | 9/2004 | Scarborough et al. |
| 2004/0215159 A1 | 10/2004 | Forsell |
| 2004/0243148 A1 | 12/2004 | Wasielewski |
| 2004/0254537 A1 | 12/2004 | Conlon et al. |
| 2005/0004516 A1 | 1/2005 | Vanney |
| 2005/0015014 A1 | 1/2005 | Fonseca et al. |
| 2005/0025979 A1 | 2/2005 | Sandt et al. |
| 2005/0027175 A1 | 2/2005 | Yang |
| 2005/0027998 A1 | 2/2005 | Teglia et al. |
| 2005/0038328 A1 | 2/2005 | Stoehrer et al. |
| 2005/0061079 A1 | 3/2005 | Schulman |
| 2005/0065450 A1 | 3/2005 | Stuebe et al. |
| 2005/0102026 A1 | 5/2005 | Turner et al. |
| 2005/0159789 A1 | 7/2005 | Brockway et al. |
| 2005/0165317 A1 | 7/2005 | Turner et al. |
| 2005/0182330 A1 | 8/2005 | Brockway et al. |
| 2005/0187482 A1 | 8/2005 | O'Brien et al. |
| 2005/0187488 A1 | 8/2005 | Wolf |
| 2005/0192642 A1 | 9/2005 | Forsell |
| 2005/0203360 A1 | 9/2005 | Brauker et al. |
| 2005/0240144 A1 | 10/2005 | Wassermann et al. |
| 2005/0240155 A1 | 10/2005 | Conlon |
| 2005/0240156 A1 | 10/2005 | Conlon |

| | | |
|---|---|---|
| 2005/0250979 A1 | 11/2005 | Coe |
| 2005/0267406 A1 | 12/2005 | Hassler |
| 2005/0267500 A1 | 12/2005 | Hassler, Jr. et al. |
| 2005/0272968 A1 | 12/2005 | Byrum et al. |
| 2005/0277960 A1 | 12/2005 | Hassler et al. |
| 2005/0277974 A1 | 12/2005 | Hasslet et al. |
| 2005/0288604 A1 | 12/2005 | Eigler et al. |
| 2005/0288720 A1 | 12/2005 | Ross et al. |
| 2005/0288721 A1 | 12/2005 | Girouard et al. |
| 2005/0288739 A1 | 12/2005 | Hassler et al. |
| 2005/0288740 A1 | 12/2005 | Hassler |
| 2005/0288741 A1 | 12/2005 | Hassler et al. |
| 2005/0288742 A1 | 12/2005 | Giordano et al. |
| 2006/0002035 A1 | 1/2006 | Gao et al. |
| 2006/0010090 A1 | 1/2006 | Brockway et al. |
| 2006/0020224 A1 | 1/2006 | Geiger |
| 2006/0020305 A1 | 1/2006 | Desai et al. |
| 2006/0035446 A1 | 2/2006 | Chang et al. |
| 2006/0047205 A1 | 3/2006 | Ludomirsky et al. |
| 2006/0049714 A1 | 3/2006 | Liu et al. |
| 2006/0058627 A1 | 3/2006 | Flaherty et al. |
| 2006/0064134 A1 | 3/2006 | Mazar et al. |
| 2006/0085051 A1 | 4/2006 | Fritsch |
| 2006/0089571 A1 | 4/2006 | Gertner |
| 2006/0089619 A1 | 4/2006 | Ginggen |
| 2006/0094966 A1 | 5/2006 | Brockway et al. |
| 2006/0100531 A1 | 5/2006 | Moser |
| 2006/0113187 A1 | 6/2006 | Deng et al. |
| 2006/0118793 A1 | 6/2006 | Yang et al. |
| 2006/0122285 A1 | 6/2006 | Falloon et al. |
| 2006/0122863 A1 | 6/2006 | Gottesman et al. |
| 2006/0142635 A1 | 6/2006 | Forsell |
| 2006/0149124 A1 | 7/2006 | Forsell |
| 2006/0149161 A1 | 7/2006 | Wilson et al. |
| 2006/0149324 A1 | 7/2006 | Mann et al. |
| 2006/0149327 A1 | 7/2006 | Hedberg et al. |
| 2006/0157701 A1 | 7/2006 | Bauer et al. |
| 2006/0161186 A1 | 7/2006 | Hassler et al. |
| 2006/0178617 A1 | 8/2006 | Adams et al. |
| 2006/0178695 A1 | 8/2006 | Decant et al. |
| 2006/0183967 A1 | 8/2006 | Lechner |
| 2006/0184206 A1 | 8/2006 | Baker et al. |
| 2006/0189887 A1 | 8/2006 | Hassler et al. |
| 2006/0189888 A1 | 8/2006 | Hassler et al. |
| 2006/0189889 A1 | 8/2006 | Gertner |
| 2006/0199997 A1 | 9/2006 | Hassler, Jr. et al. |
| 2006/0211912 A1 | 9/2006 | Dlugos et al. |
| 2006/0211913 A1 | 9/2006 | Dlugos et al. |
| 2006/0211914 A1 | 9/2006 | Hassler et al. |
| 2006/0217668 A1 | 9/2006 | Schulze et al. |
| 2006/0217673 A1 | 9/2006 | Schulze et al. |
| 2006/0235310 A1 | 10/2006 | O'Brien et al. |
| 2006/0235439 A1 | 10/2006 | Molitor et al. |
| 2006/0235448 A1 | 10/2006 | Roslin et al. |
| 2006/0244914 A1 | 11/2006 | Cech et al. |
| 2006/0247682 A1 | 11/2006 | Gerber et al. |
| 2006/0247719 A1 | 11/2006 | Maschino et al. |
| 2006/0247721 A1 | 11/2006 | Maschino et al. |
| 2006/0247722 A1 | 11/2006 | Maschino et al. |
| 2006/0247723 A1 | 11/2006 | Gerber et al. |
| 2006/0247724 A1 | 11/2006 | Geber et al. |
| 2006/0247725 A1 | 11/2006 | Gerber et al. |
| 2006/0252982 A1 | 11/2006 | Hassler et al. |
| 2006/0293625 A1 | 12/2006 | Hunt et al. |
| 2006/0293626 A1 | 12/2006 | Byrum et al. |
| 2006/0293627 A1 | 12/2006 | Byrum et al. |
| 2007/0010790 A1 | 1/2007 | Byrum et al. |
| 2007/0027356 A1 | 2/2007 | Ortiz |
| 2007/0027493 A1 | 2/2007 | Ben-Haim et al. |
| 2007/0067206 A1 | 3/2007 | Haggerty et al. |
| 2007/0070906 A1 | 3/2007 | Thakur |
| 2007/0072452 A1 | 3/2007 | Inagaki et al. |
| 2007/0081304 A1 | 4/2007 | Takeguchi |

| | | |
|---|---|---|
| 2007/0156013 A1 | 7/2007 | Birk |
| 2007/0167672 A1 | 7/2007 | Dlugos et al. |
| 2007/0173881 A1 | 7/2007 | Birk et al. |
| 2007/0179583 A1 | 8/2007 | Goetzinger et al. |
| 2007/0208313 A1 | 9/2007 | Conlon et al. |
| 2007/0225781 A1 | 9/2007 | Saadat et al. |
| 2008/0009680 A1 | 1/2008 | Hassler |
| 2008/0172072 A1 | 7/2008 | Pool et al. |
| 2008/0250340 A1 | 10/2008 | Dlugos et al. |
| 2008/0250341 A1 | 10/2008 | Dlugos et al. |
| 2009/0005703 A1 | 1/2009 | Fasciano |

FOREIGN PATENT DOCUMENTS

| | | |
|---|---|---|
| CA | 1059035 | 7/1979 |
| CA | 1119469 | 3/1982 |
| CA | 1275135 | 10/1990 |
| CA | 1277885 | 12/1990 |
| CA | 1317482 | 5/1993 |
| CA | 2082015 | 5/1993 |
| CA | 1327191 | 2/1994 |
| CA | 2119101 | 9/1994 |
| CA | 2305998 | 4/1999 |
| CN | 1119469 | 3/1982 |
| CN | 1059035 | 2/1992 |
| CN | 1241003 | 1/2000 |
| DE | 9416395 | 12/1994 |
| DE | 10156494 | 6/2003 |
| EA | 4581 | 6/2004 |
| EP | 0417171 | 3/1991 |
| EP | 0508141 | 10/1992 |
| EP | 0568730 | 11/1993 |
| EP | 0605302 | 7/1994 |
| EP | 0 654 232 | 5/1995 |
| EP | 0660482 | 6/1995 |
| EP | 0714017 | 5/1996 |
| EP | 0769340 | 4/1997 |
| EP | 0846475 | 6/1998 |
| EP | 0848780 | 6/1998 |
| EP | 0876808 | 11/1998 |
| EP | 0888079 | 1/1999 |
| EP | 0914059 | 5/1999 |
| EP | 0981293 | 3/2000 |
| EP | 0997680 | 5/2000 |
| EP | 1003021 | 5/2000 |
| EP | 1022983 | 8/2000 |
| EP | 1050265 | 11/2000 |
| EP | 1115329 | 7/2001 |
| EP | 1119314 | 8/2001 |
| EP | 1128871 | 9/2001 |
| EP | 1202674 | 5/2002 |
| EP | 1213991 | 6/2002 |
| EP | 1253877 | 11/2002 |
| EP | 1253880 | 11/2002 |
| EP | 1253881 | 11/2002 |
| EP | 1253883 | 11/2002 |
| EP | 1253888 | 11/2002 |
| EP | 1255511 | 11/2002 |
| EP | 1255513 | 11/2002 |
| EP | 1255514 | 11/2002 |
| EP | 1263355 | 12/2002 |
| EP | 1263357 | 12/2002 |
| EP | 1284691 | 2/2003 |
| EP | 1253879 | 11/2003 |
| EP | 1374758 | 1/2004 |
| EP | 1442715 | 8/2004 |
| EP | 1488735 | 12/2004 |
| EP | 1500411 | 1/2005 |
| EP | 1510306 | 3/2005 |
| EP | 1518514 | 3/2005 |
| EP | 1545303 | 6/2005 |
| EP | 1547549 | 6/2005 |
| EP | 1563814 | 8/2005 |

| | | |
|---|---|---|
| EP | 1568338 | 8/2005 |
| EP | 1582175 | 10/2005 |
| EP | 1582176 | 10/2005 |
| EP | 1584303 | 10/2005 |
| EP | 1586283 | 10/2005 |
| EP | 1591086 | 11/2005 |
| EP | 1593359 | 11/2005 |
| EP | 1598030 | 11/2005 |
| EP | 1600120 | 11/2005 |
| EP | 1609440 | 12/2005 |
| EP | 1649884 | 4/2006 |
| EP | 1674033 | 6/2006 |
| EP | 1 676 527 | 7/2006 |
| EP | 1704833 | 9/2006 |
| EP | 1 736 123 | 12/2006 |
| EP | 1799119 | 6/2007 |
| GB | 2355937 | 5/2001 |
| JP | 2006/175191 | 7/2006 |
| WO | WO 89/11244 | 11/1989 |
| WO | WO 89/11701 | 11/1989 |
| WO | WO 90/04368 | 5/1990 |
| WO | WO 95/11057 | 4/1995 |
| WO | WO 97/15351 | 5/1997 |
| WO | WO 97/33513 | 9/1997 |
| WO | WO 98/33554 | 8/1998 |
| WO | WO 98/35610 | 8/1998 |
| WO | WO 99/01063 | 1/1999 |
| WO | WO 99/18850 | 4/1999 |
| WO | WO 00/04945 | 2/2000 |
| WO | WO 00/33738 | 6/2000 |
| WO | WO 00/72899 | 12/2000 |
| WO | WO 01/04487 | 1/2001 |
| WO | WO 01/12075 | 2/2001 |
| WO | WO 01/12076 | 2/2001 |
| WO | WO 01/12077 | 2/2001 |
| WO | WO 01/12078 | 2/2001 |
| WO | WO 01/21066 | 3/2001 |
| WO | WO 01/36014 | 5/2001 |
| WO | WO 01/45485 | 6/2001 |
| WO | WO 01/45486 | 6/2001 |
| WO | WO 01/47431 | 7/2001 |
| WO | WO 01/47432 | 7/2001 |
| WO | WO 01/47433 | 7/2001 |
| WO | WO 01/47434 | 7/2001 |
| WO | WO 01/47435 | 7/2001 |
| WO | WO 01/47440 | 7/2001 |
| WO | WO 01/47575 | 7/2001 |
| WO | WO 01/48451 | 7/2001 |
| WO | WO 01/49245 | 7/2001 |
| WO | WO 01/50832 | 7/2001 |
| WO | WO 01/50833 | 7/2001 |
| WO | WO 01/54626 | 8/2001 |
| WO | WO 01/58388 | 8/2001 |
| WO | WO 01/58390 | 8/2001 |
| WO | WO 01/58391 | 8/2001 |
| WO | WO 01/58393 | 8/2001 |
| WO | WO 01/60453 | 8/2001 |
| WO | WO 01/81890 | 11/2001 |
| WO | WO 02/00118 | 1/2002 |
| WO | WO 02/15769 | 2/2002 |
| WO | WO 02/26161 | 4/2002 |
| WO | WO 02/53228 | 7/2002 |
| WO | WO 02/55126 | 7/2002 |
| WO | WO 02/58551 | 8/2002 |
| WO | WO 02/65894 | 8/2002 |
| WO | WO 02/76289 | 10/2002 |
| WO | WO 02/82984 | 10/2002 |
| WO | WO 02/89655 | 11/2002 |
| WO | WO 02/90894 | 11/2002 |
| WO | WO 02/100481 | 12/2002 |
| WO | WO 03/002192 | 1/2003 |
| WO | WO 03/002193 | 1/2003 |
| WO | WO 03/061467 | 1/2003 |
| WO | WO 03/043534 | 5/2003 |
| WO | WO 03/061504 | 7/2003 |
| WO | WO 2004/014456 | 2/2004 |
| WO | WO 2005/027998 | 3/2005 |
| WO | WO 2005/084544 | 9/2005 |
| WO | WO 2006/018927 | 2/2006 |
| WO | WO 2007/140430 | 12/2007 |
| WO | WO 2008/088949 | 7/2008 |

OTHER PUBLICATIONS

European Search Report dated Jun. 19, 2009 for Application No. 09250581.
European Search Report dated Jul. 10, 2009 for Application No. 09250590.
European Search Report dated Jul. 10, 2009 for Application No. 09250600.
European Search Report dated Aug. 13, 2009 for Application No. 08251093.
International Search Report and Written Opinion dated Sep. 22, 2008 for Application No. PCT/US2008/053394.
U.S. Appl. No. 12/039,014, filed Feb. 28, 2008, Dlugos, Jr. et al.
European Search Report dated May 2, 2008 for Application No. EP 06250968.
European Examination Report dated Dec. 9, 2008 for Application No. EP 06250968.
European Search Report dated Nov. 3, 2008 for Application No. EP 08251508.
European Examination Report dated Jul. 23, 2007 for Application No. EP 06253286.
European Search Report dated Sep. 28, 2006 for Application No. EP 06253286.
European Search Report dated Feb. 10, 2009 for Application No. EP 07250915.
Abstract for JP2006/175191.
Lechner, Wolfgang, et al.-"In Vivo Band Manometry: A New Access to Band Adjustment" -*Obesity Surgery, 15, 1432-1436*-2005.
Author Unknown-"Report—Wireless in Healthcare"-The FocalPoint Group—2004.
EPO Search Report dated Jul. 12, 2007, for EP Application No. 07250931.8.
EPO Search Report dated Jul. 23, 2007, for EP Application No. 07250932.6.

SYSTEM AND METHOD FOR DETERMINING IMPLANTED DEVICE POSITIONING AND OBTAINING PRESSURE DATA

PRIORITY

This application is a continuation-in-part of prior co-pending U.S. Non-Provisional application Ser. No. 11/065,410, filed Feb. 24, 2005, entitled "Device for Non-Invasive Measurement of Fluid Pressure in an Adjustable Restriction Device," now U.S. Pat. No. 7,699,770, issued Apr. 20, 2010, the disclosure of which is incorporated by reference herein.

FIELD

Embodiments of the present invention relate generally to implantable restriction devices, particularly fluid filled restriction devices. Embodiments of the present invention have even further relation to food intake restriction devices for the treatment of morbid obesity.

BACKGROUND

Many devices and methods for treating obesity have been made and used, including but not limited to adjustable gastric bands. An example of such an adjustable gastric band is disclosed in U.S. Pat. No. 6,067,991, entitled "Mechanical Food Intake Restriction Device" which issued on May 30, 2000, which is incorporated herein by reference. To the extent that an adjustable gastric band system is fluid based, those of ordinary skill in the art will appreciate that it may be advantageous to acquire data indicating the pressure of fluid in the band system. Similar advantages may be achieved with fluid-filled members implanted within the stomach cavity or elsewhere. Such pressure data may be obtained before, during, and/or after pressure adjustment, and may be useful for adjustment, diagnostic, monitoring, or other purposes. The foregoing examples are merely illustrative and not exhaustive. While a variety of techniques and devices have been used treat obesity, it is believed that no one prior to the inventors has previously made or used an invention as described in the appended claims.

SUMMARY

In one aspect, a sense head system comprises a housing, a plurality of orthogonal coils, a needle window, and a user interface. The plurality of orthogonal coils comprise a plurality of horizontal coils and a plurality of vertical coils. The plurality of orthogonal coils are configured to receive RF signals communicated from a source of RF energy. The plurality of orthogonal coils are located within the housing. The needle window is formed in the housing, and is configured to receive a syringe needle. The user interface is in communication with the plurality of orthogonal coils, and is configured to provide an indication to a user relating to the position of the needle window relative to a needle target located within a patient. Data indicative of the position of the needle window relative to the needle target is obtained using the plurality of horizontal coils.

In another aspect, a system for positioning a needle and obtaining pressure data comprises a sense head and a display device in communication with the sense head. The sense head comprises a housing, a plurality of receiving coils located within the housing, a needle window formed through the housing, and a telemetry coil. The plurality of receiving coils are operable to receive RF signals communicated from a source of RF energy. The needle window is configured to receive a needle. The telemetry coils is configured to receive pressure data obtained from a pressure sensor configured to sense the pressure of a fluid within a patient. The display device is configured to provide an indication to a user relating to he position of the needle window over a needle target. Data indicative of the position of the needle window over the needle target is obtained using the plurality of receiving coils. The display device is further configured to process the pressure data.

In yet another aspect, a method for selecting a location for inserting a needle into a patient comprises providing a sense head. The sense head comprises a housing, a plurality of receiving coils, and a needle window formed through the housing. The plurality of receiving coils are operable to receive RF signals communicated from a source of RF energy. The coils are located within the housing. The needle window is configured to receive a needle. The method further comprises placing the sense head adjacent to a patient. The patient has an implanted restriction system, which comprises an injection port, a restriction device, a fluid, and a pressure sensor. The injection port comprises one or more telemetry coils. At least one of the one or more telemetry coils is the source of RF energy. The restriction device is operable to adjustably form a restriction within the patient. The fluid is located within the injection port and in the restriction device. The pressure sensor is operable to capture data indicative of the pressure of the fluid. The method further comprises positioning the sense head substantially over the injection port. The act of positioning the sense head over the injection port comprises monitoring RF signals received by the plurality of receiving coils to determine the position of the sense head relative to the injection port. The method further comprises inserting a needle through the needle window into the injection port.

Still other examples, features, aspects, embodiments, and advantages of the invention will become apparent to those skilled in the art from the following description, which includes by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

BRIEF DESCRIPTION OF THE FIGURES

While the specification concludes with claims which particularly point out and distinctly claim the invention, it is believed the present invention will be better understood from the following description of certain examples taken in conjunction with the accompanying drawings, in which like reference numerals identify the same elements and in which:

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

Figure 1:
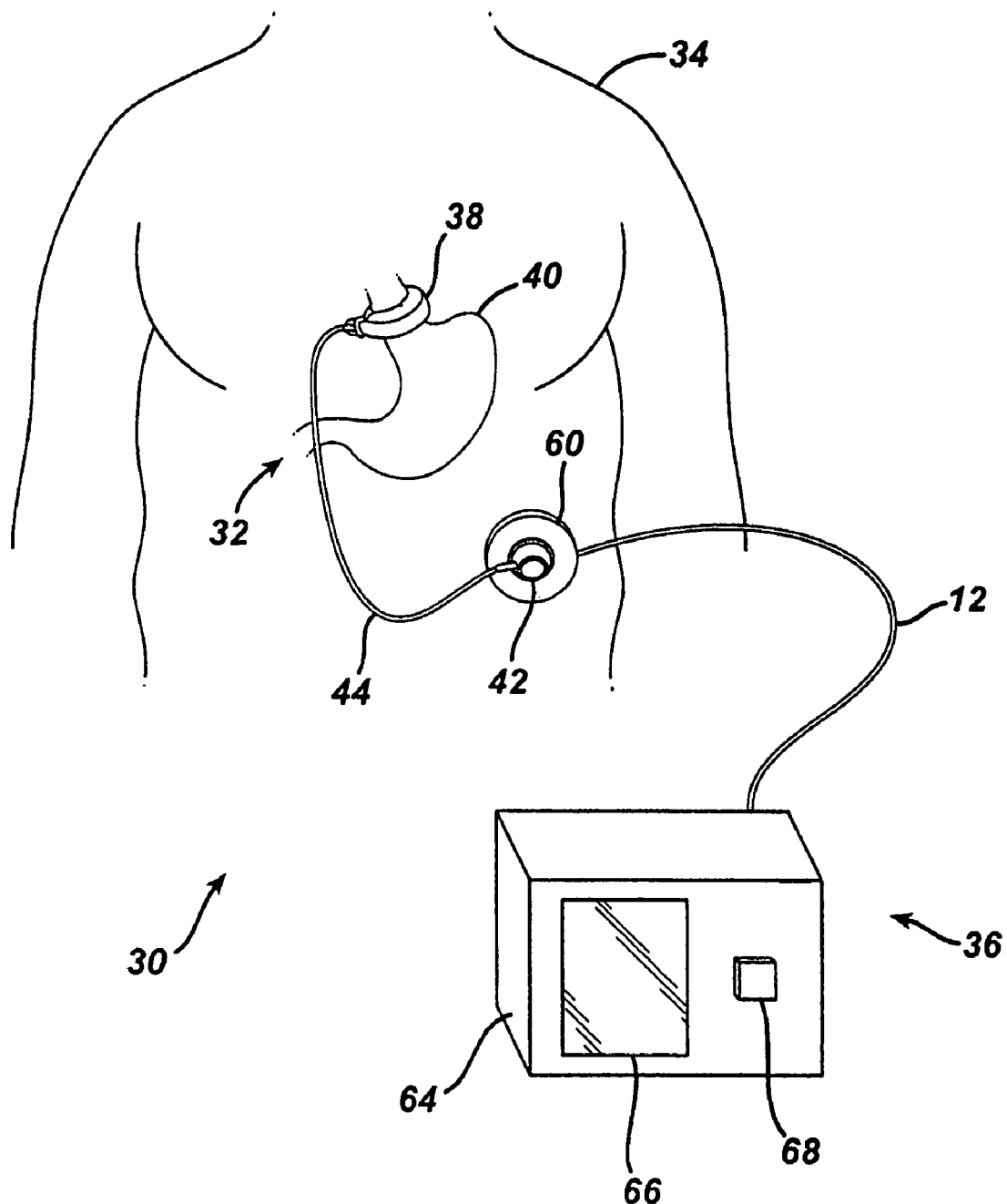
FIG. 1 is a schematic illustration of an exemplary food intake restriction device.

Referring now to the drawings in detail, wherein like numerals indicate the same elements throughout the views, FIG. 1 illustrates a food intake restriction system 30. System 30 comprises a first portion, identified generally as 32, implanted inside of a patient 34, and a second portion, identified generally as 36, located external to the patient. Implanted portion 32 comprises an adjustable gastric band 38 positioned on the upper portion of the patient's stomach 40. Adjustable band 38 may include a cavity made of silicone rubber, or another type of biocompatible material, that inflates inwardly against stomach 40 when filled with a fluid. Alternatively, band 38 may comprise a mechanically adjustable device having a fluid cavity that experiences pressure changes with band adjustments, or a combination hydraulic/mechanical adjustable band. An injection port 42, which will be described in greater detail below, is implanted in a body region accessible for needle injections and/or telemetry communication signals. In the embodiment shown, injection port 42 fluidly communicates with adjustable band 38 via a catheter 44. A surgeon may position and permanently implant injection port 42 inside the body of the patient in order to perform adjustments of the food intake restriction or stoma. Those skilled in the art will recognize that the surgical methods for placing gastric band systems such as implantable portion 32 have evolved greatly during recent years so that the patient may derive optimal therapeutic effect with minimal complications. The surgeon, for example, typically implants injection port 42 in the lateral, subcostal region of the patient's abdomen under the skin and layers of fatty tissue. The surgeon may also implant injection port 42 on the sternum of the patient.

Figure 2:
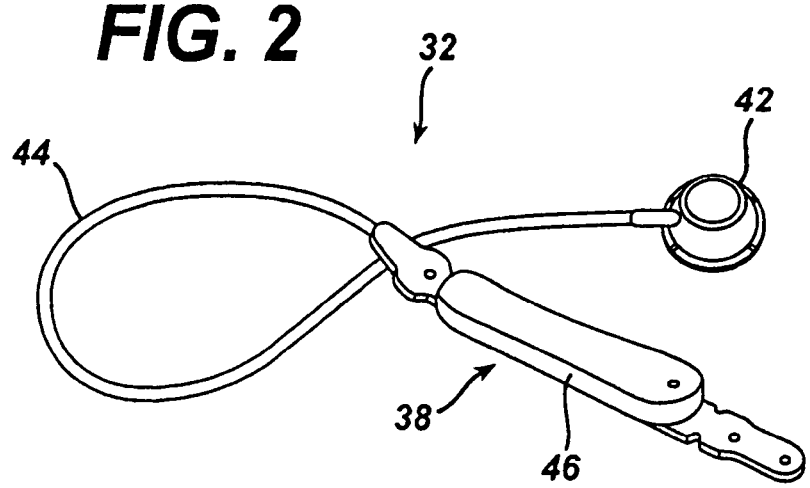
FIG. 2 is a more detailed perspective view of an exemplary implantable portion for the food intake restriction device of FIG. 1.

FIG. 2 illustrates an exemplary adjustable gastric band in greater detail. In this embodiment, band 38 includes a variable volume cavity 46 that expands or contracts against the outer wall of the stomach to form an adjustable stoma for controllably restricting food intake into the stomach. A physician may decrease the size of the stoma opening by adding fluid to variable volume cavity 46 or, alternatively, may increase the stoma size by withdrawing fluid from the cavity. Fluid may be added or withdrawn by inserting a needle into injection port 42. Alternatively, fluid may be transferred in a non-invasive manner between band 38 and injection port 42 using telemetry command signals. The fluid may be, but is not restricted to, a 0.9 percent saline solution.

Figure 3:
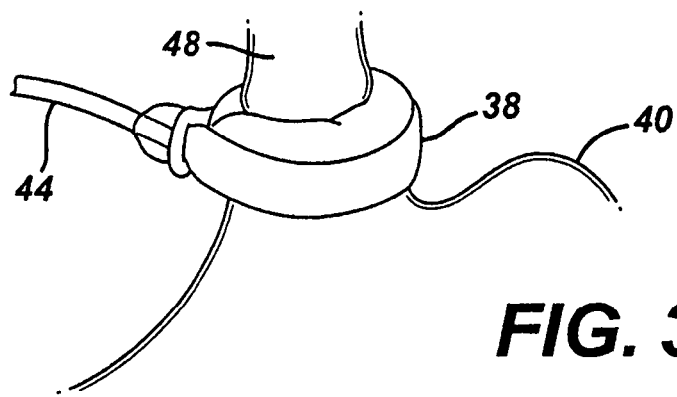
FIG. 3 is a perspective view of the adjustable gastric band of FIG. 2, showing the band positioned around the gastro-esophageal junction of a patient.
Figure 4:
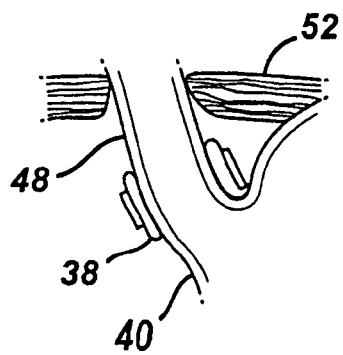
FIG. 4 is a cross-sectional view of the adjustable gastric band of FIG. 2, shown in a deflated configuration.
Figure 5:
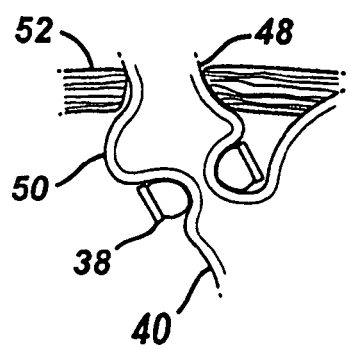
FIG. 5 is a cross-sectional view of the adjustable gastric band of FIG. 2, shown in an inflated configuration to create a food intake restriction.

FIG. 3 shows the adjustable gastric band 38 of FIG. 2 applied about the gastro-esophageal junction of a patient. As shown in FIG. 3, band 38 at least substantially encloses the upper portion of stomach 40 near the junction with esophagus 48. FIG. 4 is a sectional view of band 38, showing the band in a deflated configuration. In this view, band 38 contains little to no fluid, thereby maximizing the size of the stoma opening into stomach 40. FIG. 5 is a cross-sectional view of band 38 and stomach 40, similar to FIG. 4, showing band 38 in an inflated, fluid-filled configuration. In this view, the pressure of band 38 against stomach 40 is increased due to the fluid within the band, thereby decreasing the stoma opening to create a food intake restriction. FIG. 5 also schematically illustrates the dilation of esophagus 48 above band 38 to form an upper pouch 50 beneath the diaphragm muscle 52 of the patient.

Returning now to FIG. 1, external portion 36 of food restriction system 30 comprises a pressure-reading device 60 electrically connected (in this embodiment via an electrical cable assembly 62) to a control box 64. Control box 64 includes a display 66, one or more control switches 68, and an external control module, which will be explained in further detail below. Control box 64 may be configured for use, for example, in a physician's office or examination room. Some ways to mount control box 64 include placement upon a desktop, attachment to an examination table, or hanging on a portable stand. Control box 64 may also be configured for carrying in the physician's lab coat pocket, holding by hand, or placing upon the examination table or the reclining patient. Electrical cable assembly 62 may be detachably connected to control box 64 or pressure-reading device 60 to facilitate cleaning, maintenance, usage, and storage of external portion 36 of system 30. Pressure-reading device 60 non-invasively measures the pressure of the fluid within implanted portion 32 even when injection port 42 is implanted beneath thick (at least over 10 centimeters) subcutaneous fat tissue. The physician may hold pressure-reading device 60 against the patient's skin near the location of injection port 42 in the patient and observe the pressure reading on display 66 of control box 64. Pressure-reading device 60 may also be removably attached to the patient, such as during a prolonged examination, using straps, adhesives, and other well-known methods. Pressure-reading device 60 operates through conventional cloth or paper surgical drapes, and may also include a disposal cover (not shown) that may be replaced for each patient.

Figure 6:
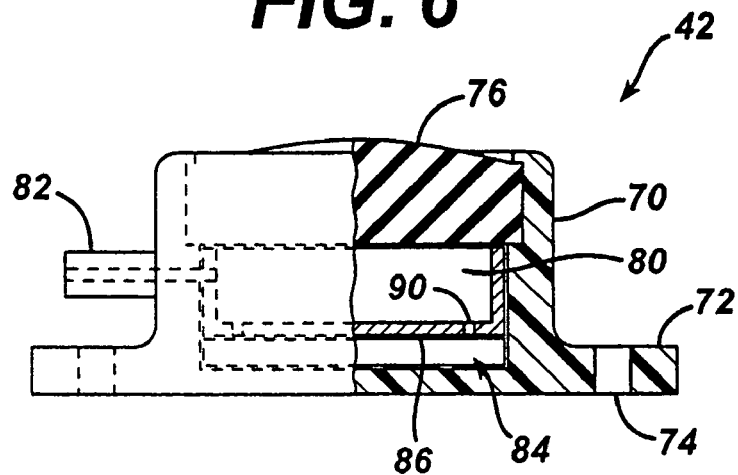
FIG. 6 is a side, partially cross-sectioned view of the injection port shown in FIG. 2.

Turning now to FIG. 6, which depicts a side, partially sectioned view of injection port 42 containing a pressure sensing system for non-invasively measuring the fluid pressure within implanted portion 32. As shown in FIG. 6, injection port 42 comprises a rigid housing 70 having an annular flange 72 containing a plurality of attachment holes 74 for fastening the injection port to tissue in a patient. A surgeon may attach injection port 42 to the tissue, such as the fascia covering an abdominal muscle, using any one of numerous surgical fasteners including suture filaments, staples, and clips. Injection port 42 further comprises a septum 76 typically made of a silicone rubber and compressively retained in housing 70. Septum 76 is penetrable by a Huber needle, or a similar type of injection instrument, for adding or withdrawing fluid from the port. Septum 76 self-seals upon withdrawal of the syringe needle to maintain the volume of fluid inside of injection port 42. Injection port 42 further comprises a reservoir 80 for retaining a working fluid and a catheter connector 82. Connector 82 attaches to catheter 44, shown in FIG. 2, to form a closed hydraulic circuit between reservoir 80 inside of injection port 42 and cavity 46 within adjustable band 38. Fluid from reservoir 80 may be used to expand the volume of band cavity 46. Alternatively, fluid may be removed from cavity 46 and retained in reservoir 80 in order to temporarily decrease the volume of cavity 46. Housing 70 and connector 82 may be integrally molded from a biocompatible polymer or constructed from a metal such as titanium or stainless steel.

A pressure sensing system is provided in injection port 42 to measure the fluid pressure within the closed hydraulic circuit of implanted portion 32. The pressure within the circuit corresponds to the amount of restriction applied by adjustable band 38 to the patient's stomach. Accordingly, measuring the fluid pressure enables a physician to evaluate the restriction created by a band adjustment. Fluid pressure may be measured before, during and/or after an adjustment to verify that the band is properly adjusted. In the embodiment shown in FIG. 6, the pressure sensing system comprises a sensor 84 positioned at the bottom of fluid reservoir 80 within housing 70. A retaining cover 86 extends above pressure sensor 84 to substantially separate the sensor surface from reservoir 80, and protect the sensor from needle penetration. Retaining cover 86 may be made of a ceramic material such as, for example, alumina, which resists needle penetration yet does not interfere with electronic communications between pressure sensor 84 and pressure-reading device 60. Retaining cover 86 includes a vent 90 that allows fluid inside of reservoir 80 to flow to and impact upon the surface of pressure sensor 84.

Figure 7:
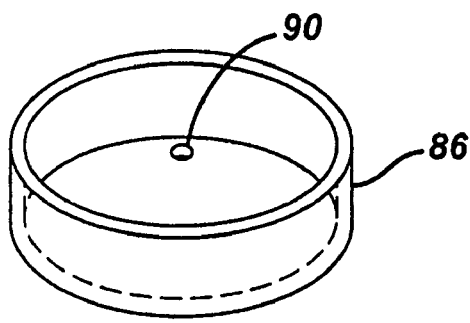
FIG. 7 is an isometric view of the retaining cover shown in FIG. 6.
Figure 8:
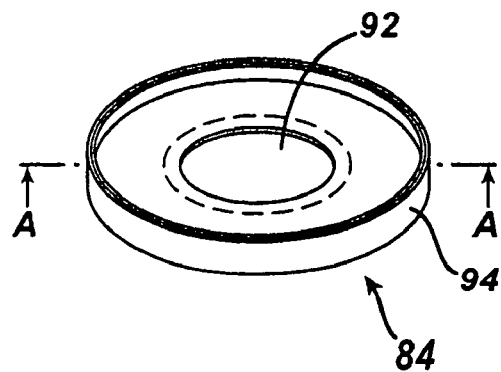
FIG. 8 is an isometric view of the pressure sensor shown in FIG. 6.

FIG. 7 is an isometric view of retaining cover 86 illustrating vent 90 in the bottom surface of the cover. FIG. 8 is an isometric view of the exterior of pressure sensor 84. As shown in FIG. 8, the exterior of pressure sensor 84 includes a strain element having a deformable surface. In the embodiment shown, the strain element is a diaphragm 92. Diaphragm 92 may be formed by thinning out a section of a wall in titanium reservoir 80. Diaphragm 92 may be made of titanium or another similar material, and have a thickness between 0.001" and 0.002". While the embodiments show a diaphragm as the strain element, the present invention may also be constructed and practiced using other strain elements to convert fluid pressure to a mechanical displacement. Examples of other suitable strain elements include, but are not limited to, Bourdon tubes and bellows assemblies. Pressure sensor 84 is hermetically sealed within a housing 94 to prevent fluid infiltrating and effecting the operation of the sensor. Housing 94 is sealed to port housing 70 to prevent the loss of fluid from the injection port 42. Diaphragm 92 is hermetically sealed to sensor housing 94 to prevent fluid from passing around the edges of the diaphragm and into the internal components of the sensing system. As fluid flows through vent 90 in reservoir 80, the fluid impacts upon the surface of diaphragm 92. The fluid flow through vent 90 enables diaphragm 92 to respond to fluid pressure changes within the hydraulic circuit and convert the pressure changes into a mechanical displacement.

Figure 9:
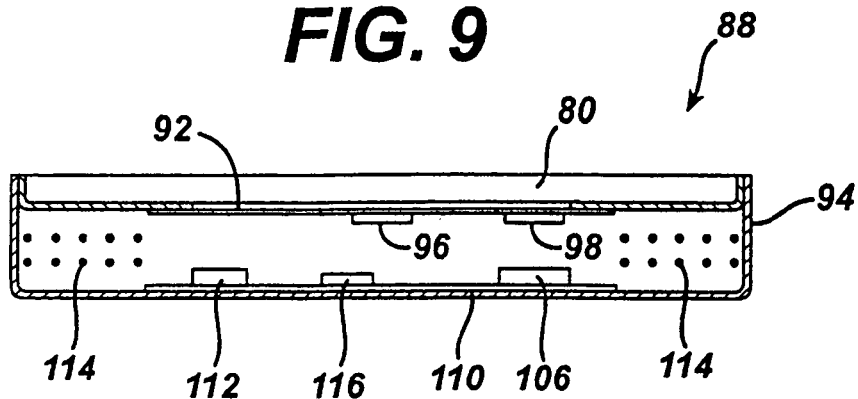
FIG. 9 is a side cross-sectional view illustrating an exemplary pressure sensing system.

FIG. 9 is a side sectional view of pressure sensor 84, taken along line A-A of FIG. 8, illustrating a first embodiment 88 for measuring fluid pressure. In the embodiment shown in FIG. 9, the mechanical displacement of diaphragm 92 is converted to an electrical signal by a pair of variable resistance, silicon strain gauges 96, 98. Strain gauges 96, 98 are attached to diaphragm 92 on the side opposite the working fluid in reservoir 80. Strain gauge 96 is attached to a center portion of diaphragm 92 to measure the displacement of the diaphragm. The second, matched strain gauge 98 is attached near the outer edge of diaphragm 92. Strain gauges 96, 98 may be attached to diaphragm 92 by adhesives, or may be diffused into the diaphragm structure. As the fluid pressure within band 38 changes, the surface of diaphragm 92 deforms up or down within the surface of housing 94. This deformation of diaphragm 92 produces a resistance change in the center strain gauge 96.

Figure 10:
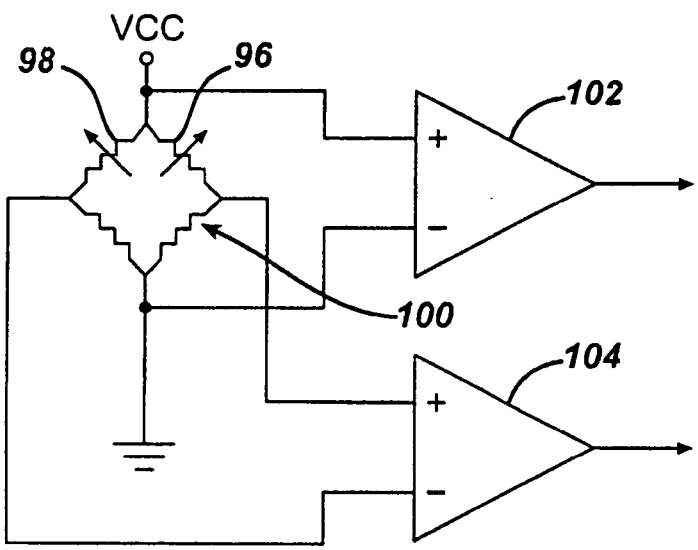
FIG. 10 is a simplified schematic of the variable resistance circuit of pressure sensing system of FIG. 9.

As shown in FIG. 10, strain gauges 96, 98 form the top two resistance elements of a half-compensated, Wheatstone bridge circuit 100. As strain gauge 96 reacts to the mechanical deformations of diaphragm 92, the changing resistance of the gauge changes the potential across the top portion of the bridge circuit. Strain gauge 98 is matched to strain gauge 96 and athermalizes the Wheatstone bridge circuit. Differential amplifiers 102, 104 are connected to bridge circuit 100 to measure the change in potential within the bridge circuit due to the variable resistance strain gauges. In particular, differential amplifier 102 measures the voltage across the entire bridge circuit, while differential amplifier 104 measures the differential voltage across the strain gauge half of bridge circuit 100. The greater the differential between the strain gauge voltages, for a fixed voltage across the bridge, the greater the pressure difference. If desired, a fully compensated Wheatstone bridge circuit could also be used to increase the sensitivity and accuracy of the pressure sensing system. In a fully compensated bridge circuit, four strain gauges are attached to the surface of diaphragm 92, rather than only two strain gauges as shown in FIG. 9.

The output signals from differential amplifiers 102, 104 are applied to a microcontroller 106. Microcontroller 106 is integrated into a circuit board 110 within housing 94. A temperature sensor 112 measures the temperature within the implanted port and inputs a temperature signal to microcontroller 106. Microcontroller 106 uses the temperature signal from sensor 112 to compensate for variations in body temperature and residual temperature errors not accounted for by strain gauge 98. Compensating the pressure measurement signal for variations in body temperature increases the accuracy of the pressure sensing system. Additionally, a TET/telemetry coil 114 is located within housing 94. Coil 114 is connected to a capacitor 116 to form a tuned tank circuit for receiving power from external portion 36, and transmitting the pressure measurement to pressure reading device 60.

Figure 11:
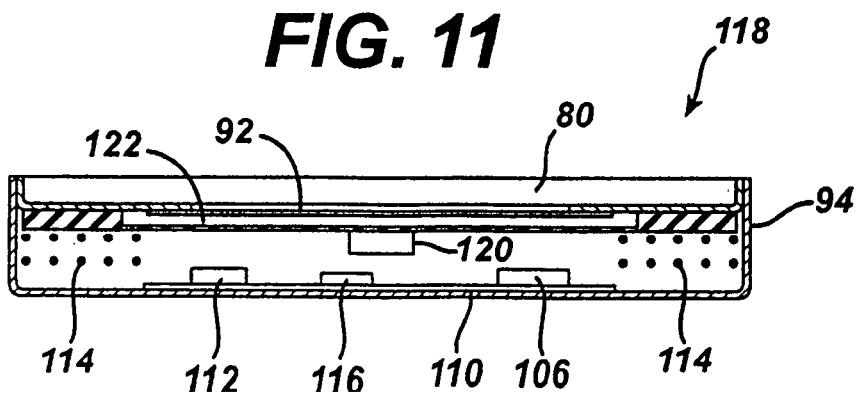
FIG. 11 is a side, cross-sectional view of an alternative exemplary pressure sensing system.

FIG. 11 is a side, sectional view similar to FIG. 9, showing a second embodiment 118 for the pressure sensing system of the present invention. In second embodiment 118, a MEMS sensor 120 is provided within housing 94 to measure the mechanical deformation of diaphragm 92 and produce an electrical signal proportional to the pressure within adjustable band 38. A sealed, silicone oil chamber 122 is provided between diaphragm 92 and MEMS sensor 120. Oil chamber 122 protects MEMS sensor 120 and transfers the mechanical displacements of diaphragm 92 to the sensor. MEMS sensor 120 outputs an electrical signal to microcontroller 106 indicative of the fluid pressure in reservoir 80. Microcontroller 106 inputs the signal from the MEMS sensor 120 and a temperature signal from temperature sensor 112, and calculates the pressure measurement. The pressure measurement is transmitted to pressure reading device 60 in external portion 36 using telemetry signals, as will be described in more detail below.

Figure 12:
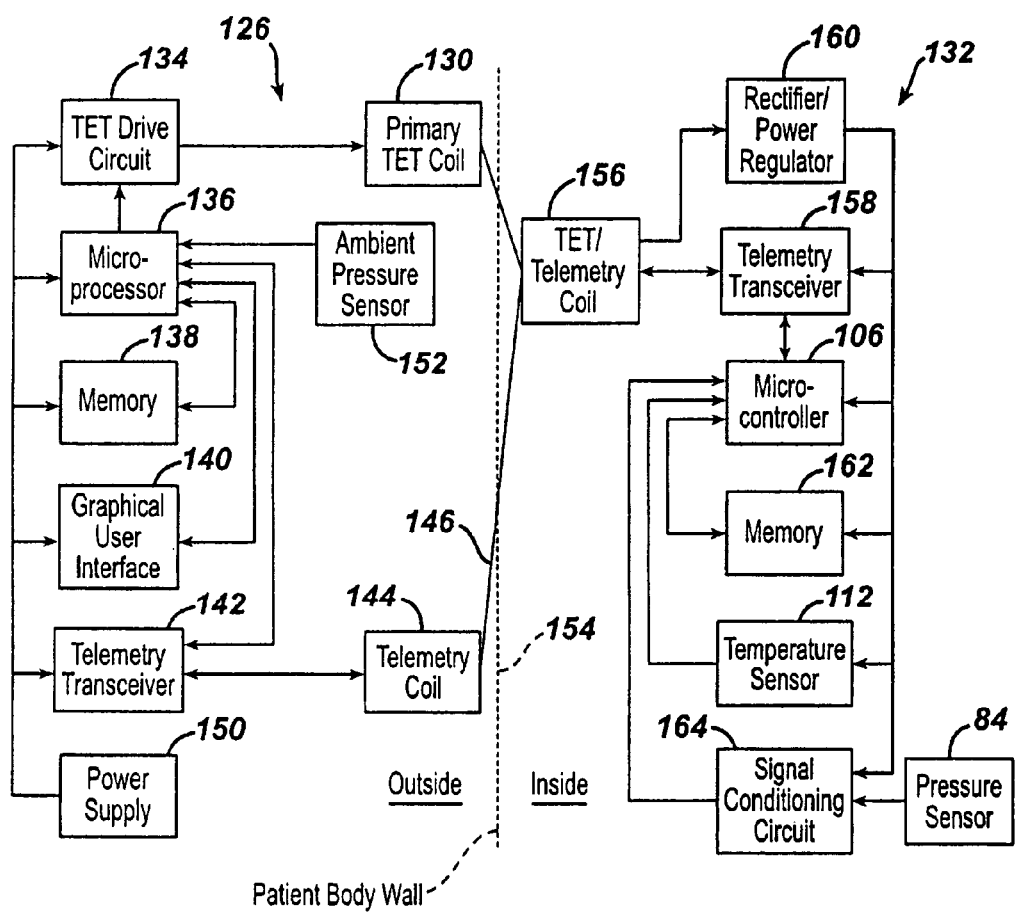
FIG. 12 is a block diagram representing a pressure measurement system associated with the pressure sensing system of FIGS. 9 and 11.

FIG. 12 is a block diagram of a pressure measurement system for first and second embodiments 88, 118 of the invention. As shown in FIG. 12, an external control module 126 of the system includes a primary TET coil 130 for transmitting a power signal to the internal control module, indicated generally as 132. Primary TET coil 130 is located in pressure reading device 60 shown in FIG. 1. A TET drive circuit 134 controls the application of a power signal to primary TET coil 130. TET drive circuit 134 is controlled by a microprocessor 136 having an associated memory 138. A graphical user interface 140 is connected to microprocessor 136 for controlling the data shown on display 66. External control module 126 also includes a primary telemetry transceiver 142 for transmitting interrogation commands to and receiving response data, including fluid pressure readings, from implant control module 132. Primary transceiver 142 is electrically connected to microprocessor 136 for inputting and receiving command and data signals. Primary transceiver 142 resonates at a selected RF communication frequency to generate a downlink alternating magnetic field 146 that transmits command data to implant control module 132. A power supply 150 supplies energy to external control module 126 in order to power system 30. An ambient pressure sensor 152 is connected to microprocessor 136. Microprocessor 136 uses the signal from ambient pressure sensor 152 to adjust the pressure reading for variations in atmospheric pressure due to, for example, variations in barometric conditions or altitude, in order to increase the accuracy of the pressure measurement.

FIG. 12 also illustrates internal control module 132 implanted beneath the patient's skin 154. Internal control module 132 is located within housing 94 of injection port 42. As shown in FIG. 12, a secondary TET/telemetry coil 156 in internal control module 132 receives power and communication signals from external control module 126. Coil 156 forms a tuned tank circuit that is inductively coupled with either primary TET coil 130 to power the implant, or primary telemetry coil 144 to receive and transmit data. A telemetry transceiver 158 controls data exchange with coil 156. Additionally, internal control module 132 includes a rectifier/power regulator 160, microcontroller 106 described above, a memory 162 associated with the microcontroller, temperature sensor 112, pressure sensor 84 and a signal conditioning circuit 164 for amplifying the signal from the pressure sensor. Internal control module 132 transmits the temperature adjusted pressure measurement from pressure sensor 84 to external control module 126. In external module 126, the received pressure measurement signal is adjusted for changes in ambient pressure and shown on display 66.

Figure 13:
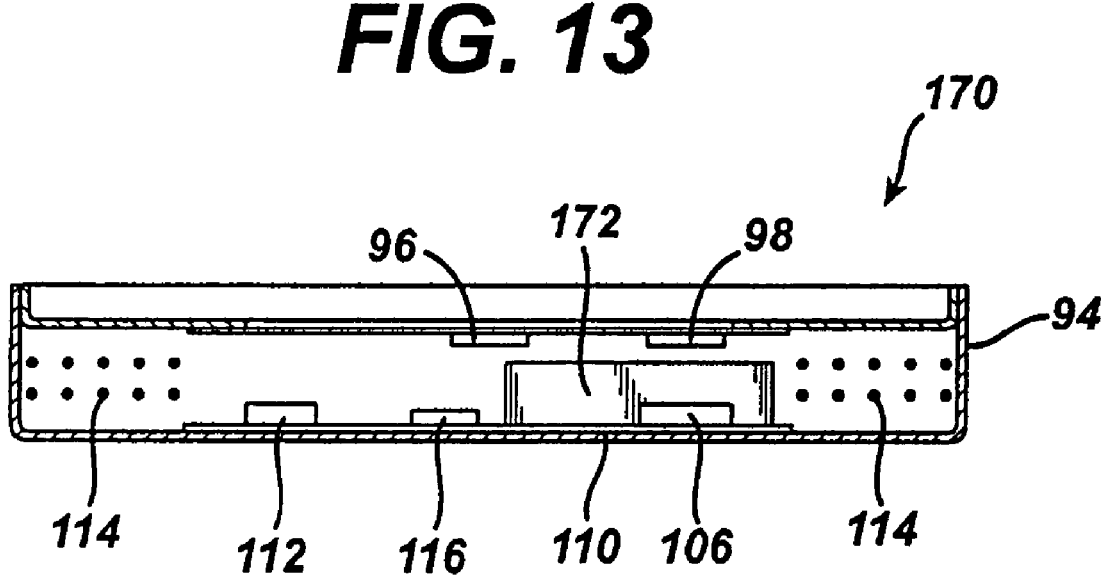
FIG. 13 is a side, cross-sectional view of an alternative exemplary pressure sensing system.

FIG. 13 is a side, sectional view showing a third embodiment 170 for measuring fluid pressure in accordance with the invention. In the third embodiment 170, internal control module 132 is powered by an internal power supply such as, for example, a battery 172. Battery 172 replaces primary and secondary TET coils 130, 156 for powering microcontroller 106 and the other internal components. In this embodiment, the pressure sensing system includes a pair of strain gauges 96, 98 as in first embodiment 88, for measuring the mechanical deformations of diaphragm 92 corresponding to pressure changes in band 38. Strain gauges 96, 98 are incorporated into a balanced, thermally compensated bridge circuit for measuring pressure differentials within the closed fluid circuit of the implant.

Figure 14:
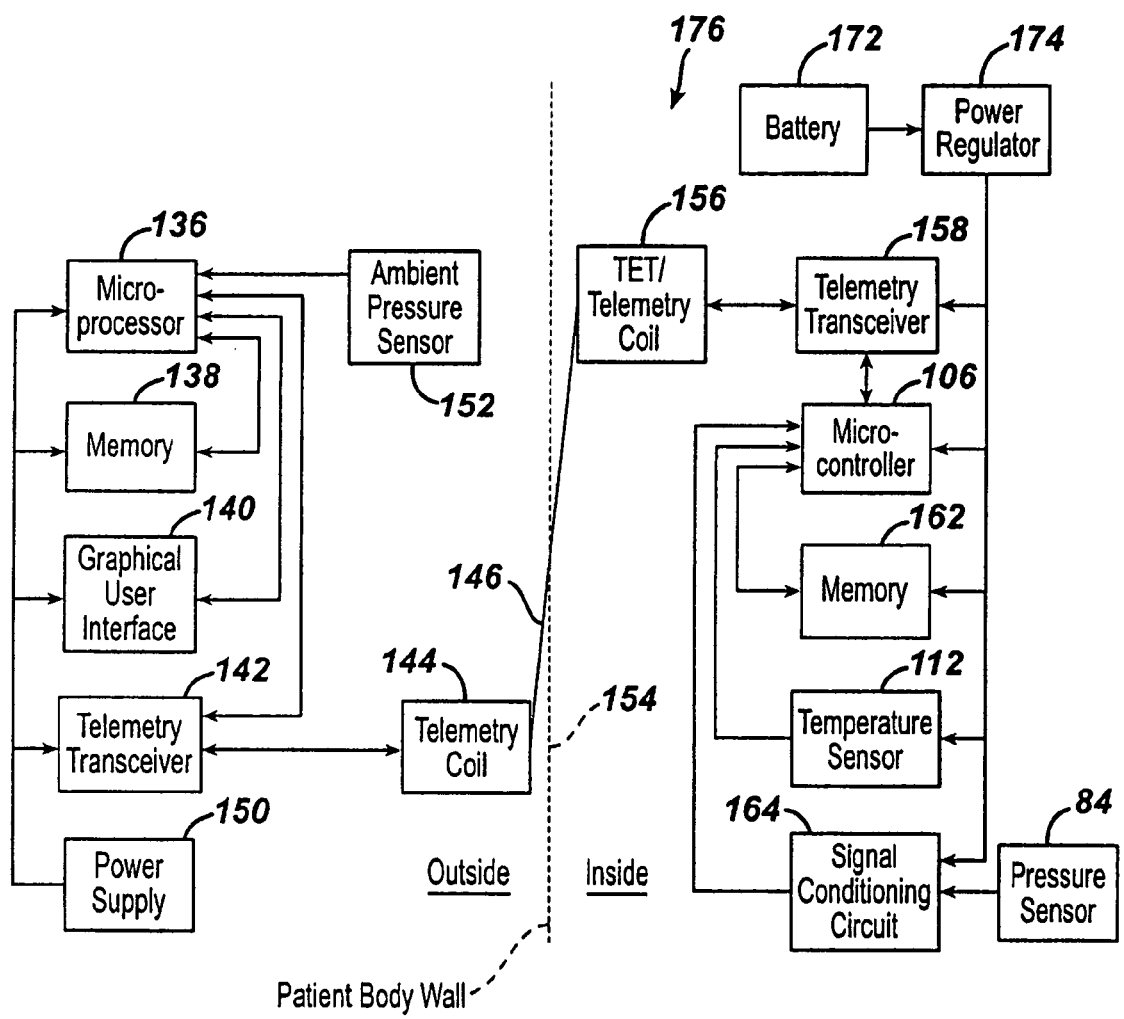
FIG. 14 is a block diagram representing a pressure measurement system associated with the pressure sensing system of FIG. 13.

FIG. 14 is a block diagram of the pressure measurement system of the invention in accordance with the third embodiment 170 shown in FIG. 13. In embodiment 170, an internal power supply is used to power internal control module 176 rather than a TET power system as in the first embodiment. The power source for implanted portion 32 is battery 172 rather than the TET primary coil 130 and secondary coil 156 shown in FIG. 12. In the embodiment shown in FIG. 14, secondary, implanted coil 156 is used solely for data communication between the internal and external control modules. A power regulator 174 is provided to control power from battery 172 in order to conserve and extend the life of the battery.

Figure 15:
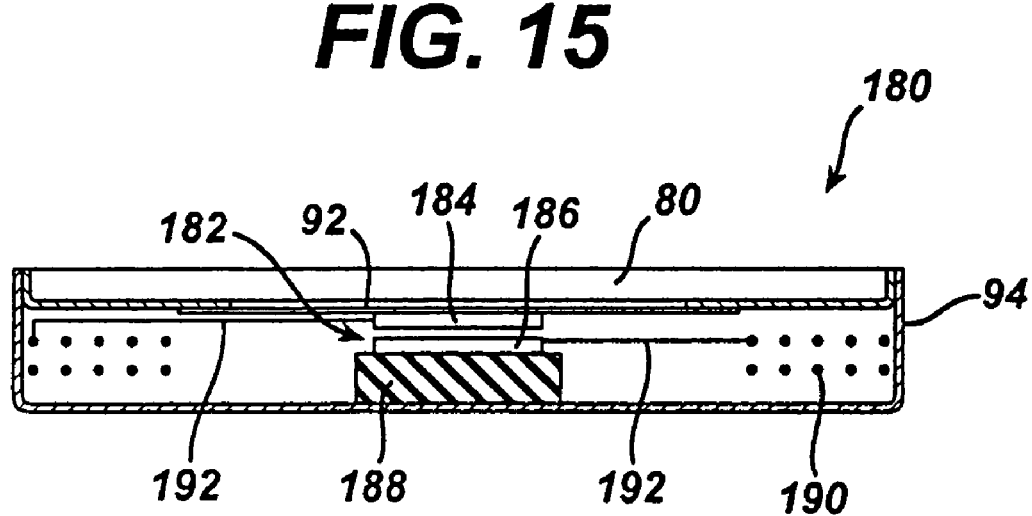
FIG. 15 is a side, cross-sectional view of an alternative pressure sensing system.

FIG. 15 illustrates a fourth embodiment 180 for measuring fluid pressure within adjustable band 38, in which a passive system is utilized for measuring pressure changes within the working fluid. In this fourth embodiment 180, a variable capacitance 182 is attached to diaphragm 92 in order to measure the mechanical deformations of the diaphragm. Variable capacitance 182 includes a first plate 184 attached near the center of diaphragm 92 on the side opposite fluid reservoir 80. A second capacitor plate 186 is fixed in position within housing 94 by a capacitor mount 188. Each of the capacitor plates 184, 186 is connected to an inductance coil 190, as shown by lines 192, to form a resonant circuit. When the fluid pressure within reservoir 80 increases or decreases due to, for instance, changes in the peristaltic pressure against band 38, the position of capacitor plate 184 varies with the deformation of diaphragm 92. As fluid pressure increases, diaphragm 92 pushes first capacitor plate 184 closer to second capacitor plate 186, thereby increasing the capacitance and decreasing the resonant frequency. Likewise, when the hydraulic pressure decreases within the closed implant circuit, first capacitor plate 184 moves with diaphragm 92 in a direction away from second plate 186, thereby decreasing the capacitance within the resonant circuit and increasing the resonant frequency.

Figure 16:
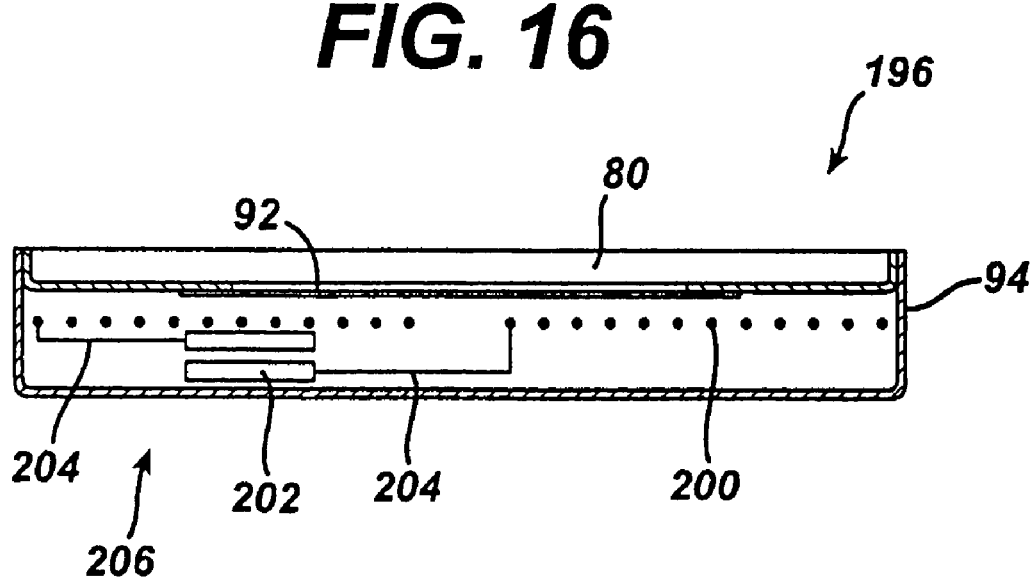
FIG. 16 is a side, cross-sectional view of an alternative pressure sensing system.

FIG. 16 shows a fifth embodiment 196 for measuring fluid pressure in accordance with the present invention. Fifth embodiment 196 is an alternative embodiment for a passive pressure sensing system, in which a variable inductance coil 200 converts the mechanical deformations of diaphragm 92 into a pressure measurement signal. As shown in FIG. 16, inductance coil 200 is a flat coil spaced beneath diaphragm 92. A fixed capacitance 202 is connected to inductance coil 200, as shown by lines 204, to form an LC resonant circuit 206. As diaphragm 92 deforms up and down in response to pressure variations in the working fluid, the inductance of coil 200 varies. As the fluid pressure increases, diaphragm 92 deforms in the direction of coil 200, thereby decreasing the inductance of coil 200 due to eddy current coupling between the metal diaphragm and coil. Conversely, when fluid pressure decreases, diaphragm 92 deforms away from coil 200, thereby decreasing the eddy current coupling and increasing the inductance of the coil. Accordingly, the inductance of coil 200 is inversely proportional to the pressure of the working fluid. As the inductance of coil 200 changes, the resonant frequency of the LC circuit 206 changes.

Figure 17:
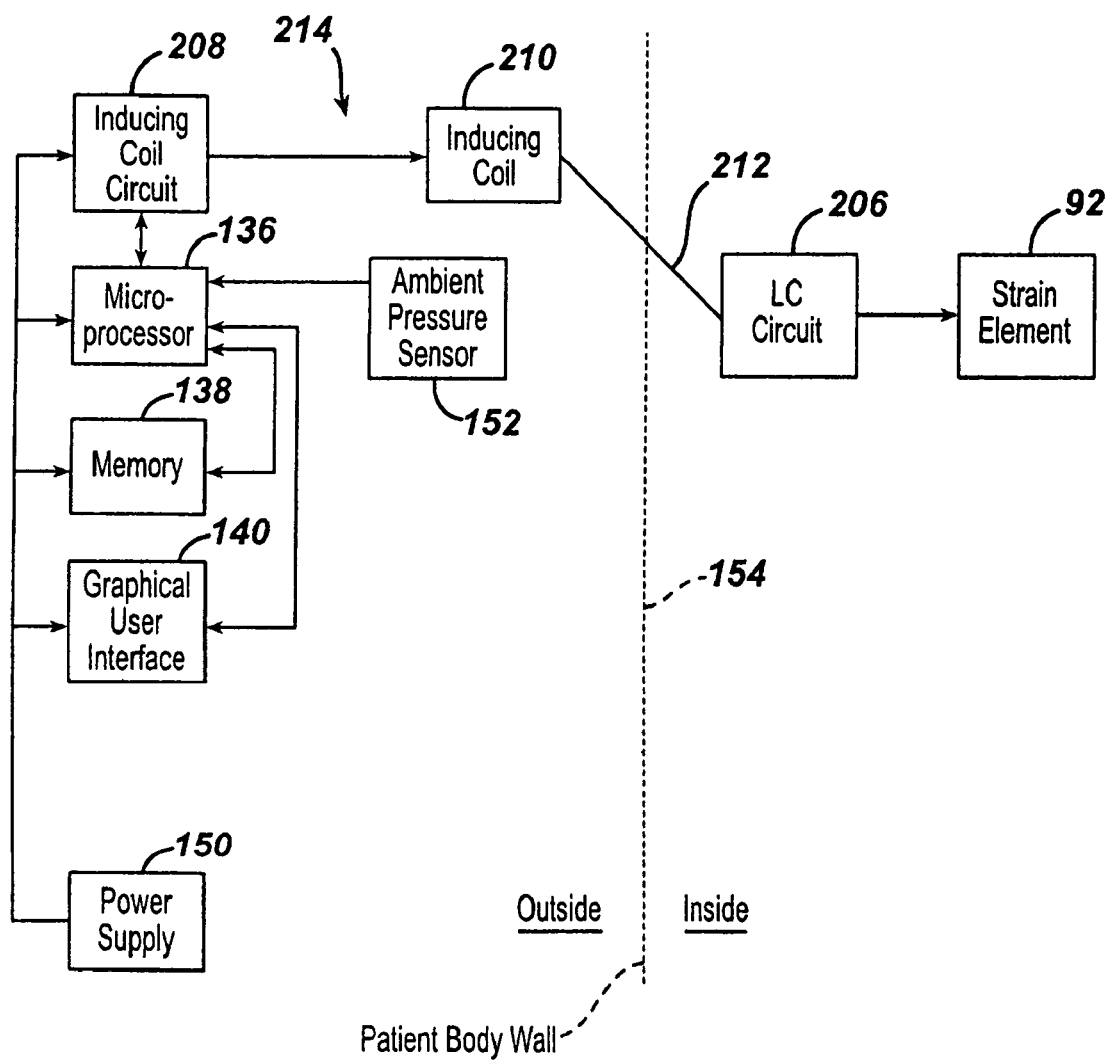
FIG. 17 is a block diagram representing a pressure measurement system associated with the pressure sensing systems of FIGS. 15 and 16.

FIG. 17 is a block diagram of a pressure measurement system for the fourth and fifth embodiments 180, 196 of the invention. In this system, microprocessor 136 controls an inducing coil circuit 208 and inducing coil 210. Microprocessor 136 varies the frequency of inducing coil 210 to magnetically couple the coil with LC circuit 206 in implanted portion 32, as indicated by line 212. The frequency at which the internal and external coils couple will vary with the resonant frequency of the implanted LC circuit 206. The resonant frequency of the implanted LC circuit will vary with the fluid pressure within band 38. The variation in resonant frequency is measured by microprocessor 136 through inducing coil circuit 208. Once detected, the resonant frequency may be compared to known pressures at designated frequencies to determine the fluid pressure within band 38. A graphical user interface 140 in external module 214 displays the measured fluid pressure on display 66.

Figure 18:
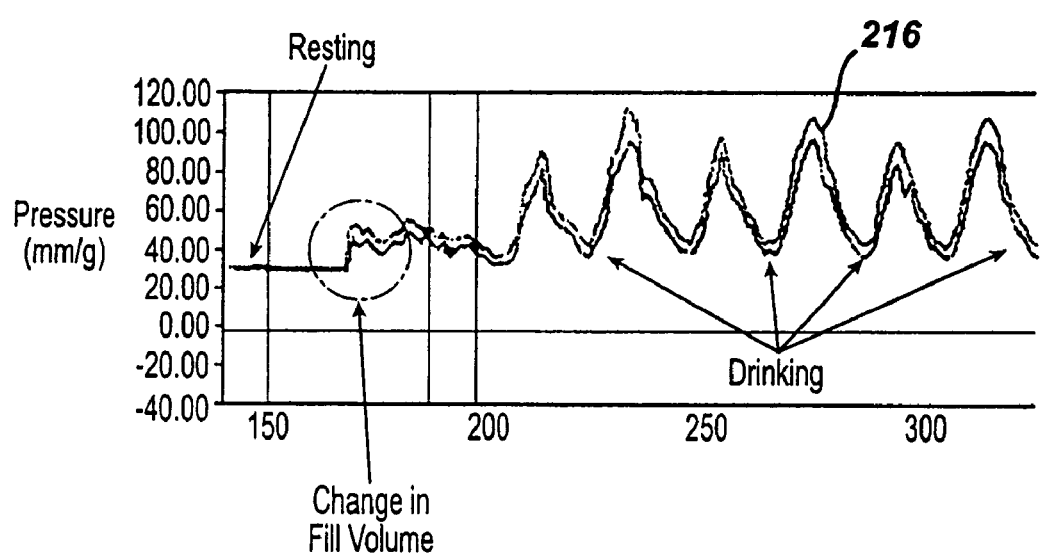
FIG. 18 is a graph indicating a pressure signal from the pressure sensing system, such as may appear on an external monitor display during interrogation by a user.

FIG. 18 is a graphical representation of a pressure signal 216 from the pressure sensing system of the invention, such as may appear on display 66 during interrogation by a user. In the example shown in FIG. 18, the fluid pressure is initially measured by pressure reading device 60 while the patient is stable, resulting in a steady pressure reading as shown. Next, an adjustment is applied to band 38 to decrease the stoma size. During the band adjustment, the pressure sensing system continues to measure the fluid pressure and transmit the pressure readings through the patient's skin to device 60. As seen in the graph of FIG. 18, the pressure reading rises slightly following the band adjustment. In the example shown, the patient is then asked to drink a liquid to check the accuracy of the adjustment. As the patient drinks, the pressure sensing system continues to measure the pressure spikes due to the peristaltic pressure of swallowing the liquid, and transmit the pressure readings to external module 36 for display. By measuring and visually depicting the loading of the restriction device against the peristaltic motion of the stomach both during and after an adjustment, the present invention provides the physician with an accurate, real-time visualization of the patient's response to the adjustment. This instantaneous, active display of recorded pressure data enables the physician to perform more accurate band adjustments. The data may be displayed over time to provide a pressure verses time history.

In addition to use during adjustments, the pressure sensing system of the invention may also be used to measure pressure variations in the restriction device at various intervals during treatment. Periodic pressure readings enable the pressure sensing system to function as a diagnostic tool, to ensure that the food intake restriction device is operating effectively. In particular, the pressure sensing system may be utilized to detect a no pressure condition within the band, indicating a fluid leakage. Alternatively, the system may be used to detect excessive pressure spikes within the band, indicating a kink in catheter 44 or a blockage within the stoma.

The pressure sensing system of the invention also enables a patient to track their own treatment, utilizing an external monitor, such as external device 36, at home. Using the external device, the patient may routinely download pressure readings to their physician's office, thereby reducing the number of office visits required to monitor the patient's treatment. Additionally, the patient could perform pressure readings at home and notify their physician when the band pressure drops below a specified baseline or exceeds a threshold, indicating the need for an adjustment of the device. The pressure sensing system of the invention thus has benefits as both a diagnostic and a monitoring tool during patient treatment with a bariatric device.

Figure 19:
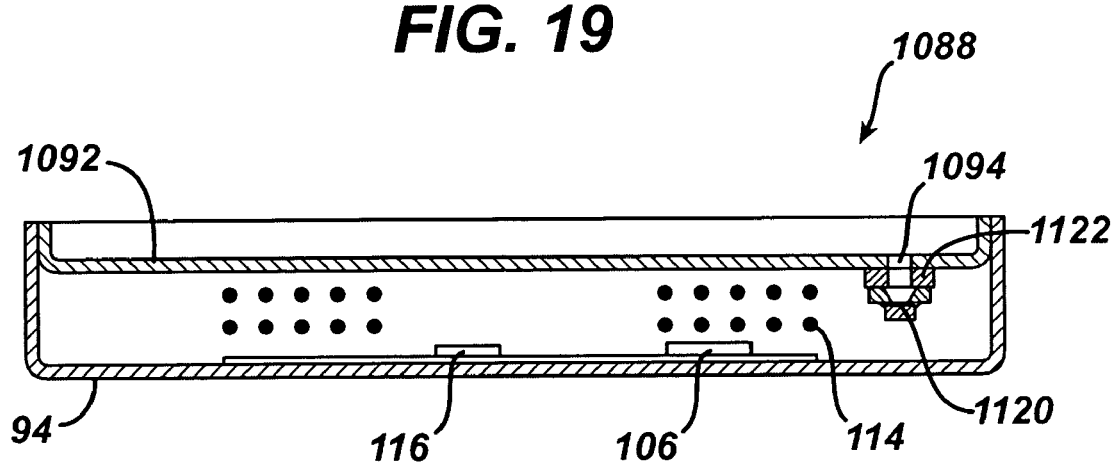
FIG. 19 is a side, cross-sectional view of an alternative exemplary pressure sensing system.
Figure 20:
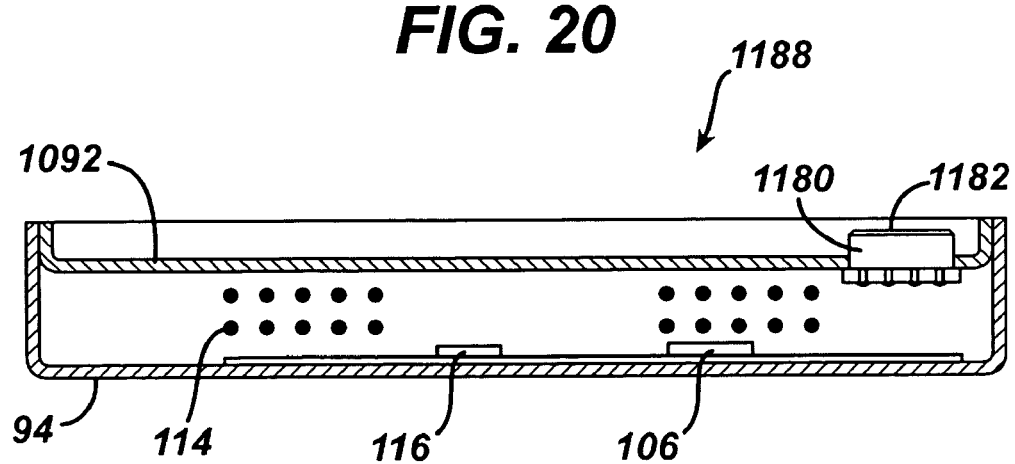
FIG. 20 is a side, cross-sectional view of an alternative exemplary pressure sensing system.

Additional alternative sensor systems 1088, 1188 suitable for incorporation into port 42 are shown in FIGS. 19-20. Each of these pressure sensing systems 1088, 1118 comprise an upper member 1092 and a housing 94. As with pressure sensing system embodiments 88, 118, 170, 180, 196, described above, pressure sensing systems 1088, 1118 may be positioned beneath retaining cover 86 of port 42. Alternatively, upper member 1092 may be integral with retaining cover 86, such that upper member 1092 provides a bottom for retaining cover 86 or reservoir 80. Other suitable configurations will be apparent to those of ordinary skill in the art. In the present example, upper member 1092 is in fluid communication with fluid located within port 42, such that the pressure of such fluid is exerted against upper member 1092. Each of these pressure sensing systems 1088, 1118 further comprise a microcontroller 106, a TET/telemetry coil 114, and a capacitor 116. Each of these pressure sensing systems 1088 may further comprise a temperature sensor (not shown). Microcontroller 106, TET/telemetry coil 114, and capacitor 116 may be configured and may function in a manner similar to the configuration and function of these components 106, 114, 116 described above.

In the embodiment of pressure sensing system 1088 depicted in FIG. 19, a fluid access port 1094 is provided in upper member 1092, and is in fluid communication with a pressure sensor 1120. A hermetic seal 1122 secures pressure sensor 1120 to the bottom of upper member 1092. Pressure sensor 1120 is configured to sense pressure of fluid adjacent to upper member 1092, which is communicated to pressure sensor 1120 via fluid access port 1094. Pressure sensor 1120 is further in communication with microcontroller 106, such that pressure measurements obtained using pressure sensor 1120 may be communicated to or through microcontroller 106 and thus via coil 114 to an external telemetry device.

In the embodiment of pressure sensing system 1188 depicted in FIG. 20, a pressure sensor 1180 having a can-like configuration is positioned within upper member 1092, and protrudes above upper member 1092. Pressure sensor 1180 has a metal cap 1182 that acts as a diaphragm, and is hermetically sealed. Pressure sensor 1180 and/or cap 1182 may also be hermetically sealed relative to adjacent conductive and/or electronic components to provide electrical isolation. Like pressure sensor 1120, pressure sensor 1180 is configured to sense pressure of fluid adjacent to upper member 1092. Similarly, pressure sensor 1180 is further in communication with microcontroller 106, such that pressure measurements obtained using pressure sensor 1180 may be communicated to or through microcontroller 106 and thus via coil 114 to an external telemetry device. It will be appreciated that pressure sensor 1180 may further comprise silicon oil or gel to facilitate uniformity of pressure transfer from cap 1182, to facilitate electrical isolation of pressure sensor 1180, or for any other purpose. Alternatively, any substitute for silicon oil or gel may be used, or the same may be omitted altogether.

Figure 21:
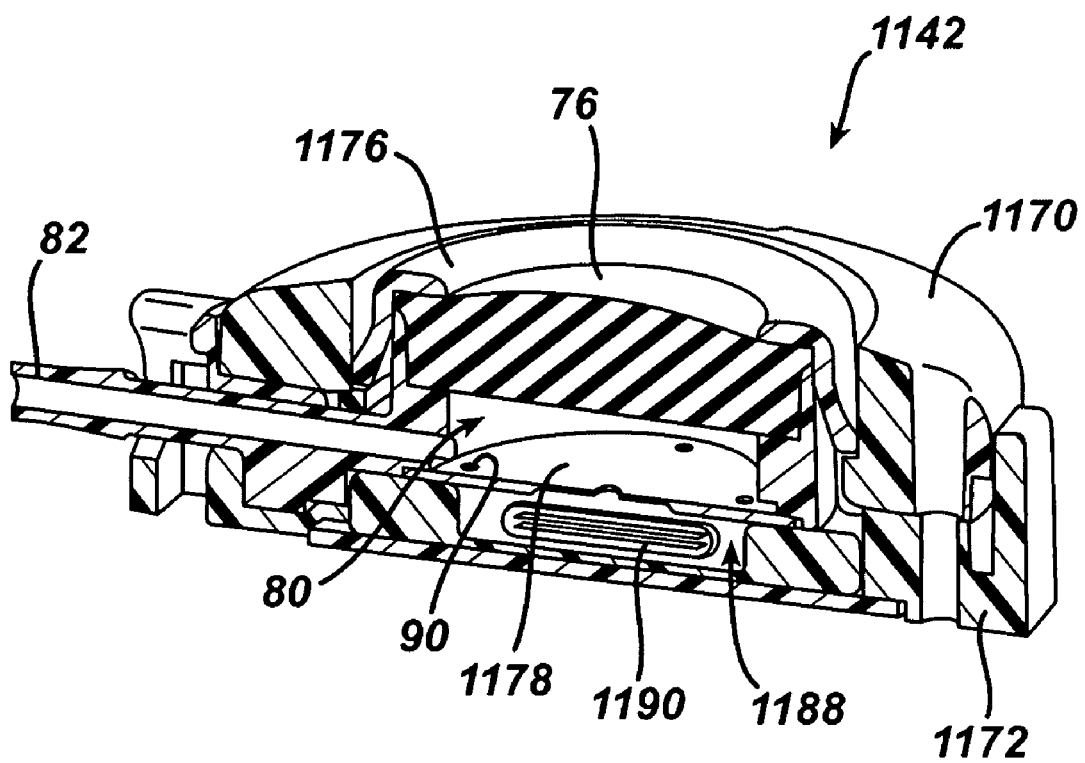
FIG. 21 is a perspective, cross-sectional view of an alternative exemplary pressure sensing system.
Figure 22:
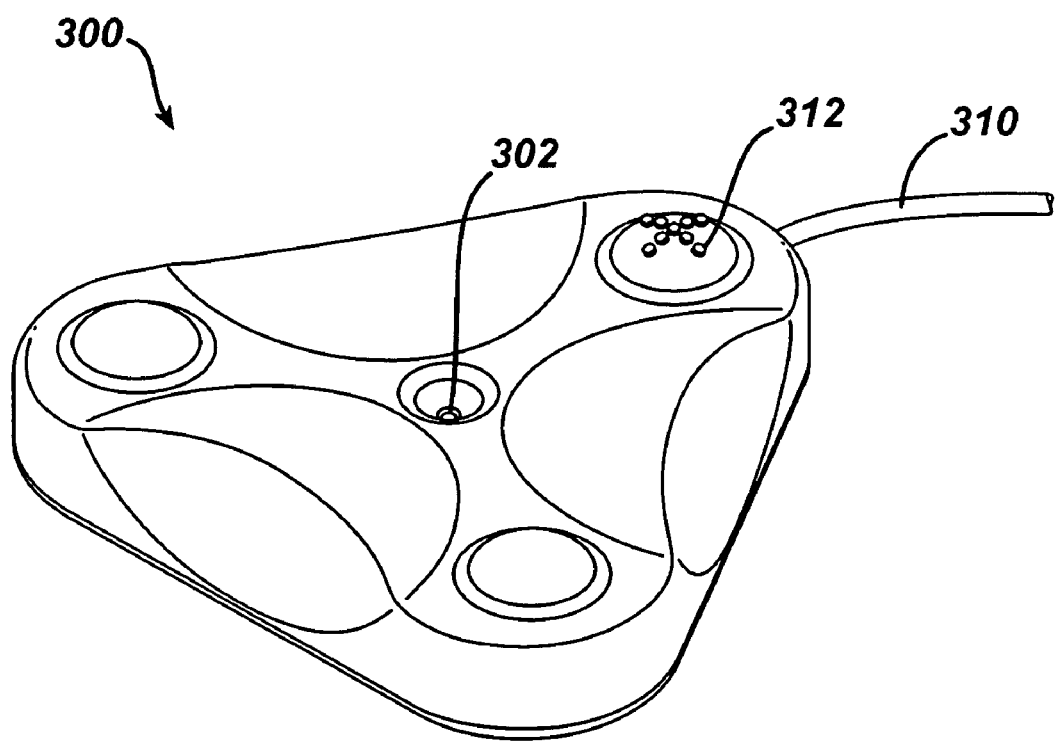
FIG. 22 is a perspective view of an exemplary sense head.
Figure 23:
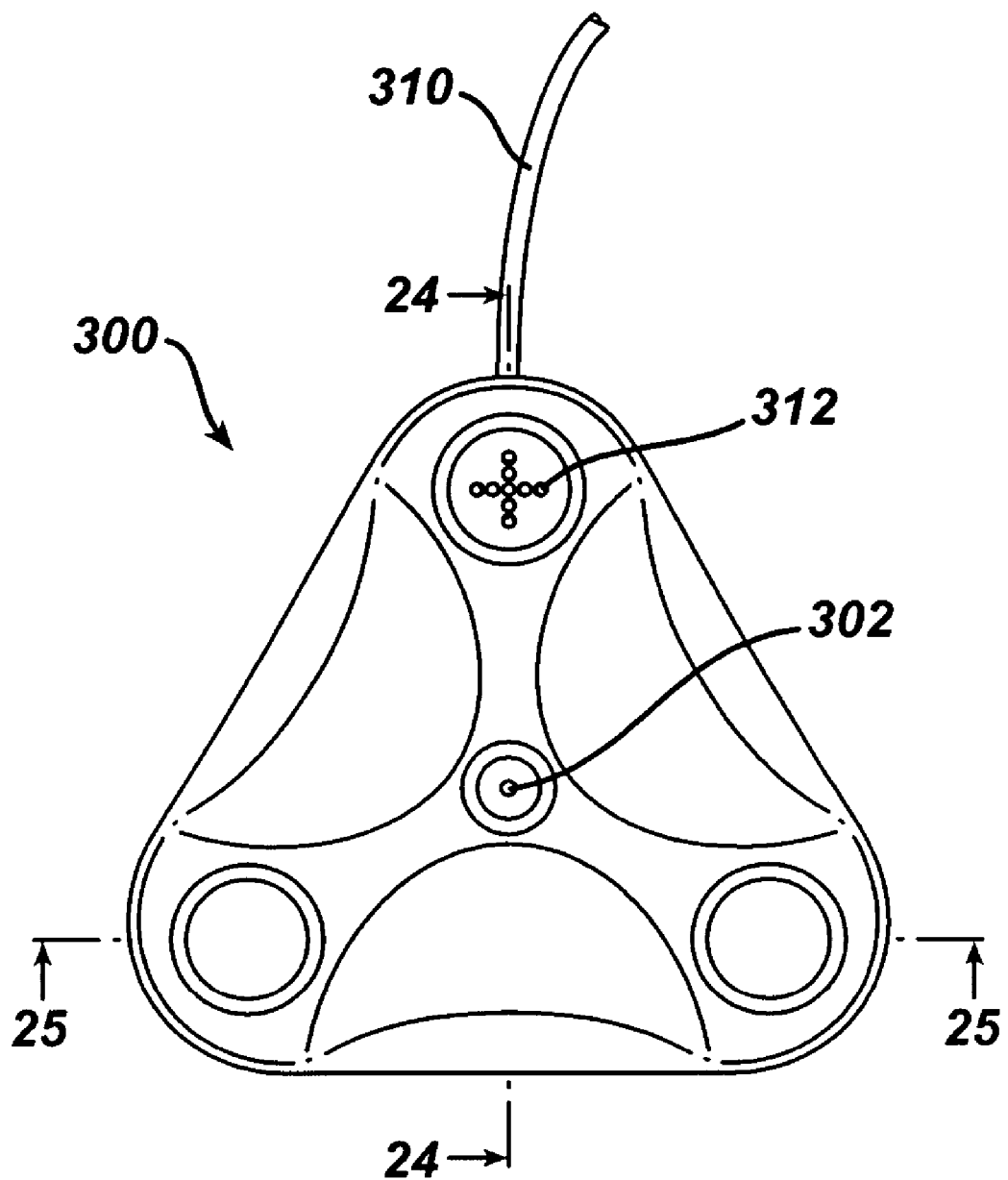
FIG. 23 a plan view of the sense head of FIG. 22.
Figure 24:
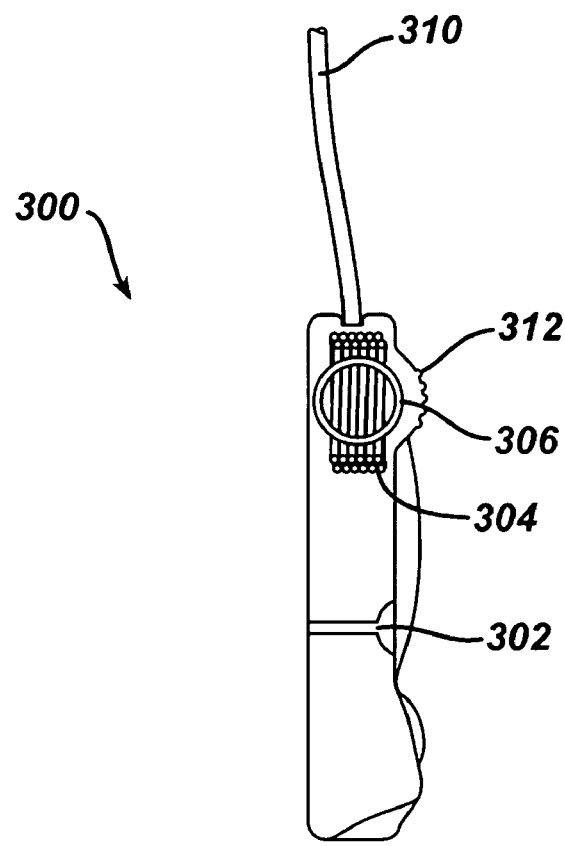
FIG. 24 is a side, cross-sectional view of the sense head of FIG. 23, taken along line 24-24.
Figure 25:
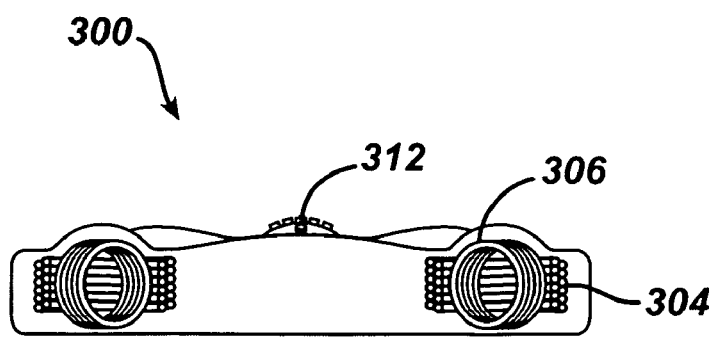
FIG. 25 is a side, cross-sectional view of the sense head of FIG. 23, taken along line 25-25.

FIG. 21 shows another exemplary port 1142. Port 1142 of this example comprises an upper housing 1170, which is secured to a lower housing 1172. Port 1142 further comprises a septum 76 and a retainer 1176. Retainer 1176 is secured to upper housing 1170, and is configured to retain septum 76. Port 1142 further comprises a reservoir 80 and a catheter connector 82 in fluid communication with reservoir 80. A plate 1178 is positioned at the bottom of reservoir 80, and has a plurality of vents 90 formed therethrough. A pressure measurement chamber 1188 is located beneath plate 1178, and is in fluid communication with reservoir 80 via vents 90. A pressure sensor 1190 is positioned within pressure measurement chamber 1188, and is operable to measure the pressure of fluid within port 1142.

In one embodiment, pressure sensors 1120, 1180, 1190 each comprise a wireless pressure sensor provided by CardioMEMS, Inc. of Atlanta, Georgia, though a suitable MEMS pressure sensor may be obtained from any other source. In one example, MEMS pressure sensor 1190 comprises a pressure sensor described in U.S. Pat. No. 6,855,115, the disclosure of which is incorporated by reference herein for illustrative purposes only. In the present example, each pressure sensor 1120, 1180, 1190 is configured to wirelessly communicate pressure data to an external telemetry device. In another embodiment, pressure sensors 1120, 1180, 1190 each comprise a silicon dye. Of course, any other type of pressure sensor may be used. To the extent needed or otherwise desired, port 1142 shown in FIG. 21 may further comprise any additional components, including but not limited to a TET/telemetry coil, a capacitor, a microcontroller, a battery, etc. (not shown). Still other variations will be apparent to those of ordinary skill in the art.

FIGS. 22-25 show an exemplary sense head 300, which is operable to externally sense the location and orientation of port 42, 1142. Sense head 300 of this example comprises a needle window 302, a set of horizontal coils 304, a set of vertical coils 306, a TET coil (not shown), and a cable 310. The TET coil is wrapped around a generally triangular bobbin (not shown), though any other configuration may be used. In the present example, the TET coil is tuned in parallel with a low ESR capacitor at 50 kHz to form a parallel tuned tank circuit. Coil 114 of port 42 is tuned in series with a capacitor such that the resonant impedance is minimized at a resonant frequency of 50 kHz. With an input power of 5 W on the TET coil, coil 114 may deliver approximately 10 mW of power. Of course, any other configurations and parameters may be used.

Each vertical coil 306 of sense head 300 is positioned perpendicularly within a corresponding horizontal coil 304. While three horizontal coils 304 and three vertical coils 306 are shown, it will be appreciated that any suitable number of coils 304, 306 may be used. In addition, while the coils 304, 306 are shown as being in a generally triangular arrangement, it will be appreciated that any other suitable arrangement or configuration may be used. Cable 310 is in communication with coils 304, 306, and is further in communication with a display device 350 as will be described in greater detail below. Of course, sense head 300 may be in communication with any other external device via wire, wirelessly, or otherwise.

Sense head 300 of the present example is configured to communicate with an injection port, such as injection port 42 by way of example only. It will be appreciated that sense head 300 may communicate with any other injection port or device, including but not limited to alternative ports described herein and variations thereof. It will be understood after reviewing the discussion herein, however, that with some embodiments, the type or amount of metal within a port may have an adverse effect on operation of the port and/or sense head 300. For instance, such effects may be in the form of undesirable eddy currents, to the extent that eddy currents are undesirable. To the extent that a metal port housing provides undesirable results it will be appreciated that a coil 114 may be positioned outside of such metal and hermetically wired to a pressure sensor 87 or to other port components. However, such measures are not necessary with port 42 of the present example.

In the present example sense head 300 is operable to provide power to port 42 via the TET coil. Sense head 300 is also operable to detect the position and orientation of port 42, as will be described in greater detail below. Furthermore, sense head 300 is operable to receive pressure data and other data communicated from port 42 in a manner similar to pressure reading device 60, described above. While location, orientation, and pressure-related communications will be described in greater detail below, those of ordinary skill in the art will appreciate that any other types of information may be communicated between port 42 and sense head 300 in any other suitable manner.

In one exemplary use, sense head 300 is placed adjacent to a patient 34 in a region generally near port 42. As will be described in greater detail below, sense head 300 may be used to determine the location and orientation of port 42, thereby permitting a user to position sense head 300 directly over or sufficiently near port 42. When sense head 300 is so positioned, the user may insert a needle 430 of syringe 400 through needle guide 302 of sense head 300 and reach septum 76 of port 42 on the first try. The user may then use syringe 400 to adjust the pressure of fluid within implanted portion 32.

With sense head 300 placed in an initial position, horizontal coils 304 are configured to sense an RF signal provided by coil 114 in port 42. It will be appreciated that characteristics of such RF signal may vary as a function of the position of sense head 300 relative to port 42. Display device 350 may receive indications of such RF signals from each horizontal coil 304, and may process these signals through a logic operable to compare the signal picked up at each horizontal coil 304. Sense head 300 may thus be used to determine the position of port 42 through triangulation. For instance, when sense head 300 is positioned directly over port 42, the three received signals may have an approximately equal amplitude, and a phase shift of approximately zero. It will be appreciated, however, that it may not be possible to position sense head 300 such that the RF signal sensed at each horizontal coil 304 has equal amplitude and a zero phase shift relative to the RF signal as sensed at the other horizontal coils 304. Accordingly, sense head 300 may be moved around adjacent patient 34 until the differences between the amplitudes and phases of the RF signal sensed at horizontal coils 304 are minimized.

As will be described in greater detail below, a display device 350 may further comprise a logic operable to provide a visual representation to the user indicating the relative positioning of sense head 300 and port 42, and further provide a particular indication when sense head 300 is positioned directly over port 42.

Sense head 300 may further comprise a feature operable to visually display location information. In the present example, sense head 300 comprises a plurality of LEDs 312, which are arranged in a "plus sign"-like configuration. LEDs 312 may provide a visual indication to the user as to the relative positioning of sense head 300 and port 42. In particular, lit LEDs 312 may represent position of port 42 relative to sense head 300. For instance, if sense head 300 needs to be moved down and to the right in order to be positioned directly over port 42, the right-most and lower-most LEDs 312 may be lit. As sense head 300 is moved closer to being located directly over port 42, LEDs may provide feedback indicating such proximity as sense head 300 is moved, until the center LED 312 is lit to indicate that sense head 300 is positioned generally over port 42. When the center LED 312 is lit, the user may then desire to refer to display device 350, as will be described in greater detail below, to further adjust positioning of sense head 300. To the extent that LEDs 312 are used, such LEDs 312 may be arranged in any suitable configuration other than a "plus sign." Such alternative configurations may comprise a Cartesian representation, a polar representation, a numerical representation, or any other type of representation. By way of example only, a star or compass rose configuration may be used. In another embodiment, an array of LEDs 312 are provided, and are operable to be selectively lit in the form of an arrow indicating direction. The length of such an arrow may further be varied to indicate distance. It will also be appreciated that additional LEDs 312 may be used to increase spatial resolution of distance and/or direction indicated by such LEDs 312. Of course, any suitable alternative to LEDs 312 may be used, including but not limited to an LCD screen or other display.

In one embodiment, a logic configured to process signals received by horizontal coils 304 to provide positioning feedback through LEDs 312 resides within sense head 300. In another embodiment, such logic resides in display device 350, and is communicated to LEDs 312 in part through cable 310. In still another embodiment, the logic for driving LEDs 312 resides within both sense head 300 and display device 350. Still other suitable locations for logic to drive LEDs 312, and other ways in which LEDs 312 may be driven, will be apparent to those of ordinary skill in the art. It will also be appreciated that, as with any other component and feature described herein, LEDs 312 may simply be omitted altogether.

With sense head 300 placed in an initial position adjacent to a patient 34 in a region generally near port 42, vertical coils 306 configured to sense an RF signal provided by coil 114 in port 42. It will be appreciated that characteristics of such RF signal may vary as a function of the orientation (e.g., pitch, yaw, roll, attitude, etc.) of sense head 300 relative to port 42. Display device 350 may receive indications of such RF signals from each vertical coil 306, and may process these signals through a logic operable to compare the signal picked up at each vertical coil 306. When sense head 300 is oriented parallel with port 42, the three received signals may have an approximately equal amplitude, and a phase shift of approximately zero. As will be described in greater detail below, display device 350 may further comprise a logic operable to provide a visual representation to the user indicating the relative orientation of sense head 300 and port 42, and further indicate when sense head 300 is oriented substantially parallel with port 42.

In another embodiment, sense head 300 and port 42 are configured such that orientation characteristics may detected based on the phase relationship between signals emitted by coil 114 and within sense head 300 (e.g., a launch/drive signal from a TET coil in sense head 300). For instance, if the signals are in phase, such a relationship may indicate that port 42 is oriented parallel with sense head 300 and that septum 76 is facing sense head 300; whereas the signals being 90° out of phase may indicate that port 42 is perpendicular to sense head 300; while the signals being 180° out of phase may indicate that port 42 is flipped over relative to sense head 300 (e.g., septum 76 is facing inward toward the center of patient 34). Other orientations may be detected based on corresponding phase relationships. Alternatively, coil 114 in port 42 may emit a pattern of pulses when sense head 300 is passed over port 42, such as two short pulses followed by a longer pulse (e.g., about 3-4% longer than the short pulses) when port 42 is right side up. When port 42 is flipped 180°, the pattern may be reversed. Sense head 300 may receive these signals, and sense head 300 or any other device (e.g., display device 350, etc.) may process such signals, such that the user may be provided with an audio or visual indication relating to the orientation of port 42. Accordingly, it will be appreciated that vertical coils 306 are not necessarily needed to obtain orientation information. Other suitable structures and techniques for determining orientation information will be apparent to those of ordinary skill in the art.

Figure 26:
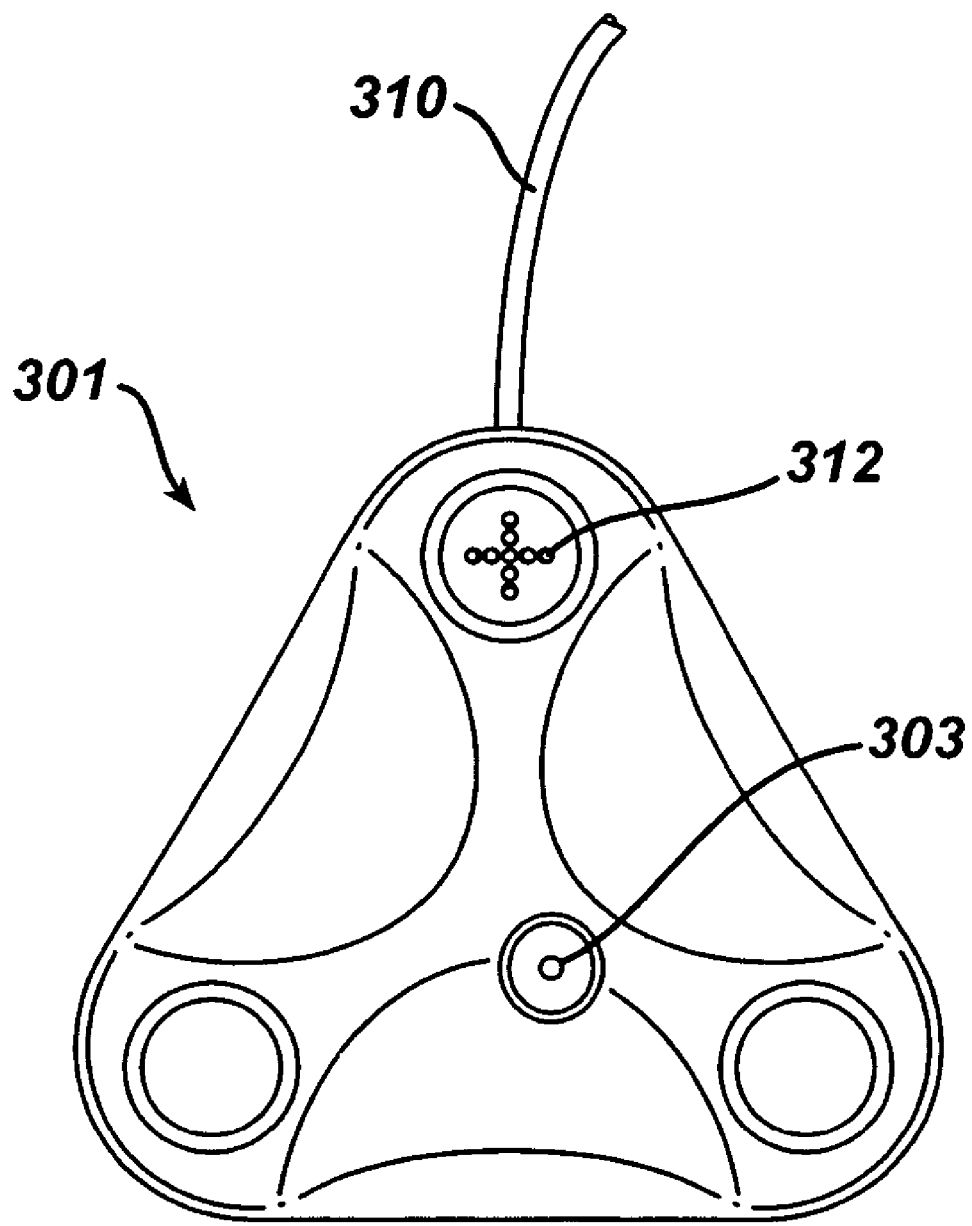
FIG. 26 is a plan view of an alternative exemplary sense head.

An alternative sense head 301 is shown in FIG. 26. In this variation, needle window 303 is offset from the center of sense head 301, but is otherwise configured similar to sense head 300. Such an offset of needle window 303 may reduce the likelihood that the housing of sense head 301 will physically interfere with external anatomical structures of patient 34 where such interference would otherwise create difficulties in positioning the centered needle window 302 of sense head 300 over port 42. The offset of needle window 303 as shown in FIG. 26 is merely exemplary, and it will be appreciated that needle window 303 may be located elsewhere (e.g., proximate to an edge or corner of the housing of sense head 301, etc.). It will also be appreciated that, with needle window 303 not being positioned at the center of sense head 301, needle window 303 will not be positioned at the collective center of the arrangement of horizontal coils 304 and vertical coils 306. Nevertheless, coils 304, 306 may still be used to determine the relative positioning of needle window 303 and port 42 using techniques similar to those employed with sense head 300. For instance, a corrective constant (e.g., a vector) may be factored into an algorithm used to process RF signals sensed by coils 304, 306. Such a corrective constant may represent the displacement (e.g., in terms of distance and direction) of needle window 303 relative to the center of sense head 301 (or relative to the center of the arrangement of coils 304, 306). Various ways in which such a corrective constant may be factored into the algorithm will be apparent to those of ordinary skill in the art.

By way of example only, the position of the center of sense head 301 relative to port 42 may first be found by comparing RF signals (e.g., in terms of phase and amplitude) received by horizontal coils 304 (thereby obtaining a "determined position"). The corrective constant may then be added to that determined position to further determine the position of needle window 303 relative to port 42. Alternatively, the properties of RF signals received by coils 304 may have one or more characteristic disparities (or one or more characteristic disparity ranges) when needle window 303 is positioned directly over port 42, such that the algorithm may treat that disparity in a manner similar to the minimized phase and amplitude differences of RF signals received by coils 304 in sense head 300. In other words, the algorithm may treat such disparity as a target to be reached. The characteristic disparities in the properties of RF signals sensed by horizontal coils 304 when needle window 303 is positioned directly over port 42 may be a function of the displacement of the needle window 303 relative to sense head 301, such that the characteristic disparities may be predetermined. Of course, any other techniques or structures suitable for determining the position of needle window 303 relative to port 42 may be used.

Figure 27:
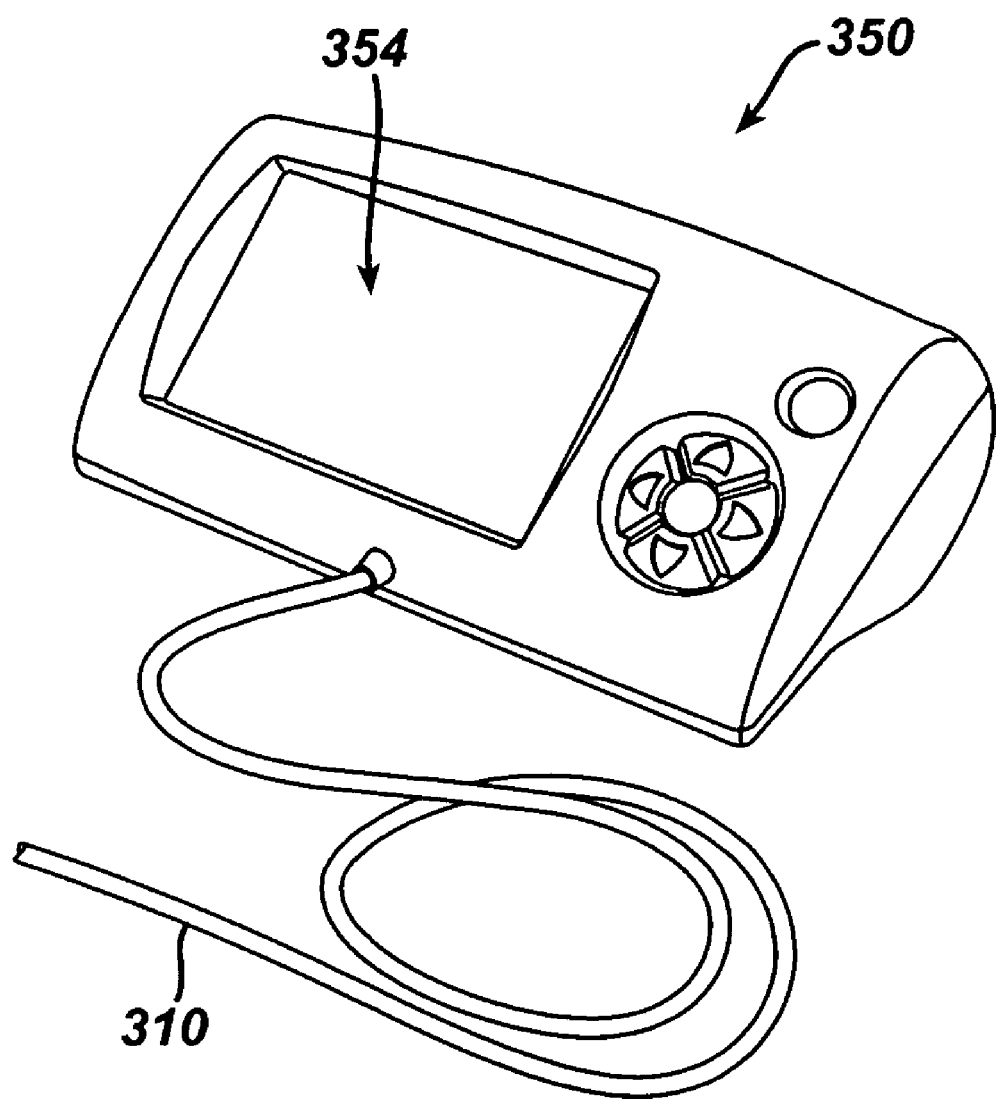
FIG. 27 is a perspective view of an exemplary display device suitable for coupling with the sense head of FIG. 22.
Figure 28:
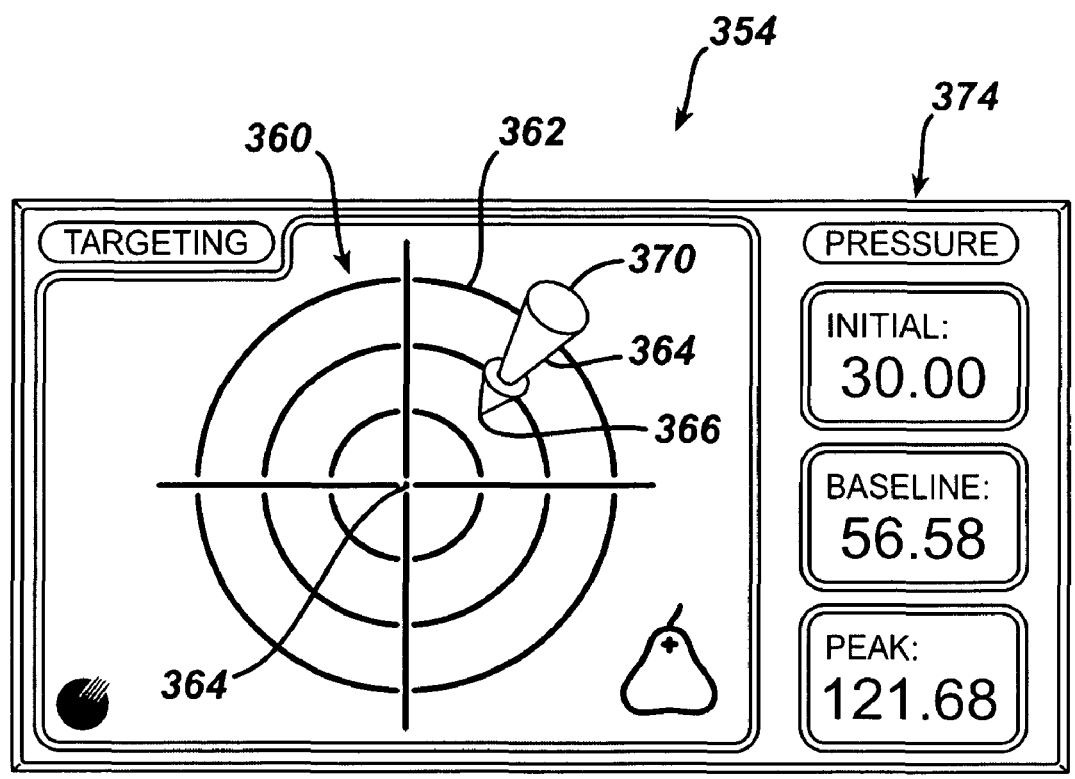
FIG. 28 is an exemplary graphical display suitable for the display device of FIG. 27.
Figure 29:
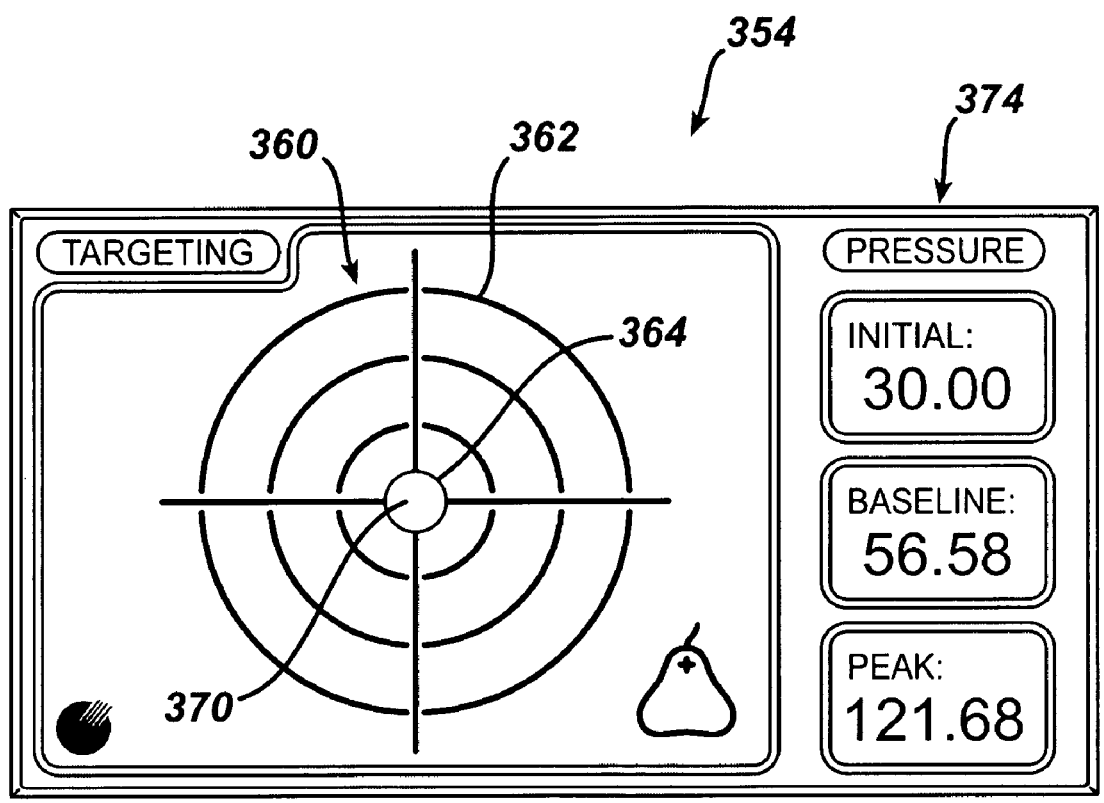
FIG. 29 is the graphical display of FIG. 28 indicating suitable positioning of the sense head of FIG. 22.

FIG. 27 shows an exemplary display device 350 that is configured to translate information communicated from the sense head 300 into visual representations readable by a user. In the present example, display device 350 is in communication with sense head 300 via cable 310, but again, any alternative to cable 310 may be used. Display device 350 further comprises a graphical display 354, which includes a target display 360, and is illustrated in FIGS. 28-29. The target display 360 of the present example includes a crosshairs 362 and an arrow indicator 364. The target display 360 of this example is operable to render location and orientation information relating to the location and orientation of sense head 300 relative to port 42. In particular, the position of the tip 366 of arrow indicator 366 relative to the center 364 of crosshairs 362 may serve to indicate the position of needle window 302 relative to the center of port 42 (e.g., septum 76). In other words, the center 364 of crosshairs 360 may represent the center of septum 76; with the tip 366 of arrow indicator 366 representing needle window 302. The positioning data may be refreshed at any suitable rate, such as in approximate real-time, to provide the user location feedback via targeting display 360. The user may thus move sense head 300 until targeting display 360 indicates that the needle window 302 is located directly over port 42.

Orientation data may be rendered via targeting display 360 in terms of the tilt of arrow indicator 366. In other words, the direction and amount of tilt of arrow indicator 366 may represent the orientation of sense head 300 relative to port 42, such that arrow indicator 366 pivots about its tip 366 to indicate such orientation. As with positioning/location data, the orientation data may be refreshed at any suitable rate, such as in approximate real-time, to provide the user orientation feedback via targeting display 360. To the extent that sense head 300 cannot be satisfactorily oriented relative to port 42 (e.g., if port 42 has flipped upside-down or on its side relative to the fascial plane of patient), surgery may be required to re-orient port 42.

FIG. 29 shows a view of display device 350 with a target display 360 indicating that the sense head 300 is positioned substantially directly over port 42 and substantially parallel with port 42. Accordingly, arrow indicator 366 is positioned over center 364 of crosshairs 362, and pivoted upright (i.e., perpendicular to the screen), such that only the tail 370 of arrow indicator 366 can be seen. Such a display may indicate to the user that a needle 403 inserted straight into needle window 302 will successfully reach septum 76 of port.

It will also be appreciated that further visual indication may be given to a user to represent location and orientation information, such as with the use of colors. For instance, in the targeting display 360 shown in FIG. 28, the arrow indicator 366 may be shown in red to indicate that insertion of needle 403 through needle window 302 would not be appropriate (e.g., needle 403 would not reach septum 76). By contrast, in the targeting display 360 shown in FIG. 23, tail 370 of arrow indicator 366 may be shown in green to indicate that insertion of needle 403 through needle window 302 would be appropriate (e.g., the needle would reach septum 76).

It will also be appreciated that sense head 300 need not be perfectly parallel with port 42 in order to successfully pass needle 403 through needle window 302 into septum 76. Accordingly, display device 350 may provide an indication showing that needle 403 may successfully reach septum 76 through needle window 302, despite a non-parallel orientation of sense head 300 relative to port 42. For instance, such orientation may be indicated where tail 370 of arrow indicator 366 is within a particular ring of crosshairs 362. Alternatively, such orientation may be indicated by coloring arrow indicator 366 yellow or some other color. Still other ways in which the sufficiency of a non-parallel orientation may be indicated in target display 360 will be apparent to those of ordinary skill in the art.

Similarly, there may be a situation in which sense head 300 cannot be located directly over port 42 without having unsatisfactory orientation of sense head 300 relative to port 42; while sense head 300 may be oriented generally parallel with port 42 when not positioned directly over port 42. In some such situations, the septum 76 may nevertheless be reached by needle 403 inserted through needle window 302 if needle 403 is oriented properly with respect to sense head 300 (e.g., at an angle of approximately 80° or a 10° deflection). Accordingly, display device 350 may provide an indication showing that needle 403 may successfully reach septum 76 through needle window 302, despite sense head 300 not being positioned directly over port 42. For instance, such orientation may be indicated where tail 370 of arrow indicator 366 is within a particular ring of crosshairs 362. Alternatively, such orientation may be indicated by coloring arrow indicator 366 yellow or some other color. Still other ways in which the sufficiency of an indirect sense head 300 location may be indicated in target display 360 will be apparent to those of ordinary skill in the art.

It will also be appreciated that sense head 300 may be configured to obtain depth data indicating the distance from needle window 302 to port 42 (and, hence, depth to septum 76). Such depth data may be represented on display device 350 in a variety of ways. For instance, the depth may be indicated as a numerical value and/or in any other suitable way. In addition to location, orientation, and depth-related information, other geometric information that may be obtained by sense head 300 and communicated to display device 350 will be apparent to those of ordinary skill in the art.

In addition to displaying information relating to the location and orientation of sense head 300 relative to port 42, display device 360 may also display pressure data communicated from port 42 to sense head 300. Accordingly, display device 350 of the present example comprises a pressure display portion 374. As shown, pressure display portion 374 provides an initial pressure reading, a baseline pressure, and a peak pressure. The initial pressure reading represents the pressure within implanted portion 32 before fluid is added or withdrawn. The baseline pressure reading represents the current pressure within implanted portion 32 (e.g., as fluid is being added or withdrawn or after fluid has been added or withdrawn). The peak pressure reading represents the peak pressure sensed during peristaltic motion of the stomach. Of course, any other pressure parameters may be displayed, as may other data such as temperature, etc.

As noted above, sense head 300 may be configured to receive pressure data from port 42 in a manner similar to pressure-reading device 60. It will therefore be appreciated that the TET coil of sense head 300 may also serve as a telemetry coil to receive telemetry signals from coil 114 in port 42 indicating pressure or other data. Alternatively an additional coil dedicated to such telemetry may be provided in sense head 300. As yet another variation any of vertical coils 306 and/or horizontal coils 304 may be used for such telemetry. Still other suitable configurations will be apparent to those of ordinary skill in the art.

In view of the foregoing, it will be appreciated that sense head 300 and display device 350 may be used to provide approximately real-time pressure measurements to a user before, during, and after the addition or withdrawal of fluid to or from implanted portion 32. For instance, a surgeon may adjust the saline content of implanted portion 32 while patient 34 swallows a fixed amount of water, and may monitor the pressure level in implanted portion via sense head 300 and display device 350 during such activities. It will be appreciated that an optimal pressure adjustment may be determined based on a variety of factors related to pressure data, including but not limited to any of the following: the original baseline pressure; the new baseline pressure; the maximum peristaltic pressure; the minimum peristaltic pressure; the length of a peristaltic contraction; the Fourier transform of a peristaltic contraction data spike; the pressure decay time constant during persistaltic contractions; the total averaged pressure decay time constant during a water swallowing period; the number of peristaltic contractions to swallow a fixed amount of water; one or more forces exerted by an implanted device and/or an anatomical structure; energy of an implanted device or of fluid therein; the fill rate of fluid into an implanted device; the volume of fluid in an implanted device; the capacity of an implanted device; the flow rate of fluid into or within an implanted device; the pressure pulse rate of fluid within an implanted device; a counted number of pressure pulses of fluid within an implanted device; one or more electrical signals communicated from tissue prior to and/or in response to adjustment of an implanted device; chemical(s) output from tissue prior to and/or in response to adjustment of an implanted device; other tissue feedback responsive to adjustment of an implanted device; or any other factors.

In one embodiment, display device 350 is operable to receive data indicative of the above-noted factors in any suitable fashion (e.g., from sensors, etc.), and is further operable to automatically process such factors and present the result of such processing to the user. For instance, display device 350 may be configured to determine an ideal amount of fluid to be added or withdrawn based on such processing of factors, and may simply display a message to the user such as "Add 4 cc's of fluid," "Withdraw 0.5 cc's of fluid," or the like. Such messages may be displayed in addition to or in lieu of displaying pressure measurements, changes in pressure, or other data. Other suitable processes of any of the above-noted factors or other factors, as well as ways in which results of such processes may be presented to the user, will be apparent to those of ordinary skill in the art.

In the present example, pressure sensor 84 provides pressure data at an update rate of approximately 20 Hz. Such a rate may provide a telemetry/TET mode cycle completion at approximately every 50 ms. For instance, coil 114 may provide TET for port 42 for approximately 45 ms to power port 42, then provide telemetry of pressure data for approximately 5 ms. Of course, any other switching topology may be used. It will also be appreciated that switching between TET and telemetry may be unnecessary. For instance, port 42 may be active, such that TET is not required. As another example, a second coil (not shown) may be added to port 42, with one of the coils in port 42 being dedicated to TET and the other to telemetry. Still other alternatives and variations will be apparent to those of ordinary skill in the art.

While display device 350 of the present example shows pressure data being represented numerically, it will be appreciated that pressure data may be represented in a variety of other ways. For instance, a graph may show pressure as a function of time, which may be useful for monitoring pressure during peristaltic activity or for other purposes. It will also be appreciated that absolute values of pressure at particular moments in time need not be displayed, and that display device 350 may instead display changes in pressure value. Other ways in which pressure data or other data may be displayed will be apparent to those of ordinary skill in the art.

As discussed above, it may be desirable to account for temperature, atmospheric pressure, and other factors when considering measurements of pressure within implanted portion 32. Accordingly, sense head 300 may receive additional data such as temperature measurements taken within implanted portion 32, and display device 350 may comprise logic configured to adjust pressure readings in accordance with a variety of such factors.

In one version, sense head 300 comprises a switch (not shown) which is operable to switch sense head 300 between a positioning mode and a pressure sensing mode. Thus, the user may switch sense head 300 to positioning mode to obtain location and orientation data to sufficiently position sense head 300 over port 42. The user may then switch sense head 300 to pressure sensing mode to obtain pressure measurements before, during, and after the addition or withdrawal of fluid to or from implanted portion 32. Alternatively, a similar switch may be provided on display device 350. In yet another version, no switch is used, such that sense head 300 is operable for use in a positioning mode and pressure sensing mode simultaneously. Still other possible modes and features for effecting switching between such modes will be apparent to those of ordinary skill in the art.

It will also be appreciated that sense head 300 may be used in conjunction with a port that has a coil but lacks a pressure sensor. In other words, sense head 300 may be used simply to determine the location and orientation of a port. Upon such a determination, pressure data may be obtained from a source other than the port (e.g., from a sensor elsewhere in implanted portion, from a sensor external to the patient, etc.) or not obtained at all. In addition, while examples discussed above include use of sense head 300 with port 42, it will be appreciated that sense head 300 may be used with port 1142. Of course, such use may necessitate the inclusion of a TET/telemetry coil in sense head 1142, or some other device(s) operable to transmit signals for reception by coils 304, 306. Other variations of sense head 300 and variations of using sense head 300 will be apparent to those of ordinary skill in the art.

Figure 30:
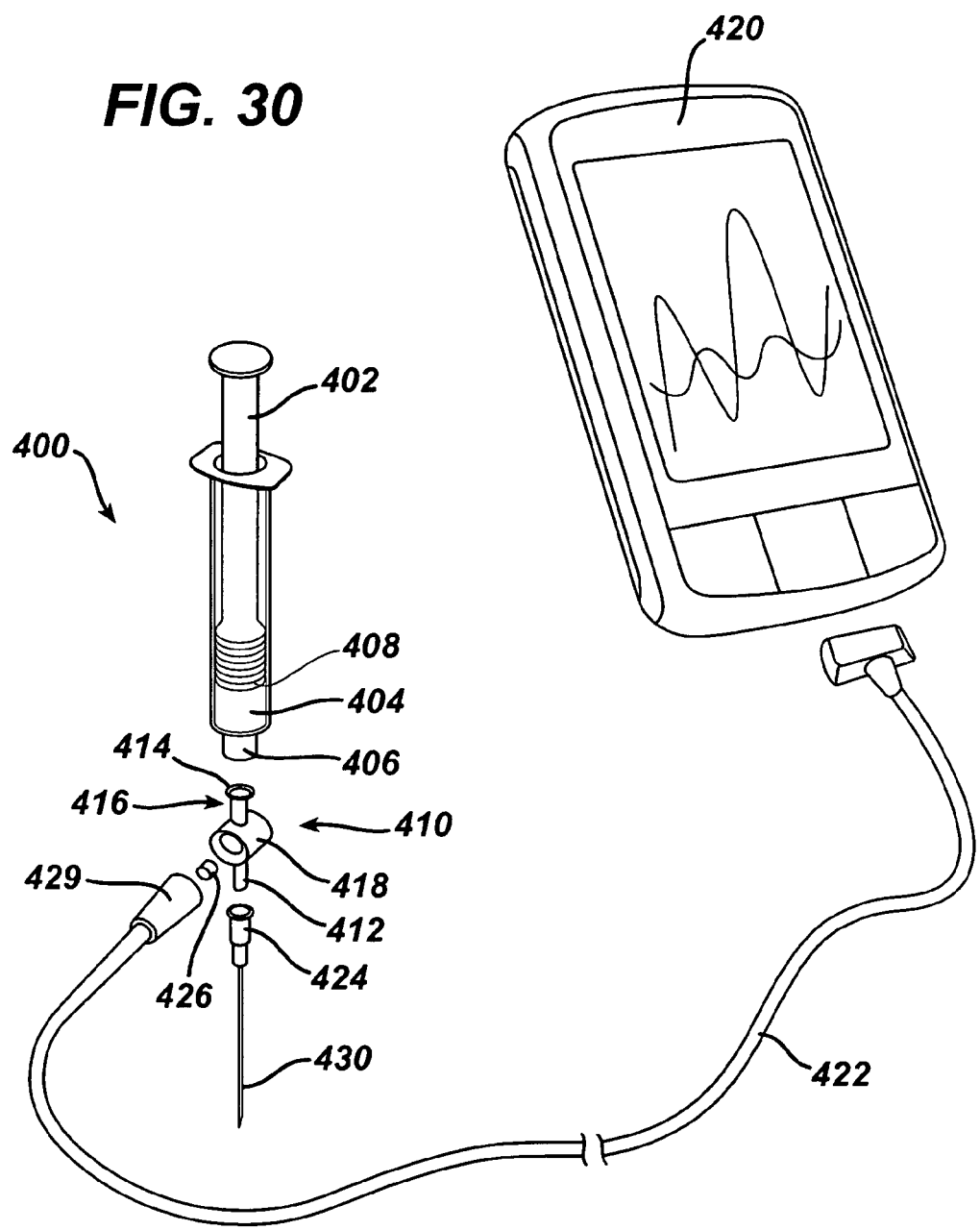
FIG. 30 is a perspective exploded view of an exemplary syringe system with pressure sensor and display device.
Figure 31:
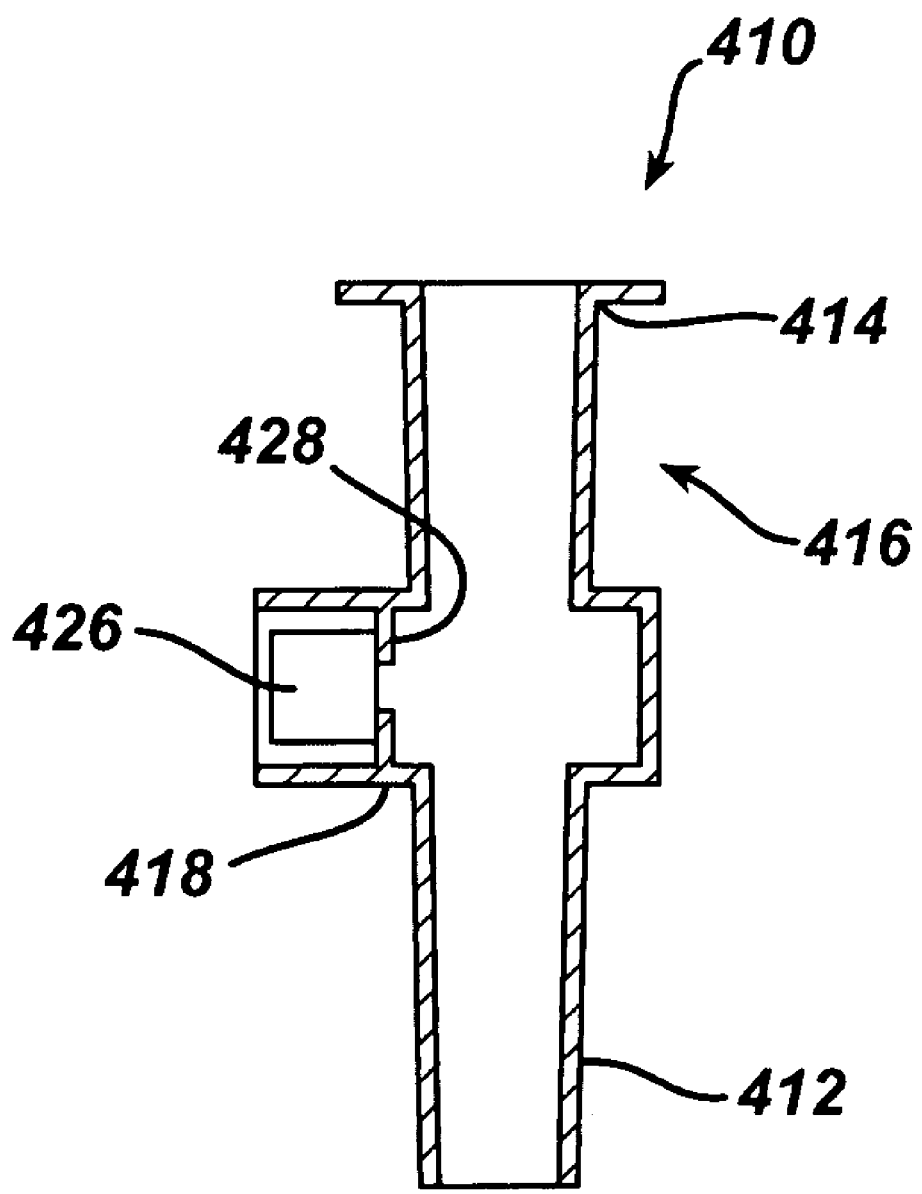
FIG. 31 is a cross-sectional view of a pressure sensing portion of the syringe system of FIG. 32.

Another embodiment is shown in FIGS. 30-31, which depicts an exemplary syringe 400 and a display device 420 in communication via a cable 422. Syringe 400 comprises a plunger 402, a barrel 404, a pressure sensing component 410, and a needle 430. In the present example, plunger 402, barrel 404, and needle 430 are conventional components. Accordingly, barrel 404 has a male luer lock portion 406; and needle 430 has a female luer lock portion 424. Plunger 402 has a piston 408 configured to sealingly engage with barrel 404. In one version, needle 430 comprises a Huber needle. Of course, any of these components, among others, may be varied.

Cable 422 has a boot portion 429, which is configured to selectively attach to pressure sensing component 410. Boot portion 429 further comprises a feature (not shown) that is operable to electrically engage with pressure sensor 426, and thereby communicate pressure readings obtained by pressure sensor 426 along cable 422. Such a feature may comprise one or more terminals (not shown) or any other feature(s). In another embodiment, pressure sensing component 410 is fixedly secured to boot portion 429 and cable 422. Other suitable configurations will be apparent to those of ordinary skill in the art.

In the present example, pressure sensing component 410 comprises a male luer lock portion 412, a female luer lock portion 414, a vertical cylindraceous portion 416, a horizontal cylindraceous portion 418, and a pressure sensor 426. Male luer lock portion 412 of pressure sensing component 410 is configured to engage with female luer lock portion 424 of needle 430; while female luer lock portion 414 of pressure sensing component 410 is configured to engage with male luer lock portion 406 of barrel 404. Accordingly, it will be appreciated that pressure sensing component 410 may be retrofitted to a variety of existing syringes. Alternatively, a syringe 400 may be constructed having a pressure sensing component 410 or similar feature integrally formed within.

As shown, pressure sensor 426 is positioned within horizontal cylindraceous portion 418, adjacent to an annular flange 428. In one example, pressure sensor 426 is sealingly secured to annular flange 428. In this example, boot portion 429 comprises one or more electrodes (not shown) or similar features configured to communicate with and/or receive communications from pressure sensor 426 upon engagement of boot portion 429 with pressure sensing component 410. In another example, pressure sensor 426 is fixed within boot portion 429, and may be positioned adjacent to annular flange 428 upon engagement of boot portion 429 with pressure sensing portion 410. Alternatively, any other suitable configuration may be used.

Pressure sensor 426 may be constructed in accordance with any of the pressure sensors described above. Alternatively, pressure sensor 426 may comprise any off-the-shelf pressure sensor suitable for use, or any other type of pressure sensor. In the present example, when syringe 400 is assembled, vertical cylindraceous portion 416 provides a sealed conduit for fluid communication from barrel 404 to needle 430. Vertical cylindraceous portion 416 is further in fluid communication with horizontal cylindraceous portion 418; as is pressure sensor 426. Accordingly, it will be appreciated that pressure sensor 426 may be operable to sense pressure of fluid within syringe 400. It will also be appreciated that pressure sensed by pressure sensor 426 may be communicated to display device 420 via cable 422, and displayed thereon in any suitable format.

In one exemplary use, needle 430 is inserted into patient 34 to reach a septum of an injection port (not shown). Any suitable port may be used, including but not limited to any of the ports 42, 1142 described above and variations thereof, and any port lacking a pressure sensor. Upon such insertion in the present example, needle 430 may be placed in fluid communication with implanted portion 32, such that the pressure of the fluid in implanted portion 32 and the fluid in syringe 400 may be substantially equalized. It will therefore be appreciated that pressure sensed by pressure sensor 426 may be indicative of the pressure of fluid within implanted portion 32. Such pressure information may be particularly useful during a process of adjusting pressure within implanted portion 32 via addition of fluid to implanted portion 32 with syringe or withdrawal of fluid from implanted portion 32 with syringe 400. In particular, syringe 400 may permit simultaneous adjustment and reading of fluid pressure.

For instance, a user may first insert needle 430 into patient 34 to reach the septum 76 of an injection port 42, 1142. Upon pressure equalization, the user may then read the initial pressure via display device 420. It will be appreciated that pressure equalization may be determined by a pressure reading remaining substantially constant. The user may then add or withdraw fluid to or from implanted portion 32 using syringe 400, watching for changes in pressure indicated via display device 420. Because no valve or other mechanism is necessarily required to switch syringe 400 between a pressure sensing mode and an add/withdrawal mode, such pressure readings may be obtained as the user is adding or withdrawing fluid to or from implanted portion 32. Accordingly, pressure sensing component 410 and pressure sensor 426 may be considered substantially in-line with the other syringe 400 components. As used herein, the phrase "substantially in-line" shall be read to imply that fluid may be added or withdrawn with syringe 400 substantially contemporaneously with pressure sensing by pressure sensor 426; and that manipulation of a valve or other mechanism is not required to switch between an add/withdrawal mode of syringe 400 and a pressure sensing mode of syringe 400. However, the phrase "substantially in-line" shall not be read to require that a straight line must be able to intersect pressure sensor 426 and all other components of syringe 400.

Pressure readings may thus be obtained in approximately real-time, as the pressure is adjusted by the user with syringe 400. To the extent that there is a delay between the user's manipulation of syringe 400 and the time the pressure equalizes among syringe 400 and implanted portion 32, the user may simply wait until the pressure reading indicated by display device 420 becomes substantially constant. Other suitable uses for syringe 400 and display device 420 will be apparent to those of ordinary skill in the art.

Figure 32:
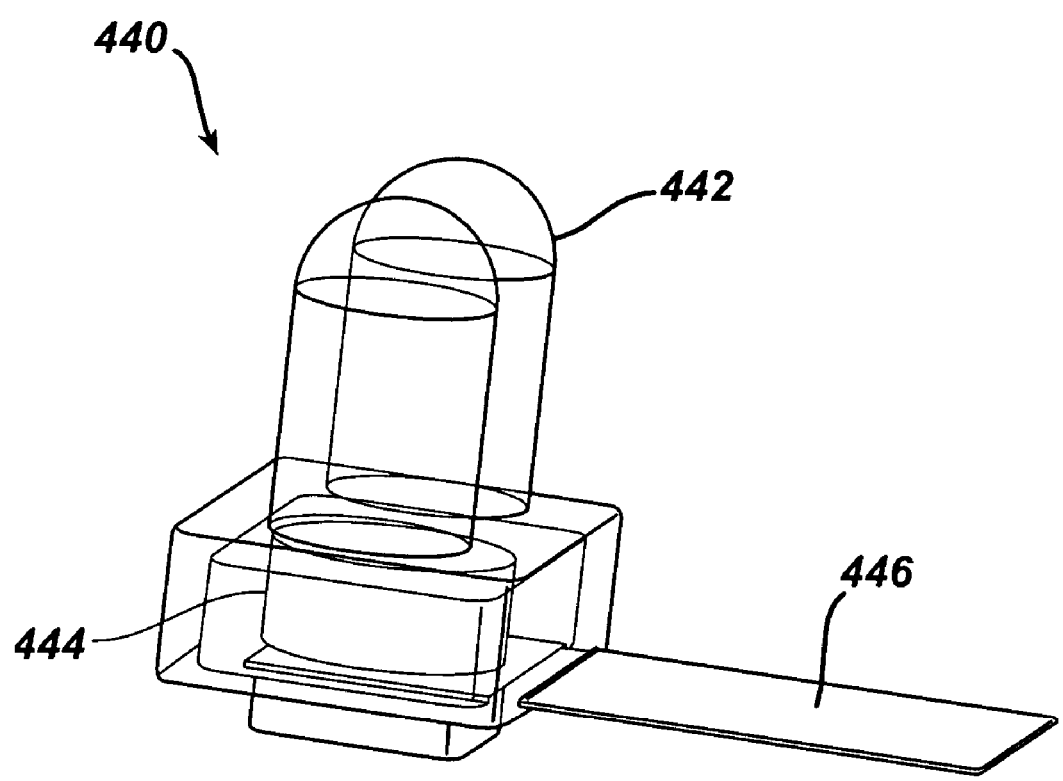
FIG. 32 is a perspective view of an exemplary infrared communicator suitable for use with the syringe system of FIG. 30.

FIG. 32 depicts an exemplary substitute for cable 422. In this variation, cable 422 of the syringe 400 version shown in FIGS. 30-31 is substituted with a wireless infrared communicator 440. Infrared communicator 440 comprises a pair of LED's 442, a battery 444, and a pull-tab 446. Infrared communicator 440 is securable to pressure sensing component 410, and is in communication with pressure sensor 426. In one embodiment, pressure sensor 426 is housed within infrared communicator 440, and is configured to be exposed to the pressure of fluid within pressure sensing component 410 when coupled with pressure sensing component 410. For instance, such pressure exposure may be provided by having pressure sensor 426 in direct contact with fluid in pressure sensing component 410. Alternatively, infrared communicator 440 and/or pressure sensing component 410 may comprise a diaphragm or other member operable to communicate pressure forces to pressure sensor 426 positioned between pressure sensor 426 and fluid in pressure sensing component 410. In yet another embodiment, pressure sensor 426 is a component of pressure sensing component 410, and infrared communicator 440 is configured to receive pressure data obtained from pressure sensor 426 when coupled with pressure sensing component 410. Still other suitable configurations will be apparent to those of ordinary skill in the art.

Infrared communicator 440 of the present example is operable to communicate pressure data obtained from pressure sensor 426 via LED's 442 in infrared light. Accordingly, it will be appreciated that display device 420 may be modified to include an infrared sensor (not shown) operable to receive such communications. Battery 444 may be used to provide power to infrared communicator 440. Pull-tab 446 may be initially positioned between battery 444 and a terminal to preserve the life of battery 444 before a first use. The user may thus remove pull-tab 446 before the first use. Alternatively, infrared communicator 440 may comprise a switch or other mechanism for selectively activating battery 444. Other variations will be apparent to those of ordinary skill in the art. It will also be appreciated that this variation of syringe 400 may be used in a manner similar to any of the other variations of syringe 400, as described above.

Figure 33:
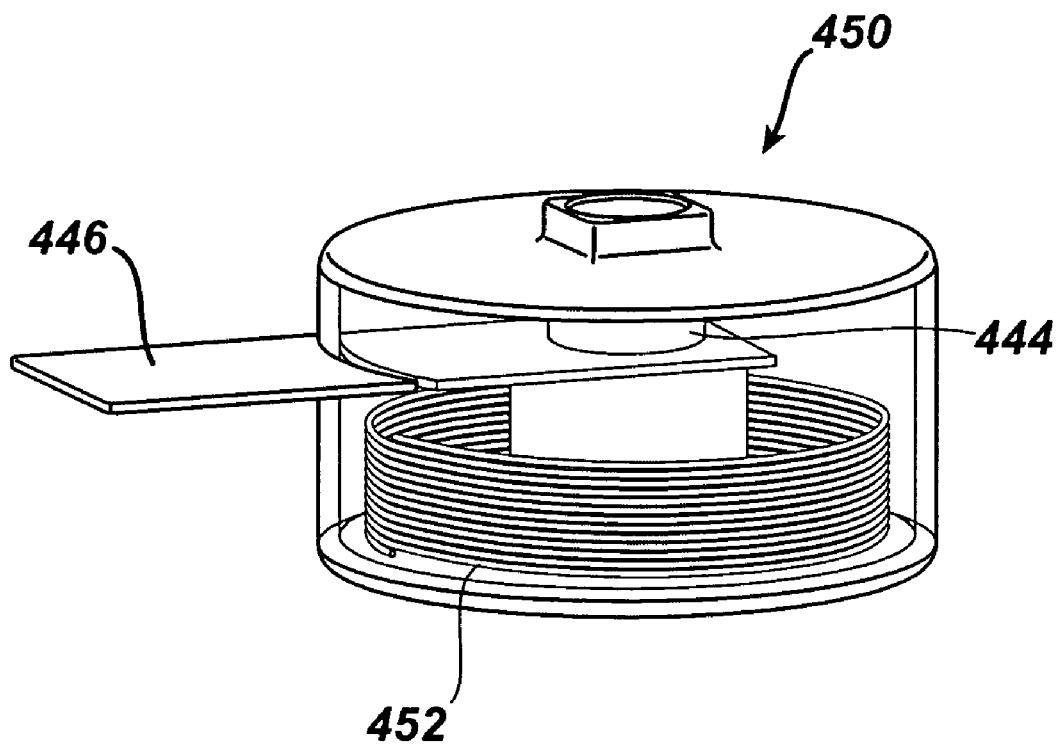
FIG. 33 is a perspective view of an exemplary RF communicator suitable for use with the syringe system of FIG. 30.

FIG. 33 shows yet another exemplary substitute for cable 422. In this variation, cable 422 of the syringe 400 version shown in FIGS. 30-31 is substituted with a wireless radio frequency (RF) communicator 450. RF communicator 450 comprises an RF coil 452, a battery 444, and a pull-tab 446. RF communicator 450 is securable to pressure sensing component 410, and is in communication with pressure sensor 426. As noted above with respect to infrared communicator 440, pressure sensor 426 may reside within RF communicator 450 or within pressure sensing component 410. other suitable configurations will be apparent to those of ordinary skill in the art. RF communicator 450 of the present example is operable to communicate pressure data obtained from pressure sensor 426 via RF coil 452 as an RF signal. Accordingly, it will be appreciated that display device 420 may be modified to include an RF signal receiver (not shown) operable to receive such communications. Battery 444 may be used to provide power to RF communicator 450. Pull-tab 446 may be initially positioned between battery 444 and a terminal to preserve the life of battery 444 before a first use. The user may thus remove pull-tab 446 before the first use. Alternatively, RF communicator 450 may comprise a switch or other mechanism for selectively activating battery 444. Other variations will be apparent to those of ordinary skill in the art. It will also be appreciated that this variation of syringe 400 may be used in a manner similar to any of the other variations of syringe 400, as described above.

Figure 34:
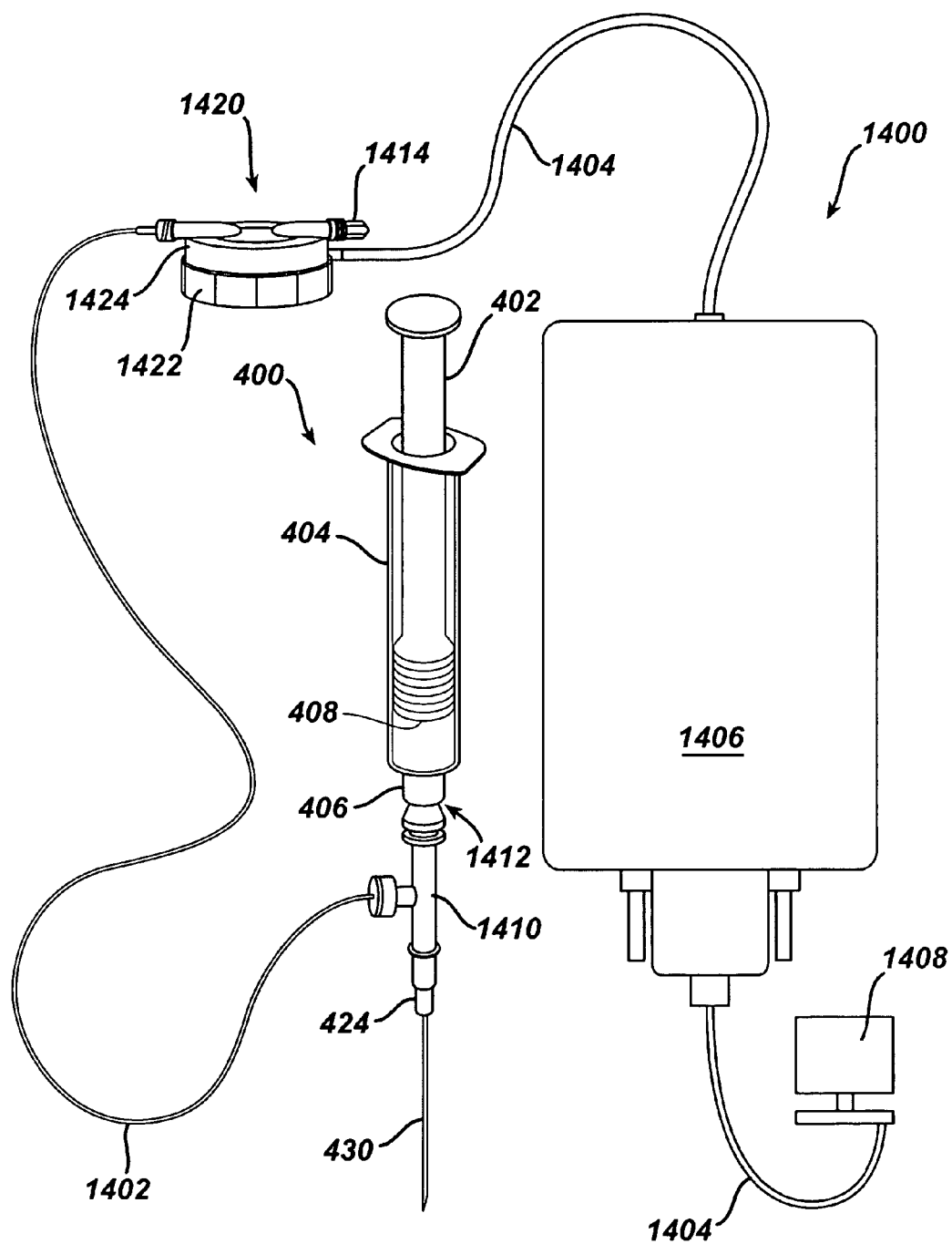
FIG. 34 is a schematic view of an alternative exemplary pressure sensing syringe system.

FIG. 34 shows another exemplary pressure sensing syringe system 1400. In this example, syringe system 1400 comprises a syringe 400, tubing 1402, a pressure sensing portion 1420, cables 1404, an interface component 1406, and a display device 1408. Syringe 400 comprises "T"-joint 1410 having a two-way leur activated valve 1412. "T"-joint 1410 is in fluid communication with needle 430 and tubing 1402. Two-way luer activated valve 1412 is configured such that it opens when "T"-joint 1410 is coupled with male luer lock portion 406 of syringe 400. Of course, a "T"-joint 1410 or other device may be provided without a two-way luer activated valve 1412. It will also be appreciated that pressure sensing component 410 described above may also have a two-way luer activated valve (e.g., at female luer lock portion 414). In the present example, when "T"-joint 1410 is coupled with syringe 400, tubing 1402 is operable to communicate the pressure of fluid within syringe 400 to pressure sensing portion 1420. It will be appreciated that "T"-joint may be secured to a variety of existing syringes 400 and needles 430. To the extent that a two-way luer activated valve 1412 or similar device is used (e.g., in "T"-joint 1410, in pressure sensing component 410, etc.), barrel 404 may be removed after pressure is adjusted without affecting fluid pressure in components "downstream" of two-way luer activated valve 1412. By way of example only, it may be desirable to adjust pressure using syringe 400, then remove barrel 404 from two-way luer activated valve 1412, then have patient 34 stand upright, then obtain subsequent pressure measurements. Removal of barrel 404 and/or other uses for two-way luer activated valve 1412 may also be desirable in a number of other situations.

Figure 35:
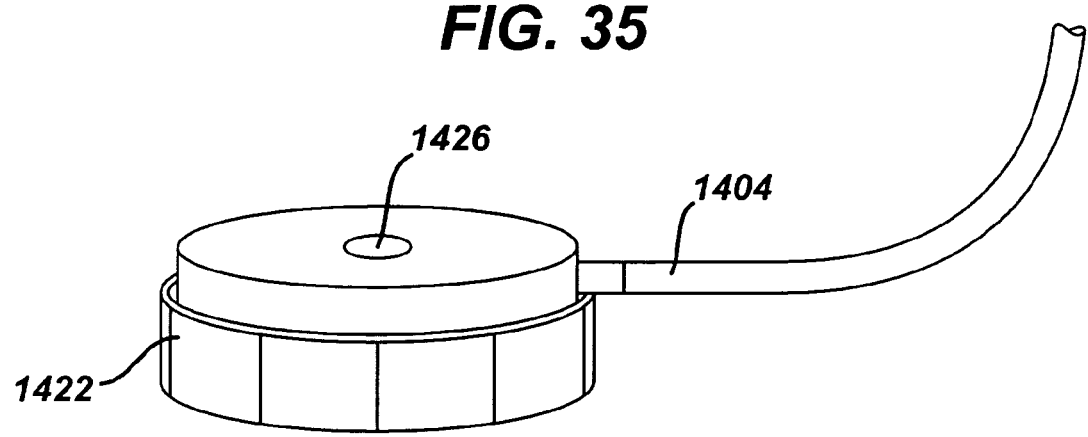
FIG. 35 is a perspective view of a reusable sensor portion of the pressure sensing syringe system of FIG. 34.
Figure 36:
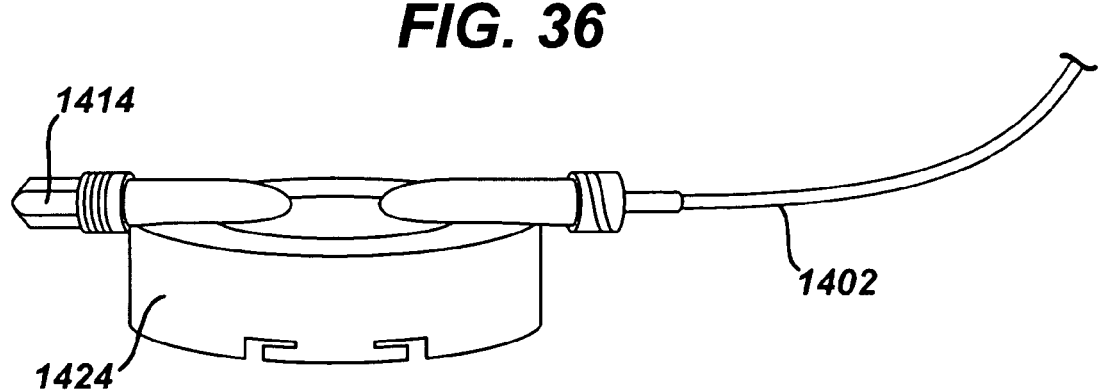
FIG. 36 is a partial perspective view of a disposable cap portion of the pressure sensing syringe system of FIG. 34.

As shown in FIGS. 34-36, pressure sensing portion 1420 comprises a reusable sensor portion 1422 and a disposable cap portion 1424. Reusable sensor portion 1422 and disposable cap portion 1424 are configured to selectively engage one another. When coupled with reusable sensor portion 1422, disposable cap portion 1424 is in fluid communication with reusable sensor portion 1422, such that pressure of fluid within tubing 1402 may be communicated to reusable sensor portion 1422 via disposable cap portion 1424. In one embodiment, disposable cap portion 1424 comprises the pressure dome described in U.S. Pat. No. 6,725,726, the disclosure of which is incorporated by reference herein. Reusable sensor portion 1422 comprises a pressure port 1426, which is configured to receive such fluid pressure communications from disposable cap portion 1424. For instance, pressure port 1426 may comprise a diaphragm or other structure suited for receiving fluid pressure communications. Reusable sensor portion 1422 further comprises a pressure sensor (not shown), such as a transducer, which is configured to provide pressure data via cable 1404 to interface component 1406. Interface component 1406 is operable to process such pressure data and communicate it to display device 1408 via cable 1404. In one embodiment, reusable sensor portion 1422 comprises a Model SP840 or SP844 sensor from MEMSCAP of Durham, N.C. though any other sensor portion 1422 component(s) may be used. Of course, interface component 1406 and display device 1408 may alternatively be integrated as a single device. Interface component 1406 and/or display device 1408 may comprise a desktop PC, a laptop computer, a personal digital assistant (PDA), a dedicated device, or any other suitable device(s).

It will be appreciated that, in order to effectively communicate the pressure of fluid in syringe 400 to reusable sensor portion 1422, it may be desirable to provide a fluid within tubing 1402. Such fluid may be provided within tubing 1402 before attempting to take pressure measurements. While the fluid within tubing 1402 may be the same type of fluid within syringe 400 (e.g. saline), any fluid may be used, including but not limited to gels, silicone fluid, saline, etc. In one embodiment, 1402 tubing is provided pre-primed, such that fluid is provided within tubing 1402 prior to use (e.g., before "T"-joint 1410 is coupled with syringe 400). In another embodiment, tubing 1402 is initially empty of fluid, and the user primes tubing 1402 with fluid before using syringe 400 to add or withdraw fluid to or from injection port 42, 1142. Accordingly, a vent cap 1414 is provided in disposable cap portion 1424 to facilitate priming of tubing 1402 with fluid by facilitating the evacuation of air from tubing 1402.

As described above, a user may use syringe 400 to add fluid to or withdraw fluid from port 42, 1142 to adjust a gastric band 38. With pressure sensing syringe system 1400 assembled as shown in FIG. 34 during such use, or when any suitable variation of pressure sensing syringe system 1400 is used, it will be appreciated that fluid pressure may be sensed, and pressure measurements may be made, as gastric band 38 pressure is adjusted. In other words, pressure may be sensed and adjusted substantially simultaneously, without the need to manipulate a stopcock valve or similar device in order to switch between solely adjusting pressure or solely sensing pressure. Alternatively, such a stopcock valve or similar device may be provided.

While reusable sensor portion 1422 and disposable cap portion 1424 are shown as being separate components, it is contemplated that these components 1422, 1424 may alternatively be unitary. Still other variations will be apparent to those of ordinary skill in the art.

Figure 37:
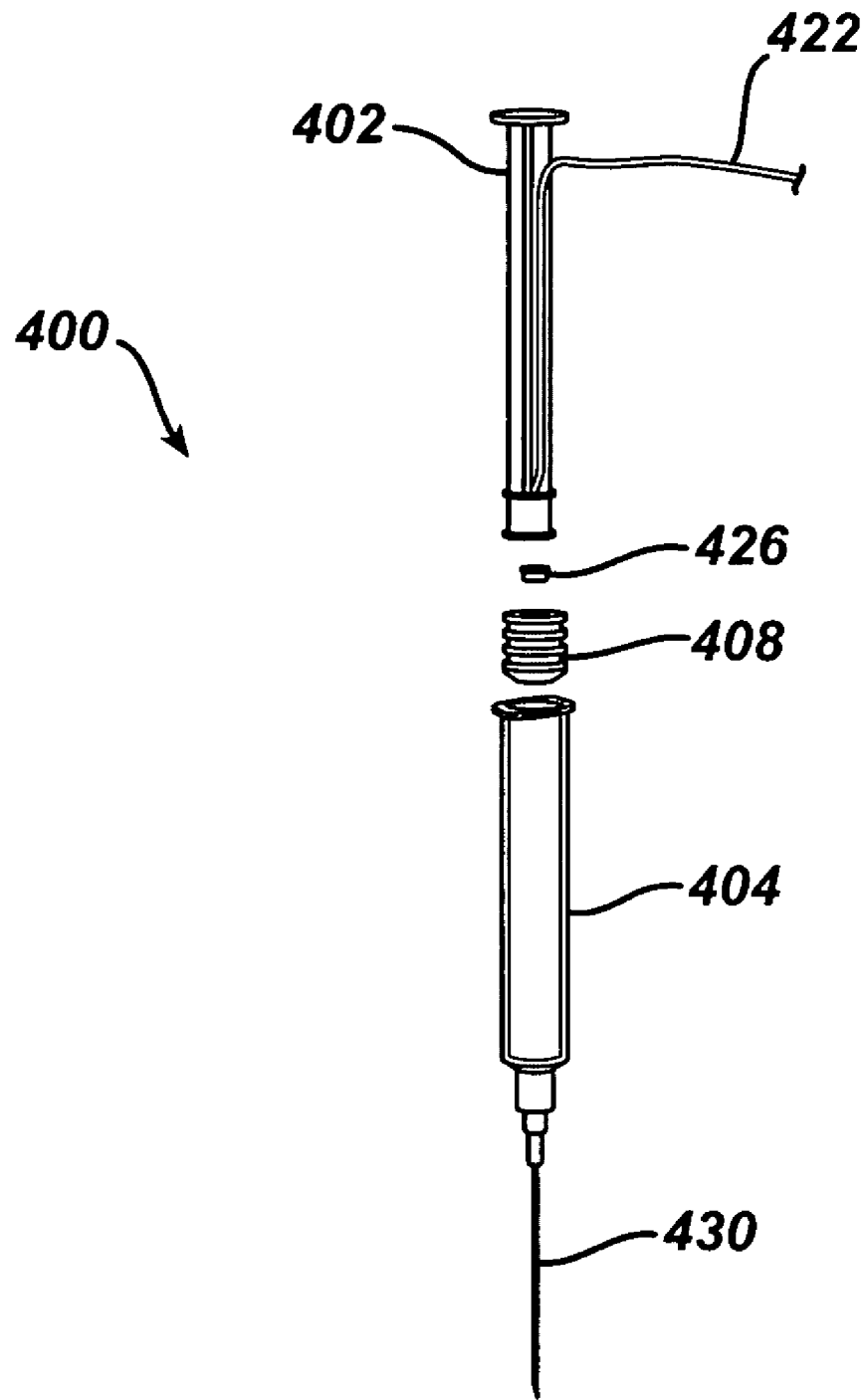
FIG. 37 is a perspective exploded view of an alternative syringe with pressure sensor.

FIG. 37 depicts a variation of syringe 400. In this variation, pressure sensor 426 is positioned between plunger 402 and piston 408, and is in communication with display device 420 via cable 422. Alternatively, pressure sensor 426 may be positioned within piston 408 or at the distal end of piston 408, such that it is in contact with fluid within barrel 404. In any of these variations, pressure sensor 426 may be configured to sense the pressure of fluid within barrel 404, and hence, the pressure of fluid within implanted portion 32 when needle 430 is placed in fluid communication with implanted portion 32. As with embodiments described above, such pressure measurements may be communicated to the user via display device 420 as the user is adding fluid to or withdrawing fluid from the implanted portion 32 via syringe 400 in approximately real-time.

The foregoing describes but a few examples of suitable locations for a pressure sensor external to a patient 34. Several other suitable locations exist, including but not limited to in barrel 404 (e.g., adjacent to male luer lock portion 406), in needle 430 (e.g., adjacent to female luer lock portion 424), or in any other suitable location. Similarly, just as syringe 400 may be varied, so may display device 420. For instance, while display device 420 of the present example is dedicated for use with pressure sensor 426, display device 420 may be any other device. By way of example only, display device 350 shown in FIG. 27 may be configured to receive communications from pressure sensor 426. Alternatively, pressure sensor 426 may be configured to communicate with a desktop PC, laptop computer, personal digital assistant (PDA), or any other device. Other variations of syringe 400 and display device 420 will be apparent to those of ordinary skill in the art, as will methods of processing pressure data. By way of example only, display device 420 or any other device may be configured to analyze pressure amplitude, the rate of change in pressure, and/or other factors to determine whether a user is using a syringe 400 that is too large, too small, or is using the syringe 400 improperly (e.g., injecting fluid too quickly, etc.), and may alert the user (e.g., visually and/or aurally) when such conditions are found.

While embodiments of sense head 300 (described above with reference to FIGS. 22-26) are operable to receive pressure-related communications from a port 42, 1142 having a pressure sensor 84, 1190 those of ordinary skill in the art will appreciate that sense head 300, or variations thereof, may also be used with any of the syringe 400 variations (described above with reference to FIGS. 30-37). For instance, sense head 300 may be used to determine the location and orientation of port 42, 1142 within patient 34, and after appropriate positioning of sense head 300 based on such location and orientation determinations, needle 430 of any of the syringes 400 described herein may be inserted through needle window 302. Pressure data may be obtained from pressure sensor 84 in port 42, 1142 and/or a pressure sensor 426 external to patient 34. Other suitable combinations of components described herein will be apparent to those of ordinary skill in the art.

Figure 38:
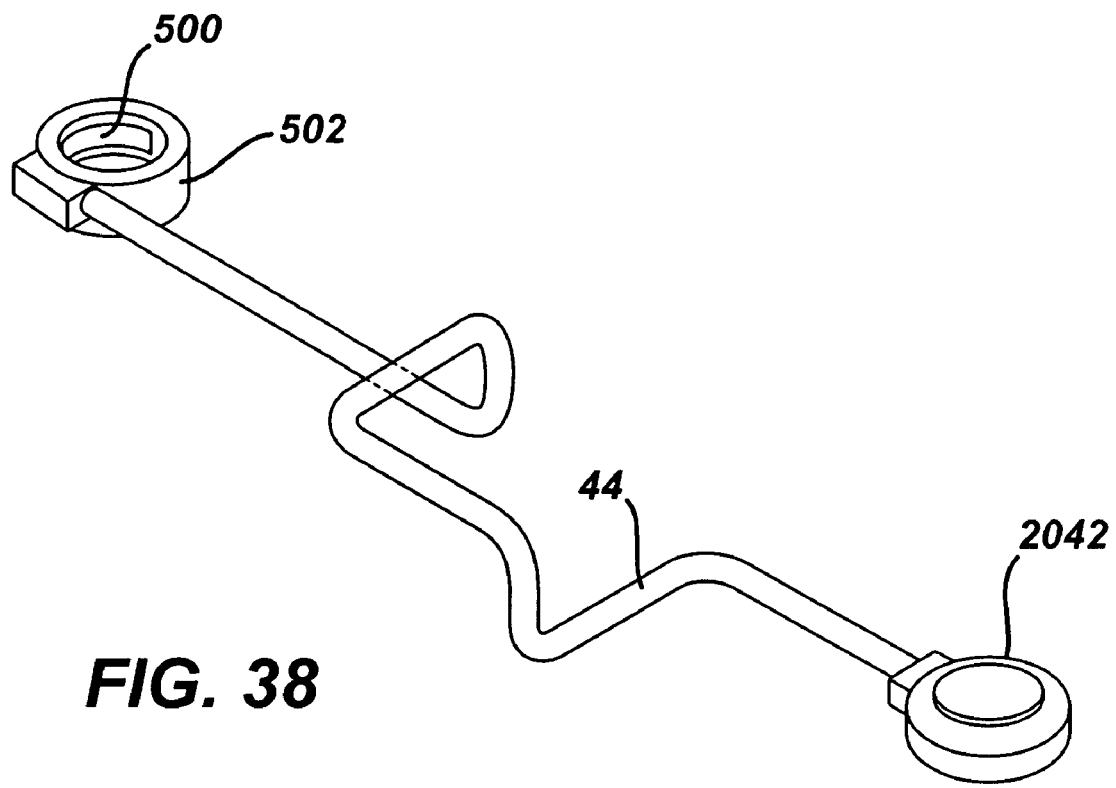
FIG. 38 a perspective view of a gastric band system with a pressure sensor positioned at the gastric band.

While embodiments described above include the use of a pressure sensor within a port 42, 1142, within a syringe 400, or in other locations external to a patient 34, it will be appreciated that a pressure sensor may be located elsewhere within a patient 34. For instance, as shown in FIG. 38, a pressure sensor 500 may be located within a gastric band 502. For instance, pressure sensor 500 may be positioned within an inflatable portion of gastric band 502. To the extent that gastric band 502 comprises a resilient portion and a non-resilient portion, pressure sensor 500 may be secured to either or neither of the resilient portion or non-resilient portion. In any case, pressure sensor 500 may sense and communicate fluid pressure within gastric band 502 before, during, and after fluid is added to or withdrawn from gastric band 502 via injection port 2042 and catheter 44. It will also be appreciated that pressure sensor 500 may be used when a pump (not shown) or any other device is used to adjust pressure within gastric band 502.

Figure 39:
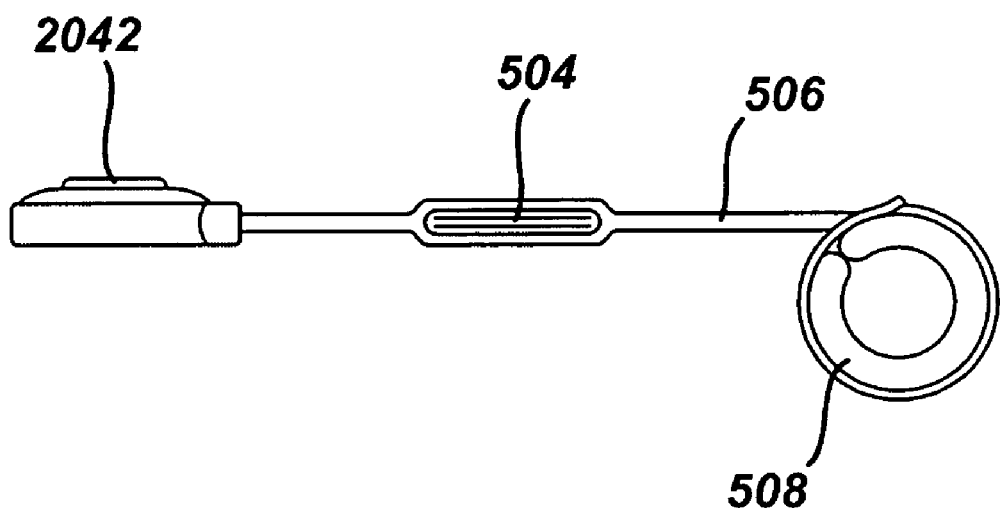
FIG. 39 is a schematic view of a gastric band system with a pressure sensor positioned within the catheter.
Figure 40:
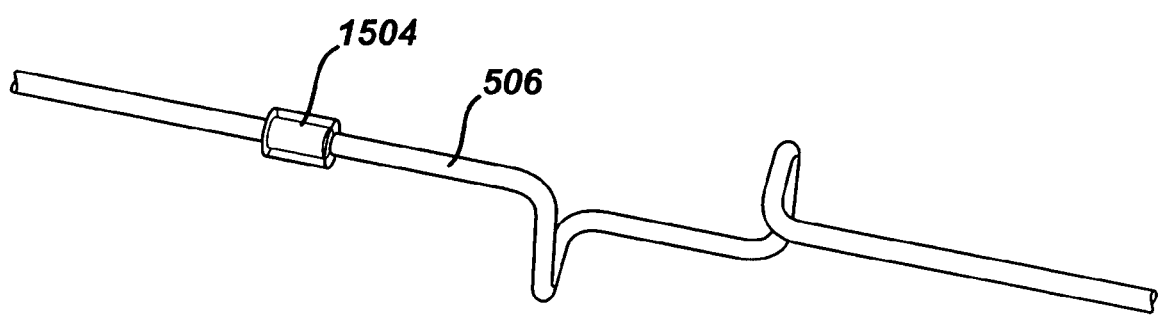
FIG. 40 a perspective view of a gastric band system with an alternative pressure sensor positioned along the catheter.
Figure 41:
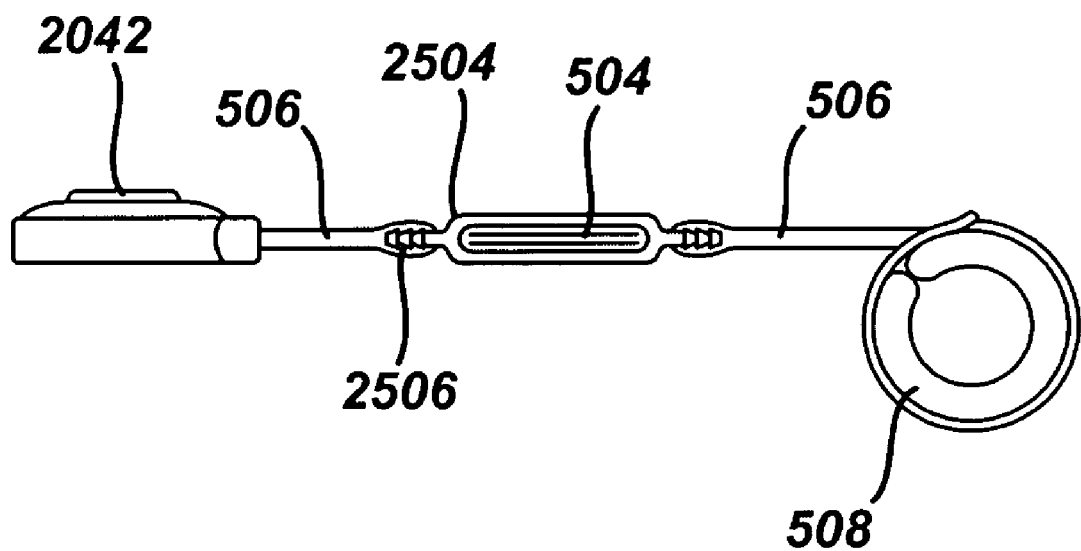
FIG. 41 is a schematic view of a gastric band system with a removable pressure sensor positioned along the catheter.

Alternatively, as shown in FIG. 39, a pressure sensor 504 may be located within a catheter 506 that is positioned between a gastric band 508 and a port 2042, pump, reservoir, or other device in fluid communication with catheter 506. As another variation, an example of which is shown in FIG. 40, a pressure sensor 1504 may be fixedly secured in-line with a catheter 506, while not residing within catheter 506. As yet another variation, an example of which is shown in FIG. 41, a sensor housing 2504 may be removably joined to catheter 506. In this example, pressure sensor 504 resides within sensor housing 2504, and sensor housing 2504 has a pair of barbed connectors 2506 configured to engage with ends of catheter 506. Sensor housing 2504 is thus configured to provide a fluid conduit between port 2042 and gastric band 508, and thus sense the pressure of fluid within sensor housing 2504. It will be appreciated that an already-implanted catheter 506 may be retrofitted with sensor housing 2504, such as by simply severing catheter 506 and inserting barbed connectors 2506 into the severed ends of catheter 506. It will also be appreciated that any alternative to barbed connectors 2506 may be used, including but not limited to clamps, clips, adhesives, welding, etc.

Figure 42:
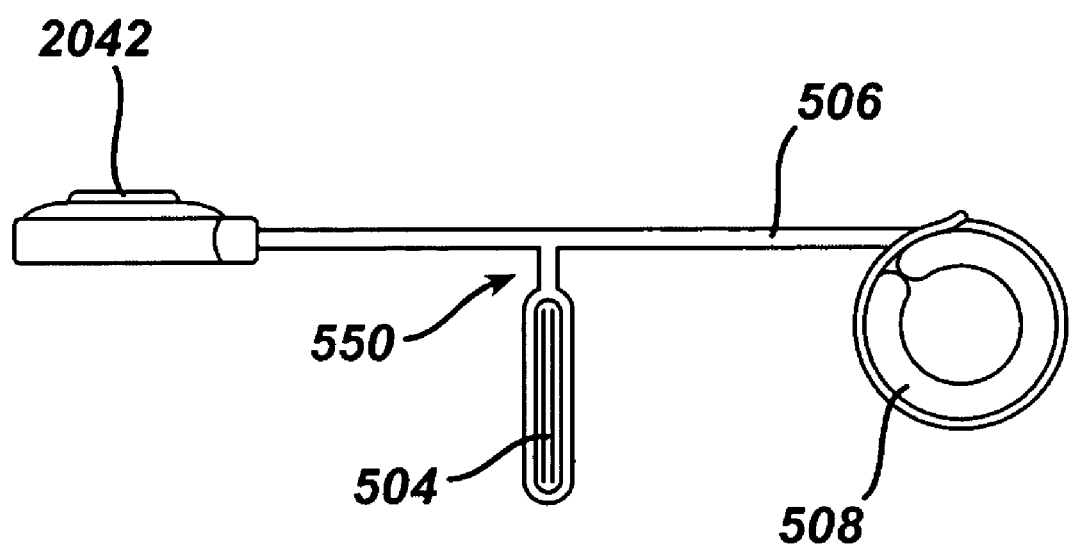
FIG. 42 is a schematic view of a gastric band system with a pressure sensor and alternative catheter configuration.

Yet another variation is shown in FIG. 42, which depicts a catheter 506 having a "T"-shaped intersection 550. A pressure sensor 504 is provided in the arm of "T"-shaped intersection 550 that is perpendicular to catheter 506, and is in fluid communication with catheter 506. In one embodiment, "T"-shaped intersection 550 is integrally formed with catheter 506. In another embodiment, "T"-shaped intersection 550 is a separate component that is joined to catheter 506 (e.g., using structure similar to barbed connectors 2506). Other suitable ways in which "T"-shaped intersection 550 may be provided will be apparent to those of ordinary skill in the art. Similarly, other ways in which a pressure sensor 504, 1504 may be provided within, in-line with, or adjacent to a catheter 506 will be apparent to those of ordinary skill in the art.

Figure 43:
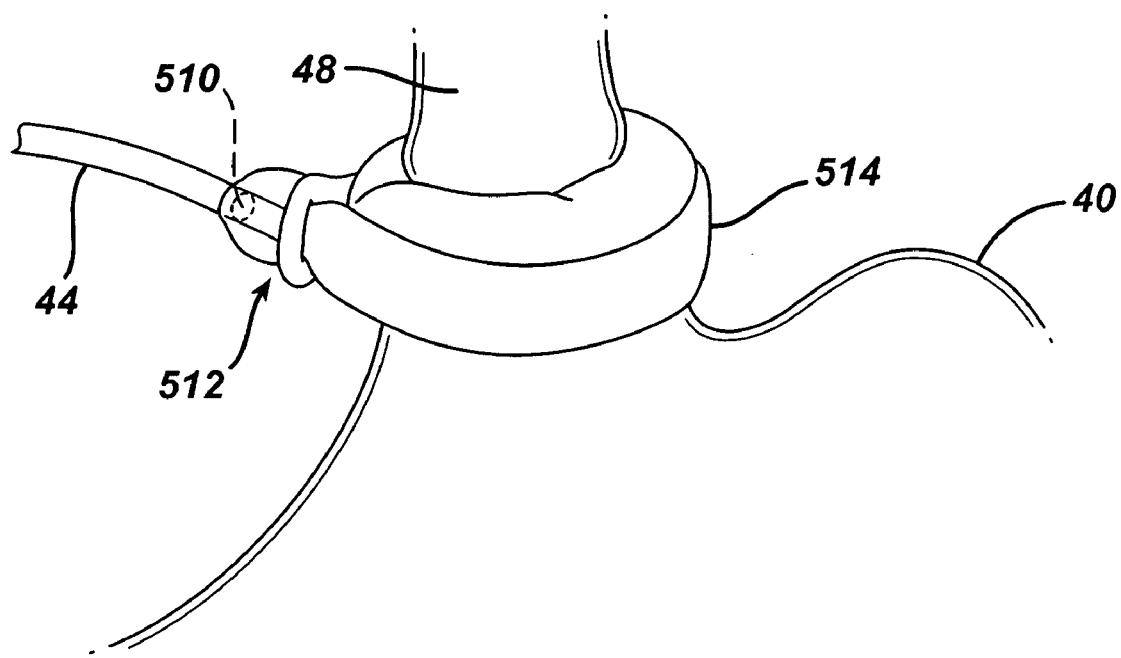
FIG. 43 is a perspective view of a gastric band system with a pressure sensor positioned at the gastric band buckle.

Alternatively, as shown in FIG. 43, a pressure sensor 510 may be located in a buckle 512 of a gastric band 514. In yet another embodiment (not depicted), a pressure sensor is located at the interface of an injection port and catheter, and/or at the interface of a gastric band and catheter. Still other suitable locations for a pressure sensor will be apparent to those of ordinary skill in the art, including but not limited to any location in or adjacent to the fluid path of a gastric band system. In addition, pressure sensors 500, 504, 510, 1504 may be positioned within (e.g., against an inner wall of) their respective band 502, catheter 506, and buckle 512, or alternatively, a portion of such band 502, catheter 506, and buckle 512 may comprise a protrusion extending outwardly therefrom to house at least a portion of the corresponding pressure sensor 500, 504, 510, 1504. Other suitable configurations for housing a pressure sensor 500, 504, 510, 1504 within or adjacent to a band 502, catheter 506, or buckle 512, will be apparent to those of ordinary skill in the art.

Regardless of the location, a pressure sensor 500, 504, 510, 1504 may comprise any off-the-shelf pressure sensor suitable for use, or may be customized for the particular use. Suitable sources for pressure sensors may include CardioMEMS, Integrated Sensing Systems (ISSYS), and Remon Medical. Exemplary pressure sensors may include, but are not limited to, capacitive, piezoresistive, silicon strain gauge, or ultrasonic (acoustic) pressure sensors. In addition, active or passive telemetry may be provided with such a pressure sensor 500, 504, 510, 1504 to receive pressure data from the same using any of the techniques described above or using any other suitable technique. By way of example only, telemetry may be provided using RF, ultrawideband (UWB), ultrasonics, or any other suitable way of communicating. It will also be appreciated that any protocol (e.g., Bluetooth, etc.) within any modality of communication may be used. Accordingly, any of pressure sensors 500, 504, 510, 1504 may comprise a telemetry component (e.g., coil, transmitter, etc.) or be in communication with a telemetry component. To the extent that a telemetry component of a pressure sensor 500, 504, 510, 1504 is unable to reach a telemetry device external to patient 34 without some assistance, such assistance may provided by any suitable number of relays (not shown) or other devices.

In another embodiment, a plurality of pressure sensors 500, 504, 510, 1504 are used. For instance, a gastric band system may comprise a pressure sensor 500 within a gastric band 502 in addition to a pressure sensor 504 within a catheter 506 that is in fluid communication with band 502. Such a plurality of pressure sensors 500, 504 may provide an indication of how well fluid pressure is distributed among components of a gastric band system. Such a plurality of pressure sensors 500, 504 may also provide greater accuracy in pressure readings, reduce the likelihood of catheter obstruction (e.g., pinching) affecting pressure reading, may reduce effects of hydrostatic pressure changes from patient movement, or may provide a variety of other results. It will also be appreciated that any system that includes a plurality of pressure sensors may include a pressure sensor in a port 42, 1142, and/or a pressure sensor external to patient 34 (e.g., pressure sensor 426 in syringe 400 or pressure sensor portion 1426 coupled with syringe 400), in addition to any of the internal pressure sensors 500, 504, 510, 1504 described above. Furthermore, a device such as an internal or external inclinometer (or a substitute therefor) may be used to determine the angle at which patient 34 and/or implanted portion 32 is oriented (e.g., standing, lying down, etc.), which may be factored into pressure data sensed by one or more sensors 500, 504, 510, 1504 to account for hydrostatic pressure effects caused by a patient's 34 orientation. Such a factor (or any other factor) may be accounted for prior to or in conjunction with the rendering of a pressure reading.

In the present example, each of pressure sensors 500, 504, 510, 1504 is hermetically encapsulated, such that inclusion of pressure sensor 500, 504, 510, 1504 will not impact pressure of fluid in implanted portion 32. Of course, a pressure sensor 500, 504, 510, 1504 may be provided without hermetic encapsulation. The inventors further contemplate that any pressure sensor described herein, including but not limited to pressure sensors 500, 504, 510, 1504, may sense pressure in any of a variety of ways. For instance, pressure may be sensed as detecting deflection of a member such as a diaphragm. The degree of such deflection may be a function of force exerted on such member, such that a pressure value may be obtained by factoring in a known surface area. To the extent that calculations are needed to determine pressure as a function of deflection, such calculations may be performed within the sensor or elsewhere. It is also contemplated that pressure may be sensed in a variety of ways other than detecting deflection. For instance, a pressure sensor may comprise a strain gauge configured to measure tension in a member. Still other structures and techniques suitable for sensing or measuring pressure will be apparent to those of ordinary skill in the art. The particular structures and techniques described herein for sensing or measuring pressure are not deemed critical, and the inventors contemplate that any suitable structures and techniques for measuring pressure may be used.

In addition to sensing pressure of fluid within implanted portion 32 as described in various embodiments above, it will be appreciated that pressure of fluid within esophagus 48, upper pouch 50, and/or stomach 40 may also be sensed using any suitable device, such as an endoscopic manometer. By way of example only, such fluid pressure measurements may be compared against measured pressure of fluid within implanted portion 32 before, during, and/or after adjustment of pressure within implanted portion 32. Other suitable uses for measured pressure within esophagus 48, upper pouch 50, and/or stomach 40 will be apparent to those of ordinary skill in the art.

It will become readily apparent to those skilled in the art that the above invention has equally applicability to other types of implantable bands. For example, bands are used for the treatment of fecal incontinence. One such band is described in U.S. Pat. No. 6,461,292 which is hereby incorporated herein by reference. Bands can also be used to treat urinary incontinence. One such band is described in U.S. Patent Application 2003/0105385 which is hereby incorporated herein by reference. Bands can also be used to treat heartburn and/or acid reflux. One such band is described in U.S. Pat. No. 6,470,892 which is hereby incorporated herein by reference. Bands can also be used to treat impotence. One such band is described in U.S. Patent Application 2003/0114729 which is hereby incorporated herein by reference.

While the present invention has been illustrated by description of several embodiments, it is not the intention of the applicant to restrict or limit the spirit and scope of the appended claims to such detail. Numerous other variations, changes, and substitutions will occur to those skilled in the art without departing from the scope of the invention. For instance, the device and method of the present invention has been illustrated in relation to providing the pressure sensor within the injection port. Alternatively, the sensor could be positioned within a fluid filled portion of the band in order to measure pressure changes within the band. Additionally, the pressure sensor could be associated with an elastomeric balloon implanted within the stomach cavity to measure fluid pressure within the balloon. The structure of each element associated with the present invention can be alternatively described as a means for providing the function performed by the element. It will be understood that the foregoing description is provided by way of example, and that other modifications may occur to those skilled in the art without departing from the scope and spirit of the appended Claims.

What is claimed is:

1. A sense head system, comprising:
   (a) a housing;
   (b) a plurality of orthogonal coils, the plurality of orthogonal coils comprising:
      (i) a plurality of horizontal coils, and
      (ii) a plurality of vertical coils, wherein the plurality of orthogonal coils are configured to receive RF signals communicated from a source of RF energy, wherein the plurality of orthogonal coils are located within the housing;

(c) a needle window formed in the housing, wherein the needle window is configured to receive a syringe needle; and (d) a user interface in communication with the plurality of orthogonal coils, wherein the user interface is configured to provide an indication to a user relating to the position of the needle window relative to a needle target located within a patient, wherein data indicative of the position of the needle window relative to the needle target is obtained using the plurality of horizontal coils.

2. The sense head system of claim 1, wherein the housing is generally triangular, wherein each of the horizontal coils is positioned generally at each corner of the triangle, and wherein each of the vertical coils is positioned generally at each corner of the triangle.

3. The sense head system of claim 2, wherein each of the vertical coils is positioned within a corresponding one of the horizontal coils.

4. The sense head system of claim 1, wherein the plurality of orthogonal coils is provided in an arrangement, wherein the needle window is located at the center of the arrangement.

5. The sense head system of claim 1, wherein the user interface comprises a plurality of LEDs.

6. The sense head system of claim 1, wherein the user interface comprises a display device operable to provide a graphical display visually indicating to the user the position of the needle window relative to the needle target.

7. The sense head system of claim 6, where in the graphical display comprises an arrow and a crosshairs, wherein the tip of the arrow represents the needle window, and wherein the center of the crosshairs represents the needle target.

8. The sense head system of claim 1, wherein the user interface is further configured to provide an indication to the user relating to the orientation of the housing relative to the needle target, wherein data indicative of the orientation of the housing relative to the needle target is obtained using the plurality of vertical coils.

9. The sense head system of claim 1, wherein the needle target comprises an injection port.

10. The sense head system of claim 9, wherein the injection port is in communication with an implantable restriction device, wherein the implantable restriction device is operable to form a restriction in a patient using fluid pressure.

11. The sense head system of claim 10, wherein the injection port comprises a pressure sensor configured to sense the pressure of fluid within the implantable restriction device.

12. The sense head system of claim 11, wherein the injection port further comprises a telemetry coil in communication with the pressure sensor, wherein the telemetry coil is configured to transmit signals comprising pressure data, wherein the pressure data is obtained from the pressure sensor.

13. The sense head system of claim 12, further comprising a telemetry coil located within the housing, wherein the telemetry coil is configured to receive pressure data signals from the telemetry coil of the injection port.

14. The sense head system of claim 1, wherein the needle target comprises a coil, wherein the coil is the source of RF energy.

15. A system for positioning a needle and obtaining pressure data, the system comprising:

(a) a sense head, wherein the sense head comprises:
(i) a housing,
(ii) a plurality of receiving coils operable to receive RF signals communicated from a source of RF energy, wherein the coils are located within the housing,
(iii) a needle window formed through the housing, wherein the needle window is configured to receive a needle, and
(iv) a telemetry coil configured to receive pressure data obtained from a pressure sensor configured to sense the pressure of a fluid within a patient; and (b) a display device in communication with the sense head, wherein the display device is configured to provide an indication to a user relating to the position of the needle window over a needle target, wherein data indicative of the position of the needle window over the needle target is obtained using the plurality of receiving coils, wherein the display device is further configured to process the pressure data.

16. The system of claim 15, further comprising a restriction system, the restriction system comprising:
(i) a restriction device for implantation in a patient to form a restriction in the patient,
(ii) an implanted port in fluid communication with the restriction device, wherein the port is configured to receive fluid from a needle passed through the needle window of the sense head, wherein the port is further configured for withdrawal of fluid from the port by a needle, wherein the port comprises the needle target, and
(iii) a fluid, wherein the fluid is located in the restriction device and in the implanted port, wherein the pressure sensor is configured to sense the pressure of the fluid.

17. The system of claim 15, wherein the display device is further configured to provide an indication to the user relating to the orientation of the housing relative to the needle target, wherein data indicative of the orientation of the housing relative to the needle target is obtained using the plurality of receiving coils.

18. The system of claim 17, wherein the display device is further configured to display a visual representation of the pressure data.

19. A method for selecting a location for inserting a needle into a patient, the method comprising:

(a) providing a sense head, wherein the sense head comprises:
(i) a housing,
(ii) a plurality of receiving coils operable to receive RF signals communicated from a source of RF energy, wherein the coils are located within the housing, and
(iii) a needle window formed through the housing, wherein the needle window is configured to receive a needle;

(b) placing the sense head adjacent to a patient, wherein the patient has an implanted restriction system, the implanted restriction system comprising (i) an injection port, wherein the injection port comprises one or more telemetry coils, wherein at least one of the one or more coils is the source of RF energy,
(ii) a restriction device operable to adjustably form a restriction within the patient,
(iii) a fluid, wherein the fluid is located in the injection port and in the restriction device, and
(iv) a pressure sensor operable to capture data indicative of the pressure of the fluid;

(c) positioning the sense head substantially over the injection port, wherein the act of positioning the sense head over the injection port comprises monitoring RF signals received by the plurality of receiving coils to determine the position of the sense head relative to the injection port; and (d) inserting a needle through the needle window into the injection port.

20. The method of claim 19, the method further comprising obtaining pressure data captured by the pressure sensor, wherein the pressure data is obtained via the sense head.

* * * * *